US010288611B2

(12) United States Patent
Marr et al.

(10) Patent No.: US 10,288,611 B2
(45) Date of Patent: *May 14, 2019

(54) LATERAL FLOW DEVICE FOR DIAGNOSING MICROBIAL INFECTIONS

(75) Inventors: Kieren A. Marr, Baltimore, MD (US); Janet F. Staab, Baltimore, MD (US); Marta Feldmesser, New York, NY (US)

(73) Assignees: The Johns Hopkins University, Baltimore, MD (US); Albert Einstein College of Medicine, Inc., Bronx, NY (US)

( * ) Notice: Subject to any disclaimer, the term of this patent is extended or adjusted under 35 U.S.C. 154(b) by 1252 days.

This patent is subject to a terminal disclaimer.

(21) Appl. No.: 13/511,264

(22) PCT Filed: Nov. 23, 2010

(86) PCT No.: PCT/US2010/057819
§ 371 (c)(1),
(2), (4) Date: Sep. 25, 2012

(87) PCT Pub. No.: WO2011/063395
PCT Pub. Date: May 26, 2011

(65) Prior Publication Data
US 2013/0017561 A1  Jan. 17, 2013

Related U.S. Application Data

(60) Provisional application No. 61/263,498, filed on Nov. 23, 2009.

(51) Int. Cl.
*G01N 33/53* (2006.01)
*G01N 33/569* (2006.01)
*G01N 33/66* (2006.01)
*C07K 16/14* (2006.01)
*G01N 33/543* (2006.01)

(52) U.S. Cl.
CPC ....... *G01N 33/56961* (2013.01); *C07K 16/14* (2013.01); *G01N 33/54366* (2013.01); *G01N 33/569* (2013.01); *G01N 33/66* (2013.01); *G01N 2400/02* (2013.01); *G01N 2469/10* (2013.01)

(58) Field of Classification Search
USPC ......... 530/387.1, 388.1; 435/975; 424/130.1, 424/141.1, 150.1
See application file for complete search history.

(56) References Cited

U.S. PATENT DOCUMENTS

| | | |
|---|---|---|
| 4,943,522 A | 7/1990 | Eisinger et al. |
| 5,149,632 A | 9/1992 | Notermans et al. |
| 5,710,005 A | 1/1998 | Rittenburg |
| 5,766,961 A * | 6/1998 | Pawlak et al. ............... 436/510 |
| 5,876,961 A | 3/1999 | Crowe et al. |
| 5,945,294 A | 8/1999 | Frank et al. |
| 6,500,629 B1 | 12/2002 | Cleaver et al. |
| 7,097,983 B2 * | 8/2006 | Markovsky et al. .......... 435/7.1 |
| 7,371,582 B2 | 5/2008 | Nahm et al. |
| 2002/0045195 A1 | 4/2002 | Hubscher et al. |
| 2003/0082533 A1 | 5/2003 | Yue et al. |
| 2003/0148484 A1 | 8/2003 | Koentgen et al. |
| 2004/0018556 A1 | 1/2004 | Cantor |
| 2005/0042738 A1 | 2/2005 | Swarnakar et al. |
| 2005/0074410 A1 | 4/2005 | Cramer et al. |
| 2005/0214836 A1 | 9/2005 | Nakamura et al. |
| 2005/0214951 A1 | 9/2005 | Nahm et al. |
| 2005/0272106 A1 | 12/2005 | Moore et al. |
| 2006/0019406 A1 | 1/2006 | Wei et al. |
| 2006/0121626 A1 | 6/2006 | Imrich |
| 2006/0127886 A1 | 6/2006 | Kaylor et al. |
| 2006/0134608 A1 | 6/2006 | Guo et al. |
| 2006/0148102 A1 | 7/2006 | Guo et al. |
| 2006/0241288 A1 | 10/2006 | Roche et al. |
| 2007/0020711 A1 | 1/2007 | Wheat |
| 2008/0147031 A1 | 6/2008 | Long et al. |
| 2009/0117585 A1 | 5/2009 | Van Den Hondel |

(Continued)

FOREIGN PATENT DOCUMENTS

| | | |
|---|---|---|
| EP | 0325004 A1 | 7/1989 |
| EP | 1104768 A1 | 6/2001 |

(Continued)

OTHER PUBLICATIONS

Schmalhorst et al (Eukaryot Cell. Aug. 2008;7(8):1268-77).*
Greenspan et al (Nature Biotechnology 7: 936-937, 1999).*
Chothia et al (The EMBO Journal, 1986, 5/4:823-26).*
Thornton, CR (Clin Vaccine Immunol. Jul. 2008;15(7):1095-105).*
Knutsen et al., "Asp f1 CD4+ Th2-like T cell lines in allergic bronchopulmonary aspergillosis." J Allergy Clin Immunol, 1994, 94: p. 215-221.
Kawamura et al., "Clinical evaluation of 61 patients with pulmonary aspergilloma." Intern Med, 2000. 39(3): p. 209-12.
Israel et al., "Sarcoidosis and aspergilloma" Chest, 1982. 82: p. 430-32.
Kirsten et al., "Invasive aspergillosis in cavitary lung sarcoidosis." Pneumologie, 1992. 46: p. 239-242.

(Continued)

*Primary Examiner* — Jennifer E Graser
(74) *Attorney, Agent, or Firm* — Mintz Levin Cohn Ferris Glovsky and Popeo, P.C.; Peter F. Corless

(57) ABSTRACT

Fungal infections are difficult to diagnose. The most common filamentous fungal infection, aspergillosis, carries with it a high mortality. Culture of the organism is difficult and obtaining samples, e.g., though a lung biopsy, sometimes causes morbidity. Biomarkers that indicate 'early' infection in it development are sought after. One such biomarker is detection of galactomannan (GM), a polysaccharide that is attached to hyphal cell walls and secreted during growth of the organism. Galactomannan is excreted in urine. Disclosed herein is a lateral flow assay comprising monoclonal antibodies that recognize specific residues of *Aspergillus fumigates* for detecting GM in urine samples to provide a point-of-care detection device to allow for frequent screening and early diagnosis in patients at high risk for infection.

26 Claims, 20 Drawing Sheets

Specification includes a Sequence Listing.

(56) References Cited

U.S. PATENT DOCUMENTS

| | | | |
|---|---|---|---|
| 2010/0119533 A1 | 5/2010 | Clancy et al. |
| 2010/0168023 A1 | 7/2010 | Ruegg et al. |
| 2012/0064093 A1 | 3/2012 | Thornton |
| 2013/0017561 A1 | 1/2013 | Marr et al. |
| 2013/0130274 A1 | 5/2013 | Kelly |
| 2014/0178884 A1 | 6/2014 | Aucoin et al. |
| 2014/0212436 A1 | 7/2014 | Moore et al. |

FOREIGN PATENT DOCUMENTS

| | | |
|---|---|---|
| WO | 2007/011221 A2 | 1/2007 |
| WO | WO2007015177 A2 | 2/2007 |

OTHER PUBLICATIONS

Wollschlager et al., "Aspergilloma complicating sarcoidosis. A prospective study of 100 patients." Chest, 1984. 86: p. 585-88.

Staples et al., "Invasive pulmonary aspergillosis in AIDS: radiographic, CT, and pathologic findings" Radiology, 1995. 196(2): p. 409-14.

Hines et al., "Pseudomembranous tracheobronchitis caused by Aspergillus." Am Rev Respir Dis, 1991. 143(6): p. 1408-11.

Khoo et al., "Invasive aspergillosis in patients with AIDS." Clin Infect Dis, 1994. 19 Suppl 1(2): p. S41-8.

Duong et al., "Kinetic study of host defense and inflammatory response to Aspergillus fumigatus in steroid-induced immunosuppressed mice." J Infect Dis, 1998. 178: p. 1472-82.

Berenguer et al., "Pathogenesis of pulmonary aspergillosis. Granulocytopenia versus cyclosporine and methylprednisolone-induced immunosuppression." Am J Respir Crit Care Med, 1995. 152(3): p. 1079-86.

Marr et al., "Aspergillosis in HSCT recipients: evidence for two distinct pathophysiologic conditions associated with engraftment status." Blood, 2000. 96(11).

Boeckh et al., "Successful modification of a pp65 antigenemia-based early treatment strategy for prevention of cytomegalovirus disease in allogeneic marrow transplant recipients." Blood, 1999. 93(5): p. 1781-2.

Boeckh et al., "Effect of high-dose acyclovir on survival in allogeneic marrow transplant recipients who received ganciclovir at engraftment or for cytomegalovirus pp65 antigenemia." J Infect Dis, 1998. 1998(178): p. 1153-7.

Boeckh et al., "Plasma polymerase chain reaction for cytomegalovirus DNA after allogeneic marrow transplantation: comparison with polymerase chain reaction using peripheral blood leukocytes, pp65 antigenemia, and viral culture." Transplantation, 1997. 64: p. 108-113.

Boeckh et al., "Cytomegalovirus pp65 antigenemia-guided early treatment with ganciclovir versus ganciclovir at engraftment after allogeniec marrow transplantation: a randomized double-blind study." Blood, 1996. 88(10): p. 4063-4071.

Slavin et al., "Efficacy and safety of fluconazole prophylaxis for fungal infections after marrow transplantation—a prospective, randomized, double-blind study." Journal of Infectious Diseases., 1995. 171(6): p. 1545-52.

Hansen et al., "Bone marrow transplants from unrelated donors for patients with chronic myeloid leukemia." The New England Journal of Medicine, 1998. 338: p. 962-8.

Marr et al., "Epidemiology and outcome of mould infections in hematopoietic stem cell transplant recipients." Clin Infect Dis, 2002. 34: p. 909-917.

Wald et al., "Epidemiology of Aspergillus infections in a large cohort of patients undergoing bone marrow transplantation." The Journal of Infectious Diseases, 1997. 175: p. 1459-66.

Neofytos et al., "Epidemiology and outcome of invasive fungal infection in adult hematopoietic stem cell transplant recipients: analysis of Multicenter Prospective Antifungal Therapy (PATH) Alliance registry." Clin Infect Dis, 2009. 48(3): p. 265-73.

Durkin et al., "Diagnosis of coccidioidomycosis with use of the Coccidioides antigen enzyme immunoassay." Clin Infect Dis, 2008. 47(8): p. e69-73.

Spector et al., "Antigen and antibody testing for the diagnosis of blastomycosis in dogs." J Vet Intern Med, 2008. 22(4): p. 839-43.

Kim et al., "Halo sign on high resolution CT: findings in spectrum of pulmonary diseases with pathologic correlation." J Comput Assist Tomogr, 1999. 23(4): p. 622-6.

Caillot et al., "Improved management of invasive aspergillosis in neutropenic patients using early thoracic computed tomographic scan and surgery." Journal of Clinical Oncology, 1997. 15(1): p. 139-147.

Levy et al., "The value of bronchoalveolar lavage and bronchial washings in the diagnosis of invasive pulmonary aspergillosis." Respir Med, 1992. 86(3): p. 243-8.

Hoffer et al., "Accuracy of percutaneous lung biopsy for invasive pulmonary aspergillosis." Pediatr Radiol, 2001. 31(3): p. 144-52.

De Sevaux et al., "Microgranulomatous aspergillosis in a patient with chronic granulomatous disease: cure with voriconazole." Clin Infect Dis, 1998. 26(4): p. 996-7.

Marr et al., "Detection of galactomannan antigenemia by enzyme immunoassay for the diagnosis of invasive aspergillosis: variables that affect performance." J Infect Dis, 2004. 190(3): p. 641-9.

Upton et al., "Reproducibility of low galactomannan enzyme immunoassay index values in multiple laboratories." in preparation, 2005.

Marr, "Aspergillus galactomannan index: a surrogate end point to assess outcome of therapy?" Clin Infect Dis, 2008. 46(9): p. 1423-5.

Sheppard et al., "Comparison of three methodologies for the determination of pulmonary fungal burden in experimental murine aspergillosis." Clin Microbiol Infect 2006. 12(4): p. 376-80.

Upton et al., "(1→3) beta-D-glucan assay in the diagnosis of invasive fungal infections." Clin Infect Dis, 2006. 42(7): p. 1054-6; author reply 1056.

Marr et al., "Design issues in studies evaluating diagnostic tests for aspergillosis." Clin Infect Dis, 2005.41 Suppl 6: p. S381-6.

Marr et al., "Antifungal therapy decreases sensitivity of the Aspergillus galactomannan enzyme immunoassay." Clin Infect Dis, 2005. 40(12): p. 1762-9.

Musher et al., "Aspergillus galactomannan enzyme immunoassay and quantitative PCR for diagnosis of invasive aspergillosis with bronchoalveolar lavage fluid." J Clin Microbiol, 2004. 42(12): p. 5517-22.

Stynen et al., "Rat monoclonal antibodies against Aspergillus galactomannan." Infect Immun, 1992. 60(6): p. 2237-45.

Denning et al., "Efficacy and safety of voriconazole in the treatment of acute invasive aspergillosis." Clin Infect Dis, 2002. 34(5): p. 563-71.

Maertens et al., "Optimization of the cutoff value for the Aspergillus double-sandwich enzyme immunoassay." Clin Infect Dis, 2007. 44(10): p. 1329-36.

Rath et al., "Value of environmental sampling and molecular typing of aspergilli to assess nosocomial sources of aspergillosis." J Hosp Infect, 1997. 37(1): p. 47-53.

Eskens et al., "Septic shock caused by group G beta-haemolytic streptococci as presenting symptom of acute myeloid leukaemia." Neth J Med, 1995. 46(3): p. 153-5.

Einsele et al., "Prediction of invasive pulmonary aspergillosis from colonisation of lower respiratory tract before marrow transplantation." Lancet, 1998. 352(9138): p. 1443.

Buchheidt et al., "Detection of *Aspergillus* species in blood and bronchoalvolar lavage samples from immunocompromised patients by means of 2-step polymerase chain reaction: clinical results." Clin Infect Dis, 2001. 33: p. 428-35.

Meersseman et al., "Galactomannan in bronchoalveolar lavage fluid: a tool for diagnosing aspergillosis in intensive care unit patients." Am J Respir Crit Care Med, 2008. 177(1): p. 27-34.

Husain et al., "Performance characteristics of the platelia Aspergillus enzyme immunoassay for detection of Aspergillus galactomannan antigen in bronchoalveolar lavage fluid." Clin Vaccine Immunol, 2008. 15(12): p. 1760-3.

(56) References Cited

OTHER PUBLICATIONS

Nguyen et al., "Use of bronchoalveolar lavage to detect galactomannan for diagnosis of pulmonary aspergillosis among nonimmunocompromised hosts." J Clin Microbiol, 2007. 45(9): p. 2787-92.
Husain et al., "Aspergillus galactomannan antigen in the bronchoalveolar lavage fluid for the diagnosis of invasive aspergillosis in lung transplant recipients." Transplantation, 2007. 83(10): p. 1330-6.
Clancy et al., "Bronchoalveolar lavage galactomannan in diagnosis of invasive pulmonary aspergillosis among solid-organ transplant recipients." J Clin Microbiol, 2007. 45(6): p. 1759-65.
Sanguinetti et al., "Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis." J Clin Microbiol, 2003. 41(8): p. 3922-5.
Becker et al., "Galactomannan detection in computerized tomography-based broncho-alveolar lavage fluid and serum in haematological patients at risk for invasive pulmonary aspergillosis." Br J Haematol, 2003. 121(3): p. 448-57.
Jensen et al., "Detection of galactomannan and the 18 kDa antigen from Aspergillus fumigatus in serum and urine from cattle with systemic aspergillosis." Zentralbl Veterinarmed [B], 1993. 40(6): p. 397-408.
Bennett et al., "Receptor-mediated clearance of Aspergillus galactomannan." J Infect Dis, 1987. 155(5): p. 1005-10.
Klont et al., "Utility of Aspergillus antigen detection in specimens other than serum specimens." Clin Infect Dis, 2004. 39(10): p. 1467-74.
Ansorg et al., "Aspergillus antigenuria compared to antigenemia in bone marrow transplant recipients." Eur J Clin Microbiol Infect Dis, 1994. 13(7): p. 582-9.
Dupont et al., "Galactomannan antigenemia and antigenemia in aspergillosis: studies in patients and experimentally infected rabbits." J Infect Dis, 1987. 155(1): p. 1-11.
Rogers et al., "Value of antigen detection in predicting invasive pulmonary aspergillosis." Lancet, 1990. 336(8725): p. 1210-3.
Tsoni et al., "beta-Glucans and dectin-1." Ann N Y Acad Sci, 2008. 1143: p. 45-60.
Obayashi et al., "Plasma (1→3)-beta-D-glucan measurement in diagnosis of invasive deep mycosis and fungal febrile episodes." Lancet, 1995. 345(8941): p. 17-20.
Gersuk et al., "Dectin-1 and TLRs permit macrophages to distinguish between different Aspergillus fumigatus cellular states." J Immunol, 2006. 176(6): p. 3717-24.
Hohl et al., "Aspergillus fumigatus triggers inflammatory responses by stage-specific beta-glucan display." PLoS Pathog, 2005. 1(3): p. e30.
Steele et al., "The beta-glucan receptor dectin-1 recognizes specific morphologies of Aspergillus fumigatus." PLoS Pathog, 2005. 1(4): p. e42.
Hachem et al., "Utility of galactomannan enzyme immunoassay and (1.3) beta-D-glucan in diagnosis of invasive fungal infections: low sensitivity for Aspergillus fumigatus infection in hematologic malignancy patients." J Clin Microbiol, 2009. 47(1): p. 129-33.
Senn et al., "1,3-Beta-D-glucan antigenemia for early diagnosis of invasive fungal infections in neutropenic patients with acute leukemia." Clin Infect Dis, 2008. 46(6): p. 878-85.
Persat et al., "Contribution of the (1→3)-beta-D-glucan assay for diagnosis of invasive fungal infections." J Clin Microbiol, 2008. 46(3): p. 1009-13.
Pickering et al., "Evaluation of a (1→3)-beta-D-glucan assay for diagnosis of invasive fungal infections." J Clin Microbiol, 2005. 43(12): p. 5957-62.
Ellis et al., "Assessment of the clinical utility of serial beta-D-glucan concentrations in patients with persistent neutropenic fever." J Med Microbiol, 2008. 57(Pt 3): p. 287-95.
Boulware et al., "Rapid diagnosis of pneumococcal pneumonia among HIV-infected adults with urine antigen detection." J Infect, 2007. 55(4): p. 300-9.
Sutherland et al., "In vivo fate and distribution of poly-gamma-D-glutamic acid, the capsular antigen from Bacillus anthracis." Infect Immun, 2008. 76(3): p. 899-906.
Clarke, "Urinary antigen diagnosis of meningococcal disease." Br J Biomed Sci, 2000. 57(2): p. 153-5.
Van Burik et al., "Panfungal PCR assay for detection of fungal infection in human blood samples." J Clin Microbiol, 1998. 36(5): p. 1169-1175.
Hebart et al., "Early detection of aspergillus infection after allogeneic stem cell transplantation polymerase chain reaction screening." J Infect Dis, 2000. 181(5): p. 1713-9.
Kami et al., "Use of real-time PCR on blood samples for diagnosis of invasive aspergillosis." Clin Infect Dis, 2001. 33(9): p. 1504-12.
Costa et al., "Real-Time PCR Coupled with Automated DNA Extraction and Detection of Galactomannan Antigen in Serum by Enzyme-Linked Immunosorbent Assay for Diagnosis of Invasive Aspergillosis." J Clin Microbiol, 2002. 40(6): p. 2224-2227.
Costa et al., "Development of two real-time quantitative TaqMan PCR assays to detect circulating Aspergillus fumigatus DNA in serum," J Microbiol Methods, 2001. 44(3): p. 263-9.
Cuenca-Estrella et al., "Value of serial quantification of fungal DNA by a real-time PCR-based technique for early diagnosis of invasive Aspergillosis in patients with febrile neutropenia." J Clin Microbiol, 2009. 47(2): p. 379-84.
Suarez et al., "Detection of circulating Aspergillus fumigatus DNA by real-time PCR assay of large serum volumes improves early diagnosis of invasive aspergillosis in high-risk adult patients under hematologic surveillance." J Clin Microbial, 2008. 46(11): p. 3772-7.
Nielsen et al., "Prototype single step lateral flow technology for detection of avian influenza virus and chicken antibody to avian influenza virus." J Immunoassay Immunochem, 2007. 28(4): p. 307-18.
Mokkapati et al., "Evaluation of UPlink-RSV: prototype rapid antigen test for detection of respiratory syncytial virus injection." Ann NY Acad Sci, 2007. 1098: p. 476-85.
Koide et al., "Comparative evaluation of Duopath Legionella lateral flow assay against the conventional culture method using Legionella pneumophila and Legionella anisa strains." Jpn J Infect Dis, 2007. 60(4): p. 214-6.
Roson et al., "Contribution of a urinary antigen assay (Binax NOW) to the early diagnosis of pneumococcal pneumonia." Clin Infect Dis, 2004. 38(2): p. 222-6.
Weatherall et al., "Point-of-care urinary pneumococcal antigen less in the emergency department for community acquired pneumonia." Emerg Med J, 2008. 25(3): p. 144-8.
Kappe et al., "New cause for false-positive results with the Pastorex Aspergillus antigen latex agglutination test." J Clin Microbial, 1993. 31(9): p. 2489-90.
Swanink et al., "Specificity of a sandwich enzyme-linked immunosorbent assay for detecting Aspergillus galactomannan." J Clin Microbial, 1997. 35(1): p. 257-60.
Thornton, "Development of an immunochromatographic lateral-flow device for rapid serodiagnosis of invasive aspergillosis." Clin Vaccine Immunol, 2008. 15(7): p. 1095-105.
Ascioglu et al., "Defining opportunistic invasive fungal infections in immunocompromised patients with cancer and hematopoietic stem cell transplants: an international consensus." Clin. Infect Dis, 2002. 34: p. 7-14.
Knot et al., "Development and optimization of quantitative PCR for the diagnosis of invasive aspergillosis with bronchoalveolar lavage fluid." BMC Infect Dis, 2008. 8: p. 73.
Fredricks et al., "Comparison of six DNA extraction methods for recovery of fungal DNA as assessed by quantitative PCR." J Clin Microbial, 2005. 43(10): p. 5122-8.
Dalle et al., "Cryptococcus neoformans Galactoxylomannan contains an epitope(s) that is cross-reactive with Aspergillus Galactomannan." J Clin Microbial, 2005. 43(6): p. 2929-31.
Brown, Antibodies: key to a robust lateral flow immunoassay, in Lateral Flow Immunoassay, H.Y.T.R.C. Wong, Editor. 2009, Humana Press: New York, N.Y. p. 59-74.

(56) References Cited

OTHER PUBLICATIONS

Mennink-Kersten et al., "Bifidobacterium lipoteichoic acid and false ELISA reactivity in aspergillus antigen detection." Lancet, 204. 363(9405): p. 325-7.

Walsh et al., "Experimental pulmonary aspergillosis due to Aspergillus terreus: pathogenesis and treatment of an emerging fungal pathogen resistant to amphotericin B." J Infect Dis, 2003. 188(2): p. 305-19.

Marr et al., "Antifungal therapy decreases sensitivity of the Platelia Aspergillus galactomannan enzyme immunoassay." submitted, 2005.

Leisenring et al., "A marginal regression modelling framework for evaluating medical diagnostic tests." Statistics in Medicine, 1997. 16(11): p. 1263-1281.

Sheppard et al., "Novel inhalational murine model of invasive pulmonary aspergillosis." Antimicrob Agents Chemother, 2004. 48(5): p. 1908-11.

Sheppard et al., "Standardization of an experimental murine model of invasive pulmonary aspergillosis." Antimicrob Agents Chemother, 2006. 50(10): p. 3501-3.

Stynen et al., "A New Sensitive Sandwich Enzyme-Linked Immunosorbent Assay to Detect Galactofuran in patients with Invasive Aspergillosis," J. Clin. Micro., vol. 33, No. 2, Feb. 1995, pp. 497-500.

Hurst et al., "Comparison of Commercial Latex Agglutination and Sandwich Enzyme Immunoassays with a Competitive Binding Inhibition Enzyme Immunoassay for Detection of Antigenemia and Antigenuria in a Rabbit Model of Invasive Aspergillosis," Clin. Diag. Lab. Immun., vol. 7, No. 3, May 2000, pp. 477-485.

Salonen et al., "Aspergillus antigen in serum, using and broncholaveolar lavage specimens of neutropenic patients in relation to clinical outcome," Scandinavian Journal of Infectious Diseases, 2000, 32, pp. 485-490.

Mennink-Kersten, M. et al., "In Vitro Release by Aspergillus fumigatus of GA lactofuranose Antigens, 1,3-beta-D-Glucan, and DNA, Surrogate Markers Used for Diagnosis of Invasive Aspergillosis", Journal of Clinical Microbiology, May 2006, vol. 44, No. 5, pp. 1711-1718.

Domenech, J. et al., "Galactomannans from the cell walls of species of *Paeci lomyces* sect. *Paecilomyces* and their telemorphs as immunotaxonomic markers" Microbiology, 1999, vol. 145. pp. 2789-2796.

Masaya, O., et al, "Novel B-D-Galactofuranose-containing High Mannose Type Oligosaccharides in Ascorbate Oxidase from Acremonium sp HI-25", Bioscience, Biotechnology and Biochemistry (1996) vol. 60, No. 7, pp. 1123-1130.

Sarfati, J et al, "Antigens of Aspergillus fumigatus produced in vivo" Journal of Medical and Veterinary Mycology (1995) vol. 33, pp. 9-14.

Latge, Jean-Paul, "Galactofuranose containing molecules in Aspergillus fumigatus" Medical Mycology (2009) vol. 47 (supplement 1), pp. 8104-8109.

Anastasakou, E et al, ECCMID, 9th, Aspergillus and Aspergillosis Website, Ref. ID 2970, year 1999, abstract, "Detection of antigen galactomannan of Aspergillus in the urine of patients with lung disease".

Suzuki, E. et al, Clinical and Diagnostic Laboratory Immunology, Sep. 2001, vol. 8(5), pp. 1031-1035, "Reactivity of MEST-1 (Antigalactofuranose) with Trypanosoma cruzi Glycosylinositol Phosphorylceramides (GIPCs): Immunolocalization of GIPCs in Acidic Vesicles of Epimastigotes".

Latge, Jean-Paul et al, Infection and Immunity, vol. 62(12), Dec. 1994, pp. 5424-5433, "Chemical and Immunological Characterization of the Extracellular Galactomannan of Aspergillus fumigatus".

Leitao, E. A. et al, Glycobiology, vol. 13(10), pp. 681-692, 2003, "B-Galactofuranose-containing O-linked oligosaccharides present in cell wall peptidogalactomannan of Aspergillus fumigatus contain immunodominant epitopes".

Office Action dated Apr. 30, 2015 for U.S. Appl. No. 14/546,830.

Final Office Action dated Feb. 24, 2016 in related U.S. Appl. No. 14/546,830.

Ansorg, R et al, European Journal of Clinical Microbiology and Infectious Disease, (1994) vol. 13(7), pp. 582-589, "Aspergillus Antigenuria Compared to Antigenemia in Bone Marrow Transplant Recipients".

Dupont, B et al, The Journal of Infectious Diseases, vol. 155(1) Jan. 1, 1987, pp. 1-11, "Galactomannan Antigenemia and Antigenuria in Aspergillus: Studies in Patients and Experimentally Infected Rabbits".

Kamphuis, HJ, (1992) Ph.D. Thesis, Wageningen Agricultural University, pp. 1-157 "Extracelluar polysaccharides as target Compounds for the Immunological Detection of Aspergillus and Penicillium in Food" Chapters 1-9, Agricultural University Wageningen, Netheralands.

Klont, RR et al, Clinical Infectious Diseases, (2004) vol. 39, pp. 1467-1474, "Utility of Aspergillus Antigen Detection in Specimens other than Serum Specimens".

Wiederhold, N. et al, Clinical and Vaccine Immunology, (2009) published on line ahead of print Sep. 30, 2009, pp. 1844-1846, vol. 16(12), "Comparison of Lateral Flow Technology and Galactomannan and (1>3)-B-D-Glucan Assays for Detection of Invasive Pulmonary Aspergillus".

Supplemental Response filed Jul. 8, 2016, in Response to Final Office Action dated Feb. 23, 2016, in related case U.S. Appl. No. 14/546,830.

Response and Amendment filed Apr. 22, 2016, in Response to Final Office Action dated Feb. 23, 2016 in related U.S. Appl. No. 14/546,830.

Response and Amendment and 1.132 Declarations filed Jun. 11, 2015 in Response to Office Action dated Apr. 30, 2015 in related U.S. Appl. No. 14/546,830.

* cited by examiner

SEQUENCE LISTING

```
<160> NUMBER OF SEQ ID NOS: 10

<210> SEQ ID NO 1
<211> LENGTH: 339
<212> TYPE: DNA
<213> ORGANISM: Mus musculus
<220> FEATURE:
<221> NAME/KEY: misc_feature
<222> LOCATION: (1)..(339)
<223> OTHER INFORMATION: 205 VH (15A)

<400> SEQUENCE: 1
gaggtgcagc tggaggagtc tctgagactc tcctgtgcaa cttctgggtt caccttcagt      60
gatttctaca tggagtgggt ccgccagcct ccagggaaga gactggagtg gattgctgca     120
agtagaaaca aagctaatga ttatacaaca gagtacagtg catctgtgaa gggtcggttc     180
atcgtctcca gagacacttc ccaaagcatc ctctaccttc agatgaatgc cctgagagct     240
gaggacactg ccatttatta ctgtgcaaga gattactacg gtagtagcta ctggtacttc     300
gatgtctggg gcgcagggac cacggtcacc gtctcctca                            339

<210> SEQ ID NO 2
<211> LENGTH: 341
<212> TYPE: DNA
<213> ORGANISM: Mus musculus
<220> FEATURE:
```

<221> NAME/KEY: misc_feature
<222> LOCATION: (1)..(341)
<223> OTHER INFORMATION: 205 VL (P1A)

<400> SEQUENCE: 2
gacattctga tgacccagtc tccaactttc cttgctgtga cagcaagtaa gaaggtcacc   60
attagttgca cggccagtga gagcctttat tcaagcaaac acaaggtgca ctacttggct  120
tggtaccaga agaaaccaga gcaatctcct aaactgctga tatacggggc atccaaccga  180
tacattgggg tccctgatcg cttcacaggc agtggatctg gacagatttt cactctgacc  240
atcagcagtg tacaggttga agacctcaca cattattact gtgcacagtt ttacagctat  300
cctctcacgt tcggctcggg gacaaagttg gaaataaaac g                     341

<210> SEQ ID NO 3
<211> LENGTH: 359
<212> TYPE: DNA
<213> ORGANISM: Mus musculus
<220> FEATURE:
<221> NAME/KEY: misc_feature
<222> LOCATION: (1)..(359)
<223> OTHER INFORMATION: 24.22.1 VH (PA7)
<220> FEATURE:
<221> NAME/KEY: misc_feature
<222> LOCATION: (18)..(18)
<223> OTHER INFORMATION: n is a, c, g, or t

<400> SEQUENCE: 3
gaggtgcagc tggaggantc tgggggagac ttagtgaagc ctggagggtc cctgaaactc   60
tcctgtgcag cctctggatt cactttcagt agctatggca tgtcttgggt tcgccagact  120
ccagacaaga ggctggagtg ggtcgcaacc attagtagtg gtggtagtta cacctactat  180
ccagacagtg tgaaggggcg attcaccatc tccagagaca tgccaagaa cacccctgtac  240 ctgcaaatga gcagtctgaa gtctgaggac acagccatgt attactgtgc aagacttact  300
acggtagtag ctatgctatg gactactggg gtcaaggaac ctcagtcacc gtctcctca  359

<210> SEQ ID NO 4
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 24.22.1 VL (B6A)

<400> SEQUENCE: 4
gacattctga tgacccagtc tccaactttc cttgctgtga cagcaagtaa gaaggtcacc   60
attagttgca cggccagtga gagcctttat tcaagcaaac acaaggtgca ctacttggct  120
tggtaccaga agaaaccaga gcaatctcct aaactgctga tatacggggc atccaaccga  180
tacattgggg tccctgatcg cttcacaggc agtggatctg gacagatttt cactctgacc  240
atcagcagtg tacaggttga agacctcaca cattattact gtgcacagtt ttacagctat  300
cctctcacgt tcggtgctgg gaccaagctg gagctgaaac g                     341

<210> SEQ ID NO 5
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 686.8.5 VH (C5A)

<400> SEQUENCE: 5

```
gacattctga tgacccagtc tccaactttc cttgctgtga cagcaagtaa gaaggtcacc    60
attagttgca cggccagtga gagcctttat tcaagcaaac acaaggtgca ctacttggct   120
tggtaccaga agaaaccaga gcaatctcct aaactgctga tatacggggc atccaaccga   180
tacattgggg tccctgatcg cttcacaggc agtggatctg gacagatttt cactctgacc   240
atcagcagtg tacaggttga agacctcaca cattattact gtgcacagtt ttacagctat   300
cctctcacgt tcggtgctgg gaccaagctg gagctgaaac g                       341
```

<210> SEQ ID NO 6
<211> LENGTH: 341
<212> TYPE: DNA
<213> ORGANISM: Mus musculus
<220> FEATURE:
<221> NAME/KEY: misc_feature
<222> LOCATION: (1)..(341)
<223> OTHER INFORMATION: 686.8.5 VL (P2A)

<400> SEQUENCE: 6

```
gacattctga tgacccagtc tccaactttc cttgctgtga cagcaagtaa gaaggtcacc    60
attagttgca cggccagtga gagcctttat tcaagcaaac acaaggtgca ctacttggct   120
tggtaccaga agaaaccaga gcaatctcct aaactgctga tatacggggc atccaaccga   180
tacattgggg tccctgatcg cttcacaggc agtggatctg gacagatttt cactctgacc   240
atcagcagtg tacaggttga agacctcaca cattattact gtgcacagtt ttacagctat   300
ccgctcacgt tcggtgctgg gaccaagctg gagctgaaac g                       341
```

<210> SEQ ID NO 7
<211> LENGTH: 342
<212> TYPE: DNA
<213> ORGANISM: Mus musculus
<220> FEATURE:
<221> NAME/KEY: misc_feature
<222> LOCATION: (1)..(342)
<223> OTHER INFORMATION: 838.9.4 VH (B4B)

<400> SEQUENCE: 7

```
gaggtgcagc tggaggagtc tctgagactc tcctgtgcaa cttctgggtt caccttcagt    60
gatttctaca tggagtgggt ccgccagcct ccagggaaga gactgagtg gattgctgca    120
agtagaaaca agctaatga ttatacaaca gagtacagtg catctgtgaa gggtcggttc    180
ttcgtctcca gagacacttc ccaaagcatc ctctaccttc agatgaatgc cctgagagct   240
gaggacactg ccatttatta ctgtgcaaga gatgttatga ttacgacggg ggactggtac   300
ttcgatgtct ggggcgcagg gaccacggtc accgtctcct ca                      342
```

<210> SEQ ID NO 8
<211> LENGTH: 318
<212> TYPE: DNA
<213> ORGANISM: Mus musculus
<220> FEATURE:
<221> NAME/KEY: misc_feature
<222> LOCATION: (1)..(318)
<223> OTHER INFORMATION: 838.9.4. VL (p6)

<400> SEQUENCE: 8

```
gacattctga tgacccagtc tcaaaaattc atgtccacat cagtaggaga cagggtcagc    60
gtcacctgca aggccagtca gaatgtgggt actaatgtag cctggtatca acagaaacca   120
```

```
gggcaatctc ctaaagcact gatttactcg gcatcctacc agtacagtgg agtccctgat      180
cgcttcacag gcagtggatc tgggacagat ttcactctca ccatcagcaa tgtgcagtct      240
gaagacttgg cagagtattt ctgtcagcaa tttaacagct atcacgttcg gctcggggac      300
aaagttggaa ttaaaacg                                                    318

<210> SEQ ID NO 9
<211> LENGTH: 375
<212> TYPE: DNA
<213> ORGANISM: Mus musculus
<220> FEATURE:
<221> NAME/KEY: misc_feature
<222> LOCATION: (1)..(375)
<223> OTHER INFORMATION: 476 VH (P10B-TA)

<400> SEQUENCE: 9
gaggtgcagc tggaggagtc tggaggaggc ttggtacagc ctgggggttc tctgagactc       60
tcctgtgcaa cttctgggtt caccttcagt gatttctaca tggagtgggt ccgccagact      120
ccaggggaga gactggagtg gattgctgca agtagaaaca aagctaatga ttatacagca      180
gaatacagtg cgtctgtgaa gggtcgattc accgtcttta gagacacttc ccaaaacatc      240
ctctaccttc agatgaatgc cctgagagct gaagacactg ccgcctatta ctgtgcaaga      300
gatgcggact acggtaaaac cttttcctgg tacttcgatg tctggggcgc agggaccacg      360
gtcaccgtct catca                                                       375

<210> SEQ ID NO 10
<211> LENGTH: 338
<212> TYPE: DNA
<213> ORGANISM: Mus musculus
<220> FEATURE:
<221> NAME/KEY: misc_feature
<222> LOCATION: (1)..(338)
<223> OTHER INFORMATION: 476 VL (F6A*-TA)

<400> SEQUENCE: 10
gatattgtaa tgacccaaga tgaactctcc aatcctgtca cttctggaga atcagttcac       60
atctcctgca ggtctagtaa gagtctccta tataaggatg ggaagacata cttgaattgg      120
tttctgcaga gaccaggaca atcctctcag ctcctgatct atttgatgtc cacccgtgca      180
tcaggagtct cagaccggtt tagtggcagt gggtcaggaa cagatttcac cctgaaaatc      240
agtagagtga aggctgagga tgtgggtgtg tattattgtc aacaacttgt agaatatccg      300
ctcacgttcg gtgctgggac caagctggag ctgaaacg                              338
```

LATERAL FLOW DEVICE FOR DIAGNOSING MICROBIAL INFECTIONS

CROSS-REFERENCE TO RELATED APPLICATIONS

This application claims the benefit of U.S. Provisional Application No. 61/263,498, filed Nov. 23, 2009; which is incorporated herein by reference in its entirety.

FEDERALLY SPONSORED RESEARCH OR DEVELOPMENT

This invention was made in part with United States government support under U01AI54736, R03AI053623, R21AI065745 awarded by the National Institutes of Health. The government has certain rights in the invention.

REFERENCE TO SEQUENCE LISTING SUBMITTED ELECTRONICALLY

The official copy of the Sequence Listing is submitted concurrently with the specification as an ASCII formatted text file via EFS-Web, with a file name of P10606-03_Sequence_Listing_ST25.txt, creation date of Nov. 22, 2010, and with a file size of 5.75 KB. The Sequence Listing filed via EFS-Web is part of the specification and is herein incorporated by reference in its entirety.

BACKGROUND

Currently available, non-culture based diagnostic tests for aspergillosis detect antigens circulating in blood. These tests, which detect β-1,3 glucan (GL) and galactomannan (GM), have variable performance characteristics and require relatively sophisticated and expensive laboratory resources to perform. The sophistication required for laboratory testing and the need for blood draw limit the application of currently available assays such that screening can be performed only infrequently and require health care facilities for phlebotomy and sample processing.

Development of an easy-to-use "point of care" (POC) assay would allow for frequent screening during the period in which a patient is at highest risk for an infection, especially after discharge from a health care facility. Lateral flow devices (LFD), also known as immunochromatographic strip tests, are a common POC testing method. LFDs reduce time spent waiting for test results (from hours to minutes), require less training for operators (thereby enabling user interpretation), and are less expensive both to manufacture and to use.

Fungi, as a group, are polysaccharide-rich organisms, which explains the relative success in the development of antigen-based assays for fungi. Some of these antigens are concentrated in urine. This characteristic, however, has been exploited for developing diagnostics for relatively rare endemic mycoses (e.g. coccidioidomycosis) only.

SUMMARY

In some aspects, the presently disclosed subject matter provides a method for diagnosing a microbial infection in a mammalian subject suspected of having, having, or susceptible to having a microbial infection by detecting the presence of at least one polysaccharide comprising a galactofuranose residue in a biological sample of the mammalian subject, the method comprising: (a) providing a biological sample from the subject; (b) contacting the biological sample with at least one antibody specific for at least one polysaccharide comprising a galactofuranose residue in an effective amount to produce a detectable amount of antibody-polysaccharide complex; and (c) detecting the presence of at least one antibody-polysaccharide complex, wherein the detection of the presence of at least one antibody-polysaccharide complex is diagnostic of a microbial infection in a mammalian subject.

In particular aspects, the microbial infection is caused by an infection of an organism selected from the group consisting of *Streptococcus pneumoniae*, *Aspergillus* species, *Fusarium* species, *Coccidonivcoses* species, *Ctyprococcus* species, and *Histoplasmosis* species. The antibody of the presently disclosed methods is, in some aspects, specific for at least one polysaccharide comprising a galactofuranose residue and is selected from the group consisting of monoclonal antibody 205 (MAb 205) comprising a variable heavy ($V_H$) domain of SEQ ID NO: 1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10. The presently disclosed methods are suitable for use in biological samples selected from the group consisting of urine, bronchoalveolar lavage (BAL) fluid, serum, blood, and cerebrospinal fluid (CSF). In further aspects, the method comprises pre-treating the biological sample, which in particular embodiments is a urine sample, to remove an inhibitor that interferes with the detection of the at least one polysaccharide comprising a galactofuranose residue in the biological sample.

In other aspects, the presently disclosed subject matter provides a lateral flow device adapted to perform the presently disclosed methods for diagnosing a microbial infection in a biological sample of a mammalian subject suspected of having, having, or susceptible to having a microbial infection.

In yet other aspects, the presently disclosed subject matter provides an antibody specific for at least epitope of a polysaccharide secreted by a microbial organism, wherein in particular aspects, the polysaccharide comprises a galactofuranose residue.

In some aspects, the presently disclosed subject matter provides a kit comprising one or more of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6, monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10. Such kits can further comprise a presently disclosed lateral flow device and/or components thereof and, in some aspects, an apparatus adapted for pre-treating the sample and/or instructions for use for diagnosing a microbial infection in a biological sample of a mammalian subject suspected of having, having, or susceptible to having a microbial infection.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
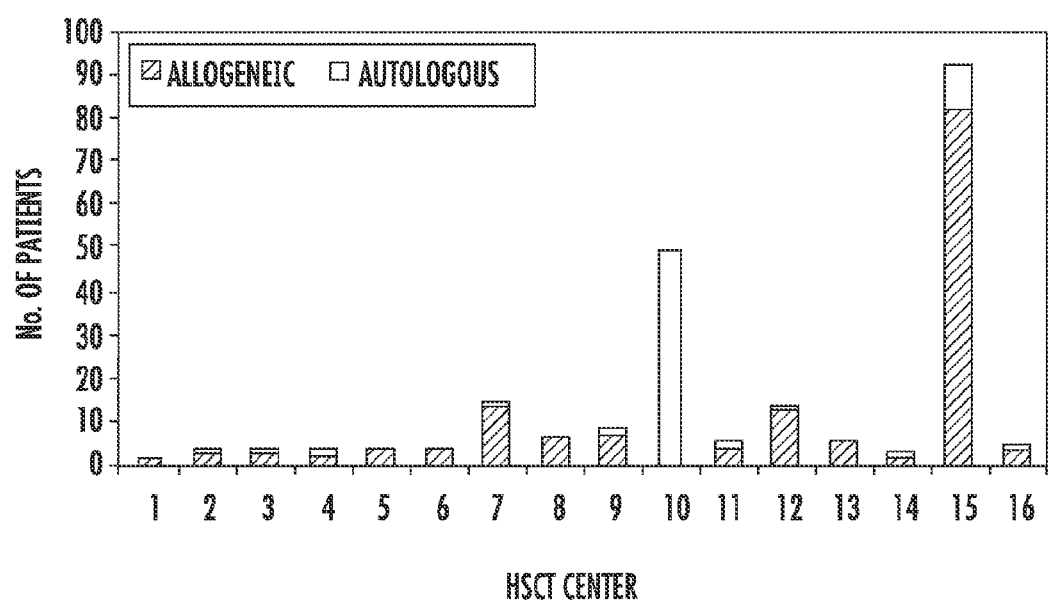
Figure 2:
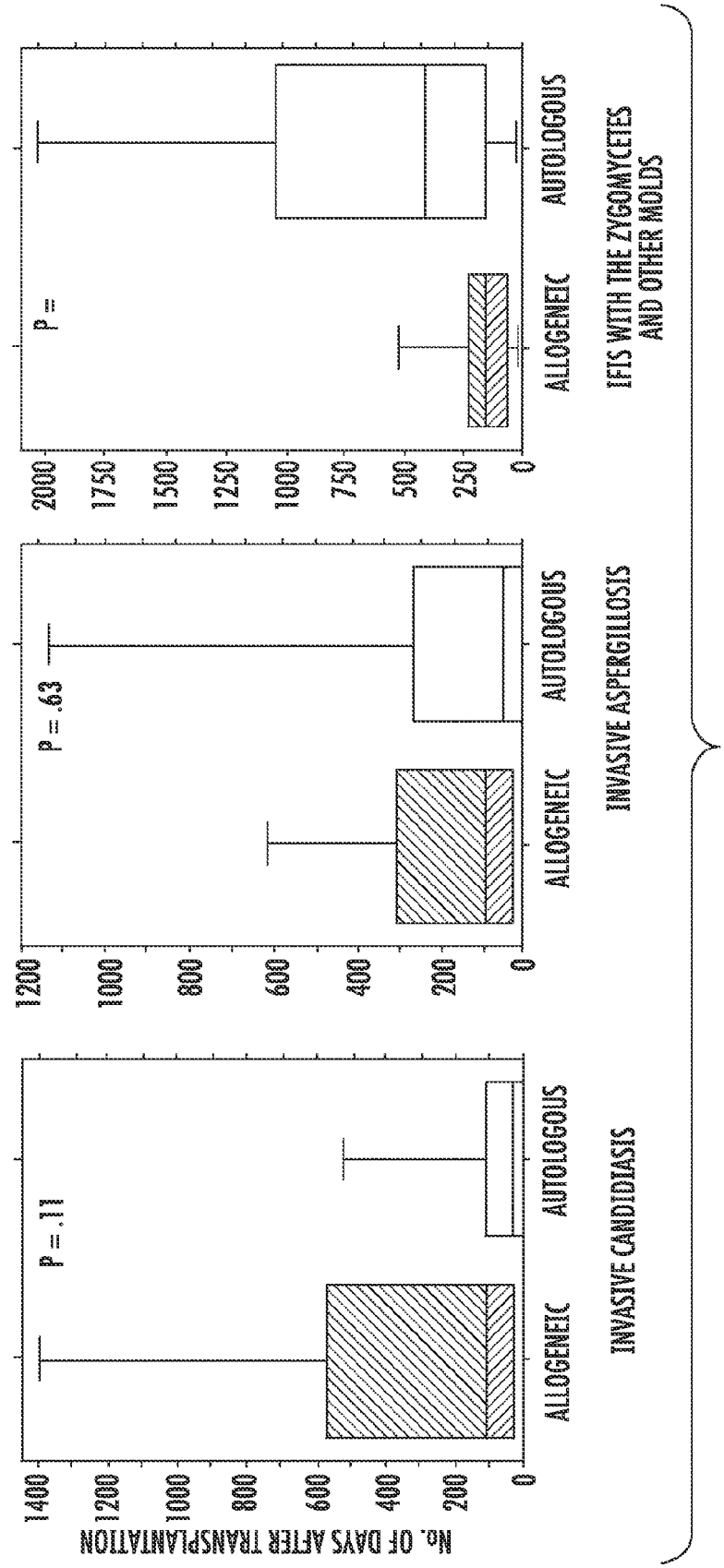

Having thus described the presently disclosed subject matter in general terms, reference will now be made to the accompanying Figures, which are not necessarily drawn to scale, and wherein:

FIG. 1 (prior art) is a chart showing the number of patients contributed by the Prospective Antifungal Therapy (PATH) Alliance participating centers presented on the basis of hematopoietic stem cell transplant (HSCT) category (allogeneic vs. autologous) across 16 transplantation centers;

FIG. 2 (prior art) is a series of charts showing the interval between diagnosis or invasive fungal infection (IF) after hematopoietic stem cell transplantation (HSCT; patients with only one infection were included) for allogeneic versus autologous HSCT recipients. P value is for a comparison of allogeneic and autologous HSCT groups.

Figure 3:
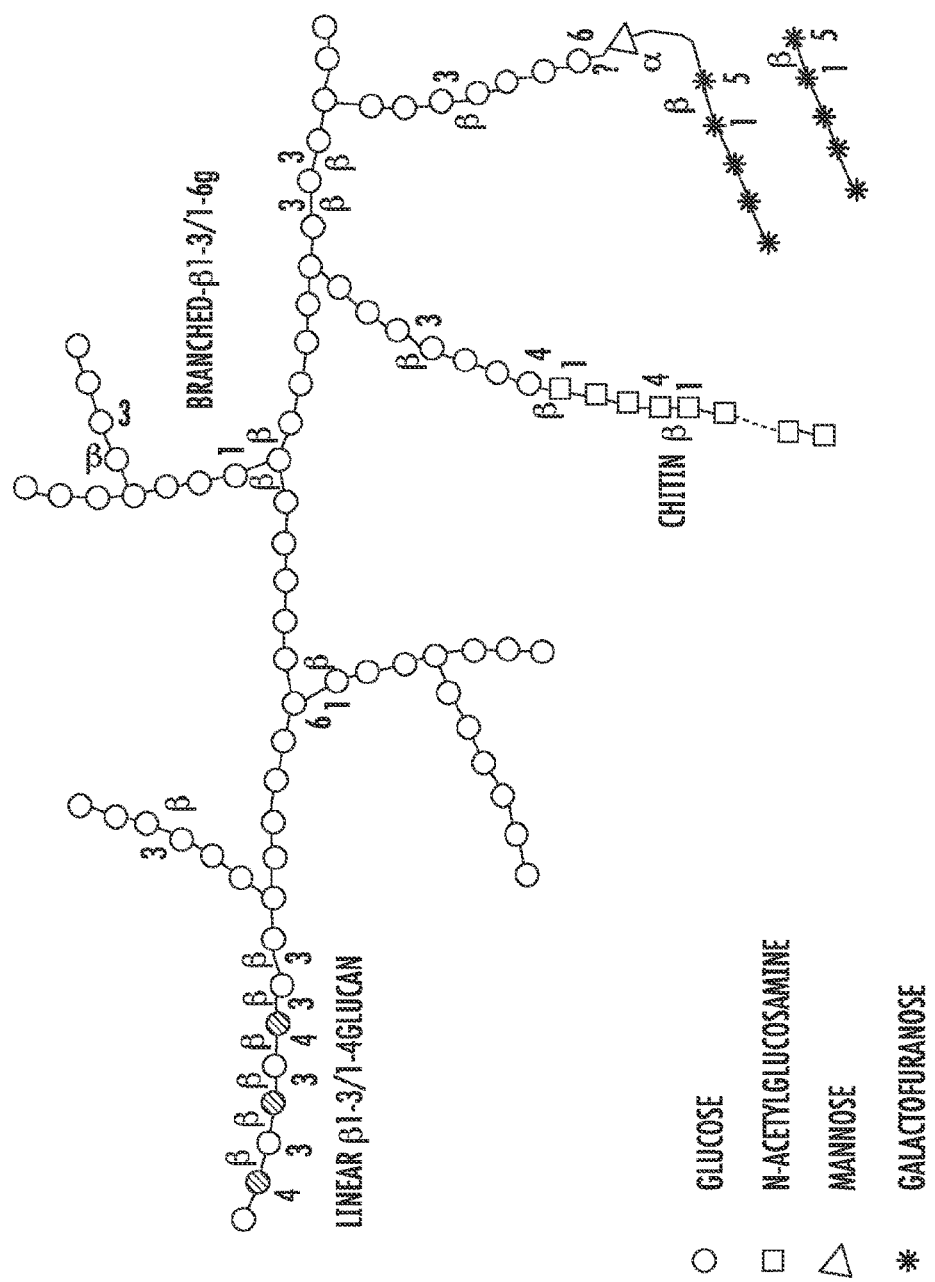
Figure 4:
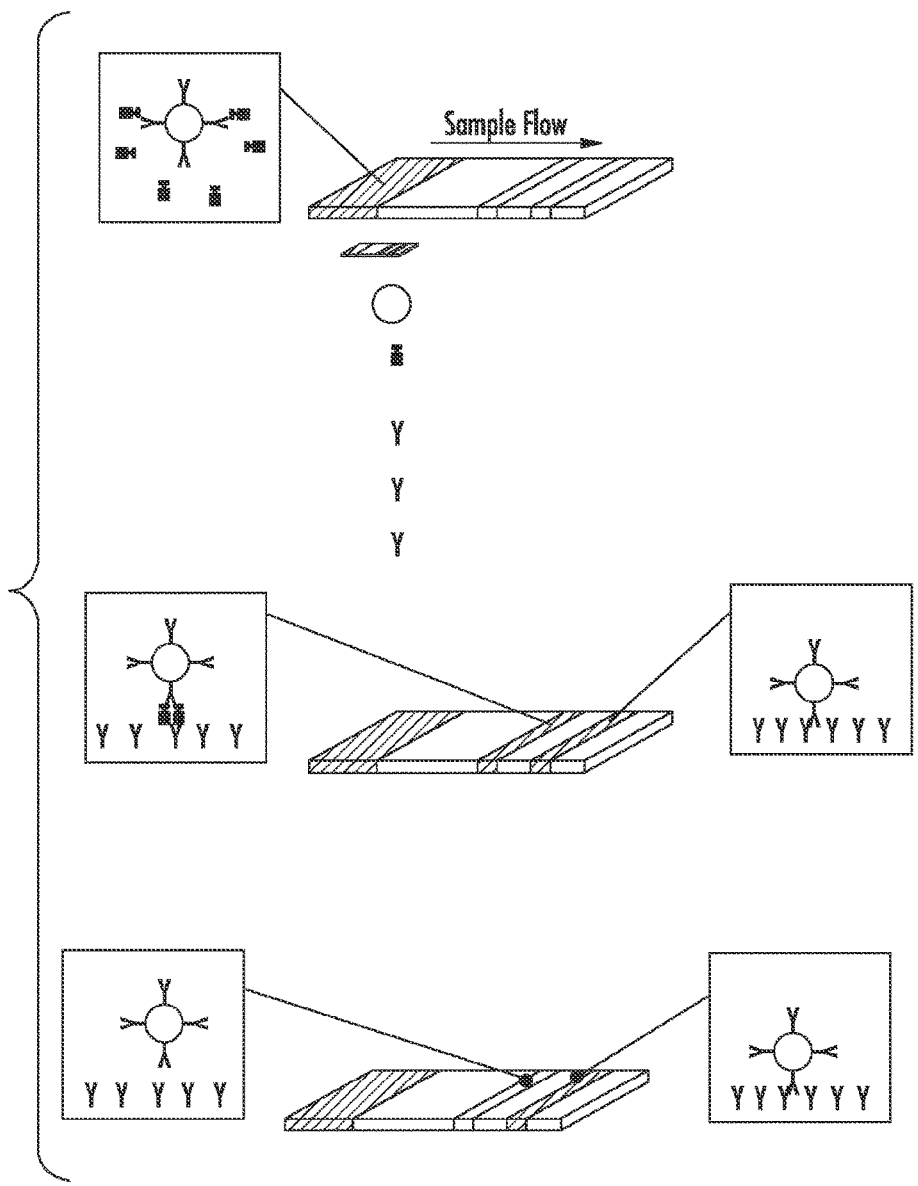
Figure 5:
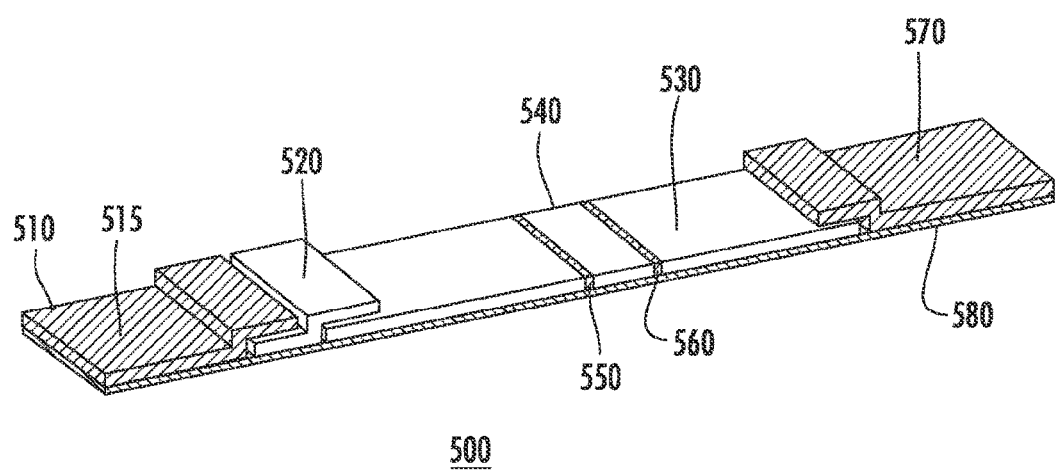
Figure 6:
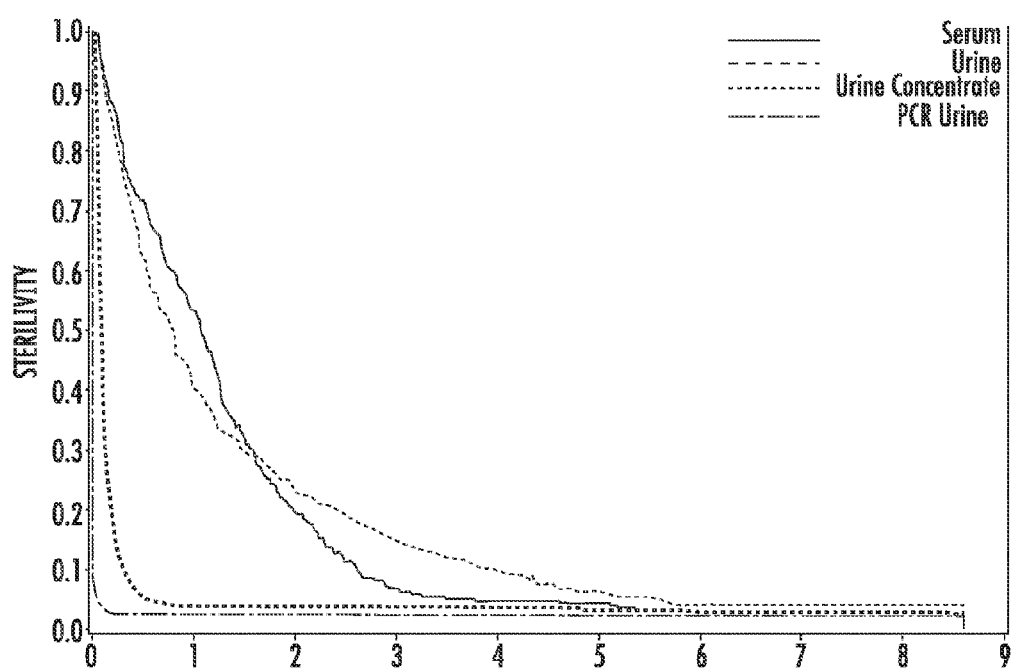
Figure 7:
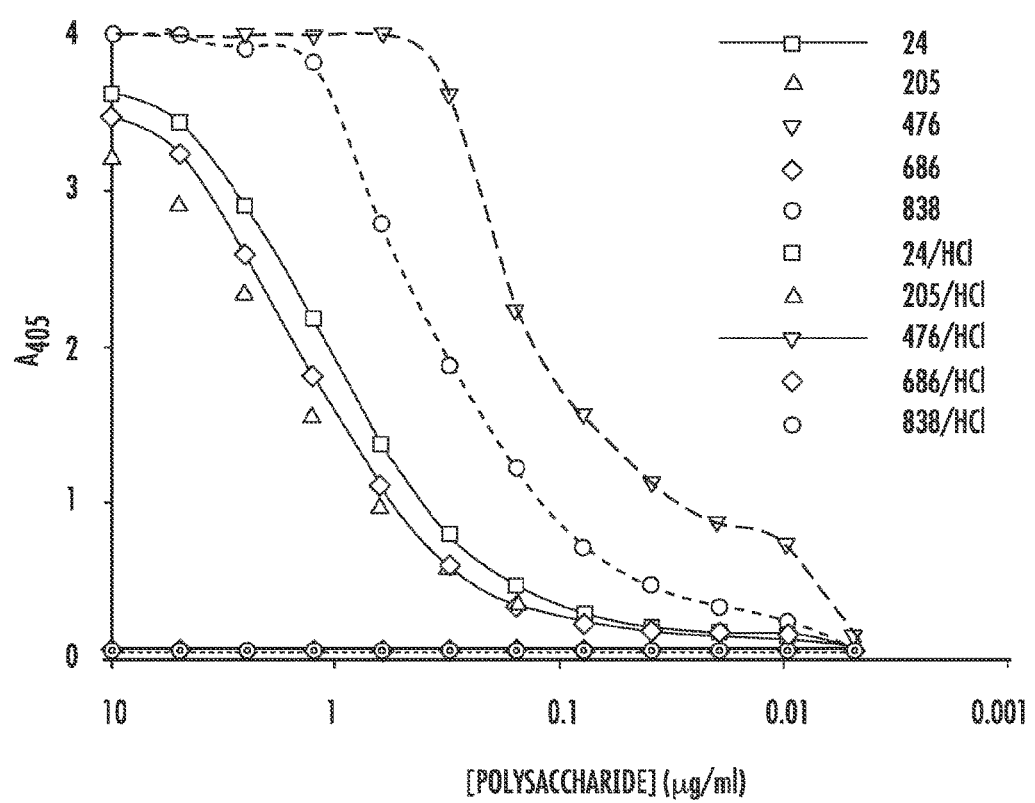
Figure 8A:
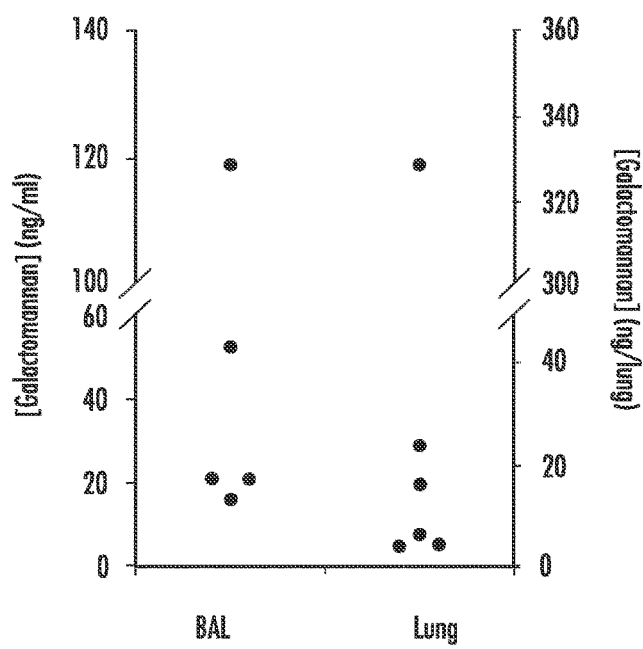
Figure 8B:
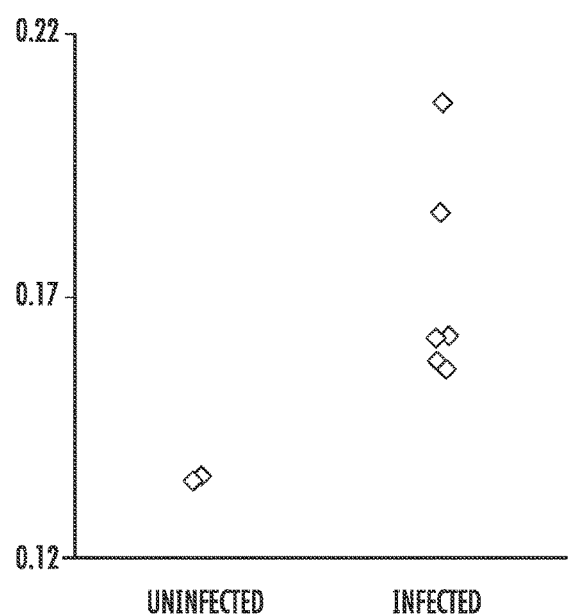
Figure 9:
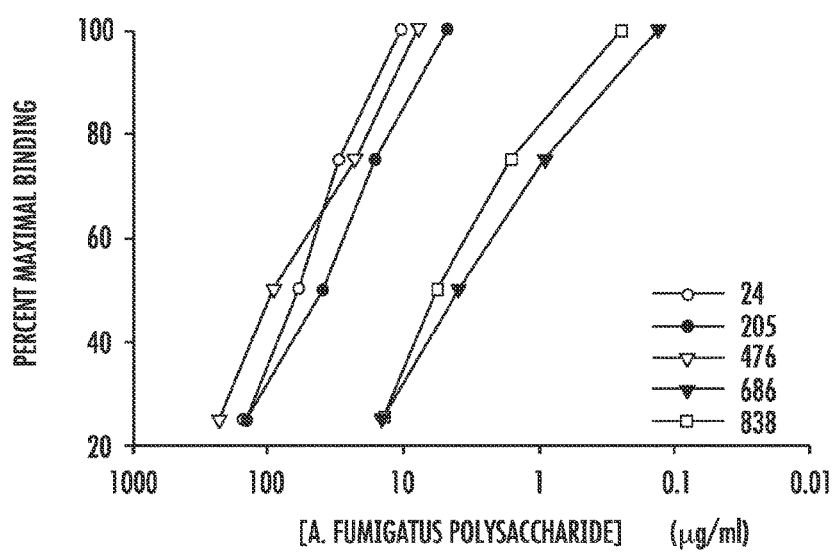
Figure 10:
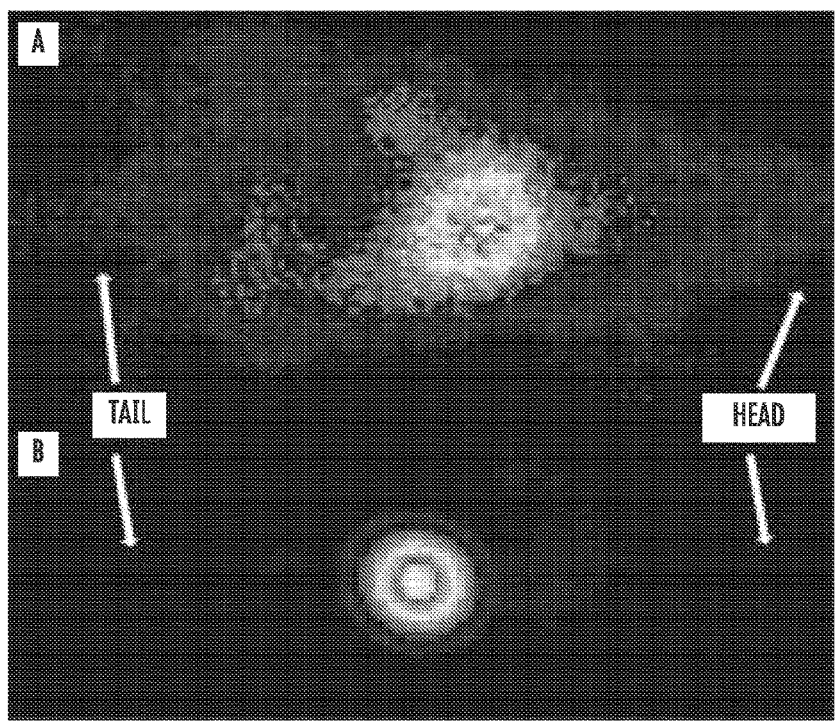
Figure 11:
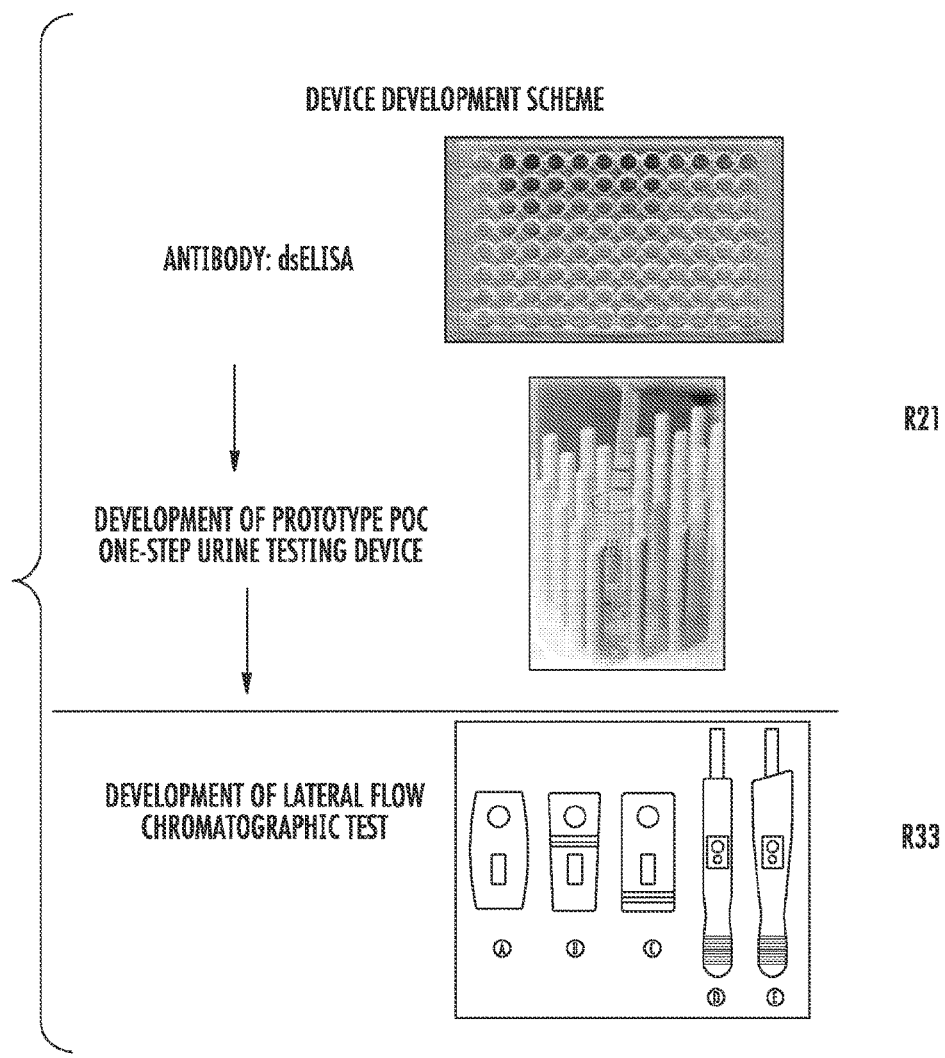
Figure 12:
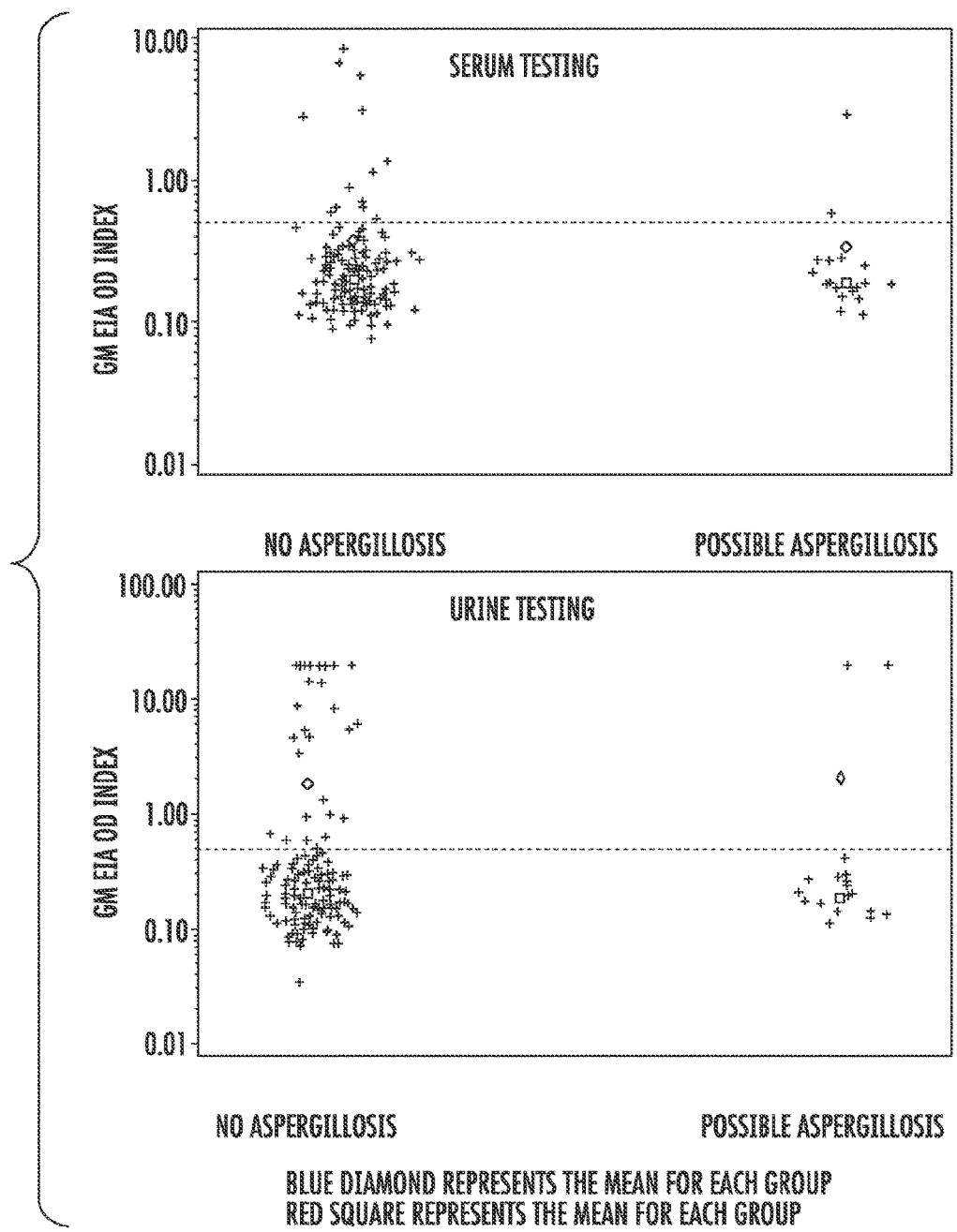
Figure 13:
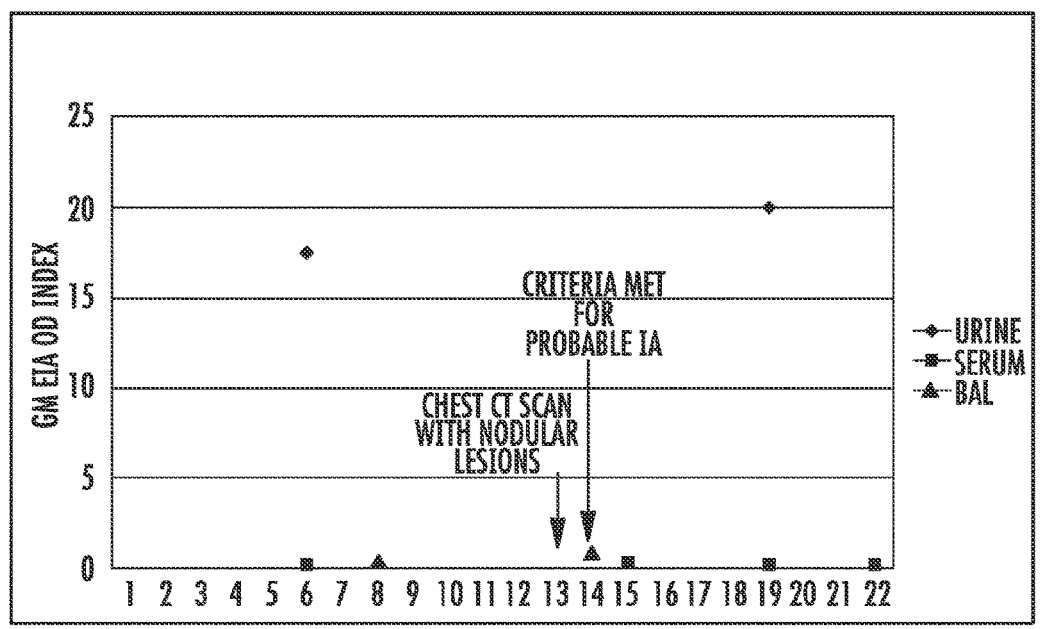
Figure 14:
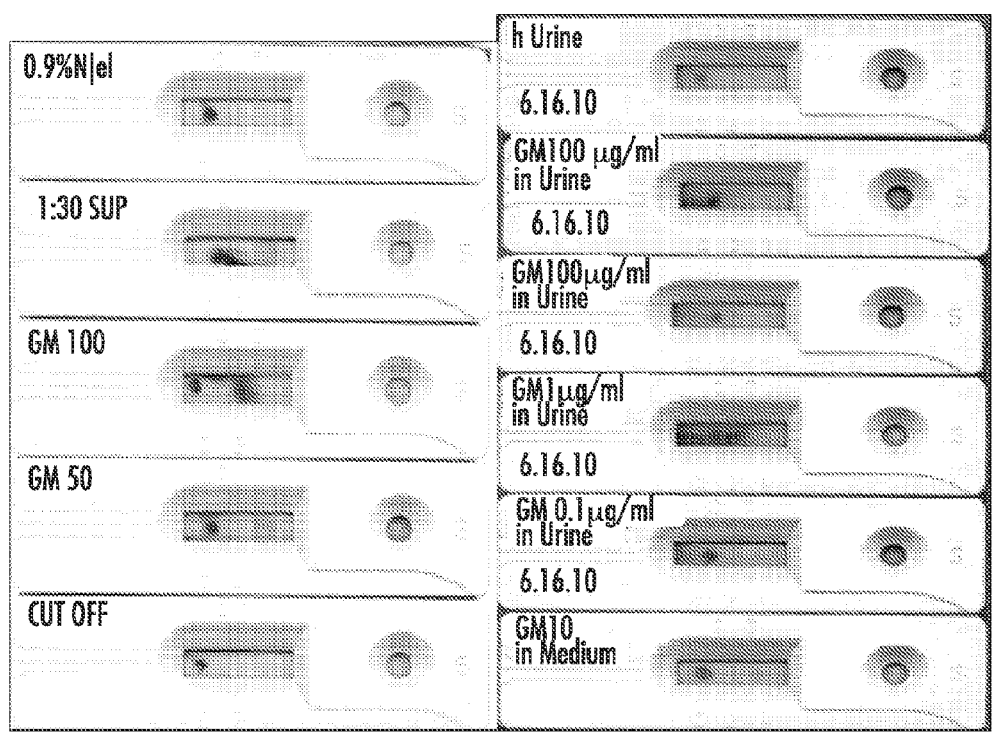
Figure 15:
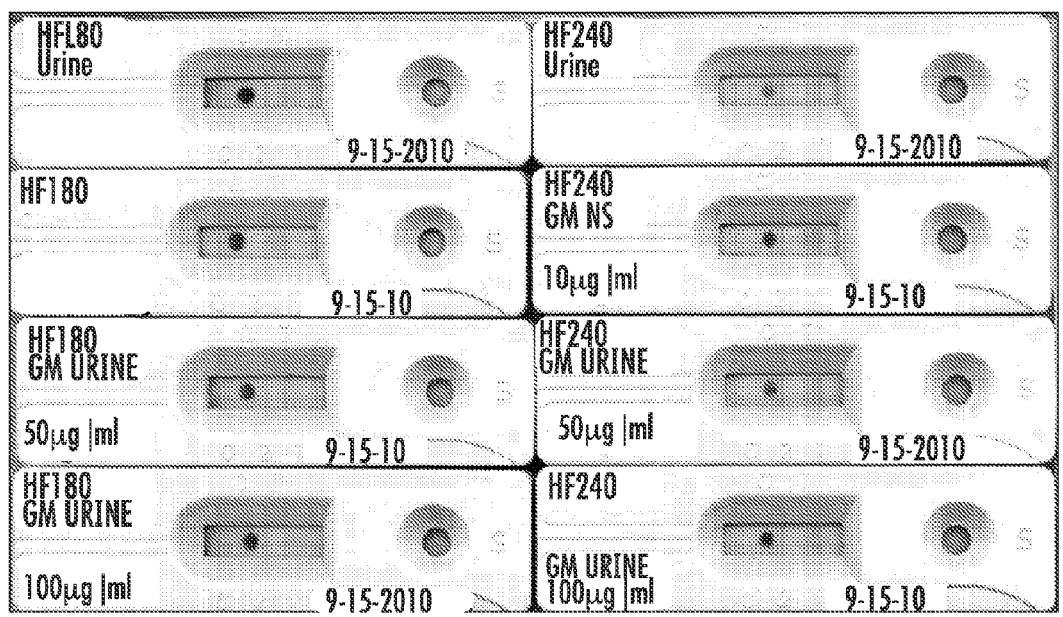
Figure 16:
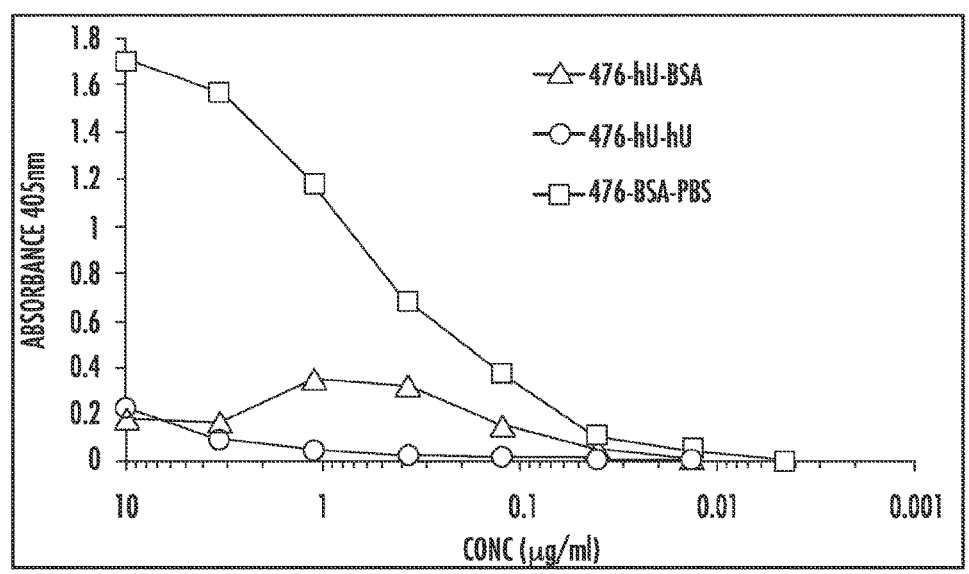
Figure 17:
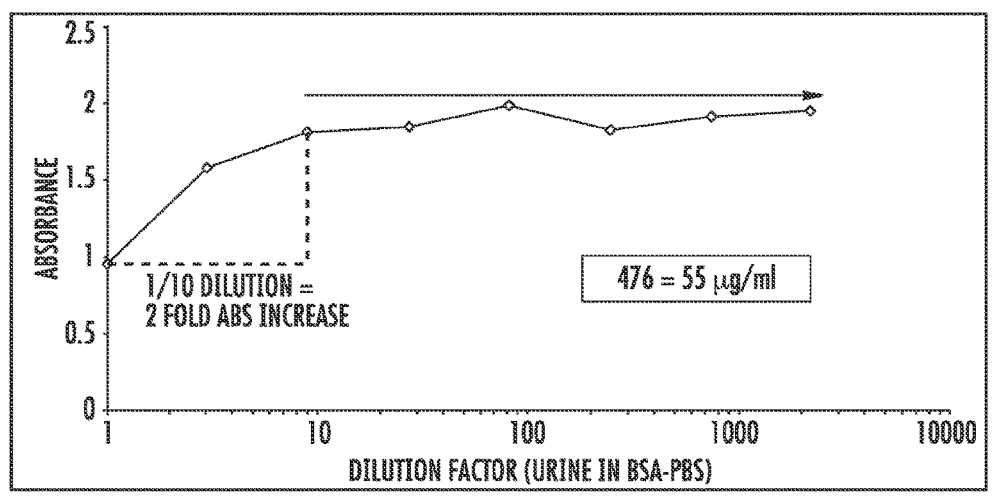
Figure 18:
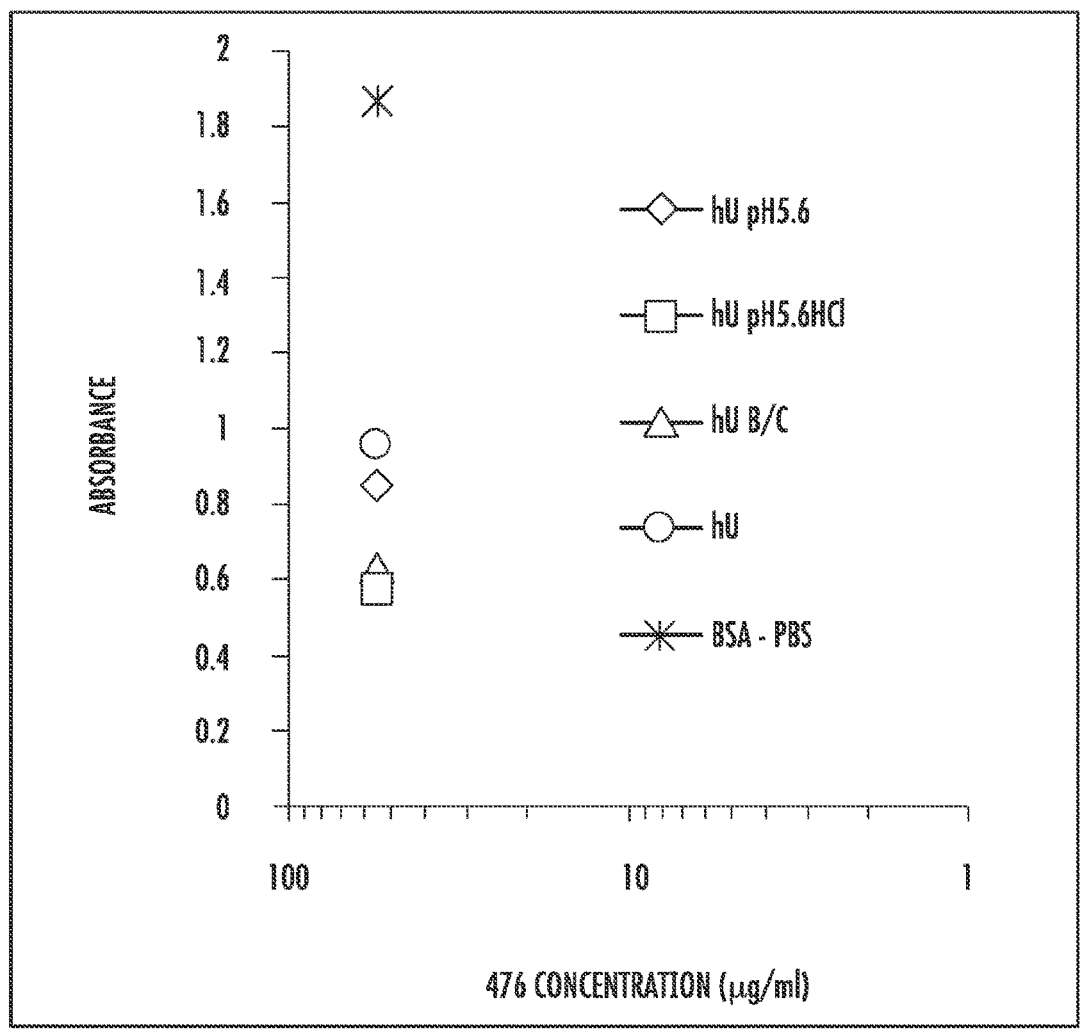
Figure 19:
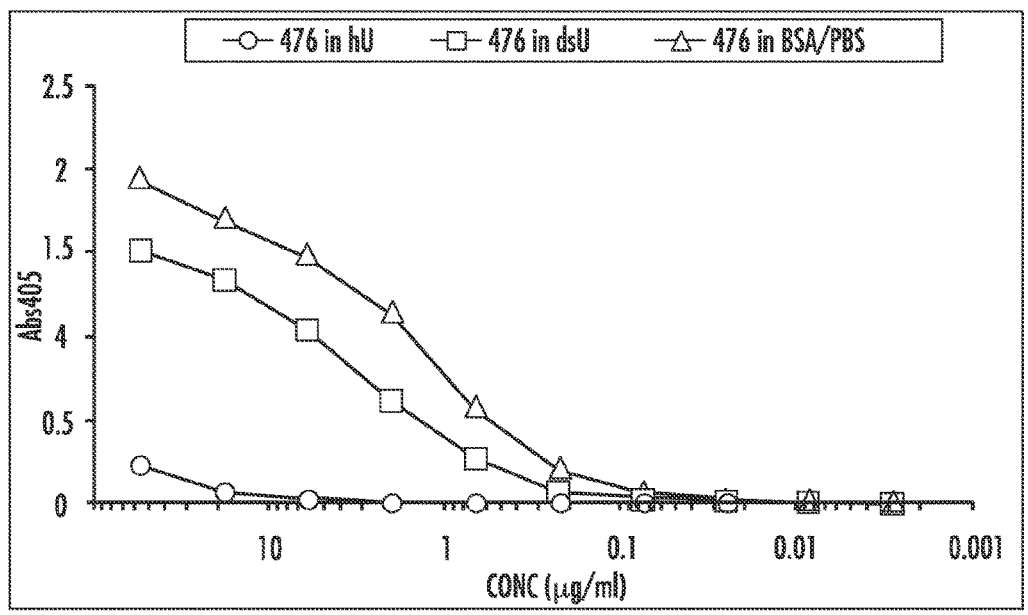
Figure 20:
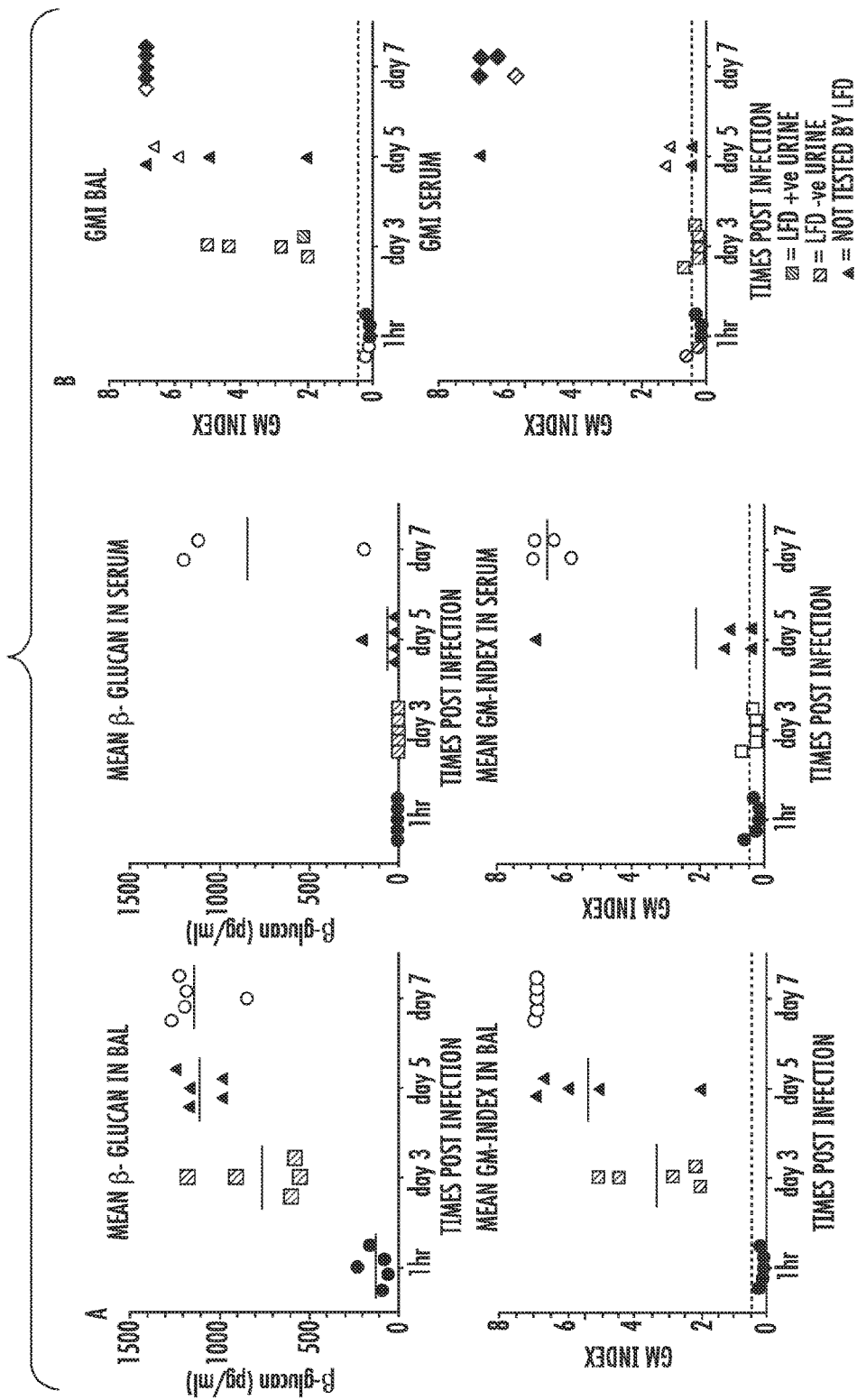

FIG. 3 (prior art) is a graphical depiction of the structure of galactomannan (GM);

FIG. 4 is a schematic diagram depicting a representative embodiment of the presently disclosed lateral flow device illustrating a direct (double antibody sandwich) reaction;

FIG. 5 is a schematic diagram showing a representative embodiment of a lateral flow device;

FIG. 6 is a plot of sensitivity of test (y-axis) according to cut-off value to define positivity;

FIG. 7 is a graph showing binding of MAbs to purified GM or to GM treated with 0.01 N HCl, as determined by ELISA. Loss of binding suggests that the epitopes contain the galactofuranose portion of the molecule, rather than the mannan backbone;

FIG. 8 is a graph showing capture ELISA for galactomannan detection from BAL or lung homogenates of neutropenic mice (top) and serum (bottom) two days after infection with *A. fumigatus*. In uninfected mice, concentrations in both BAL and lung were below the limit of detection. N=5 or 6 for BAL and lung homogenate groups, respectively;

FIG. 9 is a graph showing the relative affinities of GM-binding MAbs. Measurements were made by competition ELISA using soluble ethanol-precipitated culture filtrate. Percent of maximal binding is shown;

FIG. 10 is a gamma camera image showing the distribution of MAb476-Tc99m two days after infection: (A) In sham-infected mice, label is seen in the liver and spleen; and (B) In mice with invasive pulmonary aspergillosis, label is localized in the bladder. N=3 per group in each of two independent experiments;

FIG. 11 is a schematic diagram depicting the development of the presently disclosed lateral flow device;

FIG. 12 provides two graphs showing a comparison of serum and urine GM EIA results for patients with no or possible Aspergillosis;

FIG. 13 is a graph showing the results of serial GM EIA on urine, serum and BAL specimens from a patient with probable IA;

FIG. 14 shows a series of photographs demonstrating a representative, presently disclosed lateral flow device capable of reproducibly identifying a minimal amount of 10 μg/mL GM (in 0.9% NaCl);

FIG. 15 shows a series of photographs demonstrating a representative, presently disclosed lateral flow device capable of detecting purified GM spiked into healthy human urine at 100 μg/mL of antigen in urine;

FIG. 16 is graph showing the sensitivity of the MAb476 antibody for detecting GM in urine and PBS using capture ELISA with a high-flow membrane (240);

FIG. 17 is graph showing the sensitivity of the MAb476 antibody using capture ELISA for detecting GM in urine versus urine diluted in BSA-PBS for a constant antibody-antigen concentration;

FIG. 18 is a graph depicting results from preliminary studies performed to determine if altering the basic properties of urine could increase sensitivity of the reaction in capture ELISA;

FIG. 19 is a graph demonstrating that pre-treating urine by filtration through a desalting column results in an improvement of sensitivity of the MAb476 antibody for detecting GM in urine, such that the sensitivity of the test in urine was approximately equivalent to that of BSA-PBS; and FIGS. 20A-B show the GM and β-glucan index values and concentrations, respectively, over time of BAL and serum from guinea pigs infected with Af293.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Current Methods for Diagnosing Microbial Infections in Biological Samples

It has been previously reported that galactomannan, or an antigen that shares a cross-reactive epitope identified by the antibody EBA1/EBA2, is excreted in urine in rabbits and humans infected with *Aspergillus* species. See Klont, R. R., M. A. Mennink-Kersten, and P. E. Verweij, *Utility of Aspergillus antigen detection in specimens other than serum specimens*. Clin Infect Dis, 2004. 39(10): p. 1467-74; Dupont, B., et al., *Galactomannan antigenemia and antigenuria in aspergillosis: studies in patients and experimentally infected rabbits*. J Infect Dis, 1987. 155(1): p. 1-11; Bennett, J. E., M. M. Friedman, and B. Dupont, *Receptor-mediated clearance of Aspergillus galactomannan*. J Infect Dis, 1987. 155(5): p. 1005-10; Rogers, T. R., K. A. Haynes, and R. A. Barnes, *Value of antigen detection in predicting invasive pulmonary aspergillosis*. Lancet, 1990. 336(8725): p. 1210-3; Ansorg, R., E. Heintschel von Heinegg, and P. M. Rath, *Aspergillus antigenuria compared to antigenemia in bone marrow transplant recipients*. Eur J Clin Microbiol Infect Dis, 1994. 13(7): p. 582-9; Salonen, J., et al., *Aspergillus antigen in serum, urine and bronchoalveolar lavage specimens of neutropenic patients in relation to clinical outcome*. Scandinavian Journal of Infectious Diseases, 2000. 32: p 485-490. No diagnostic assay for *Aspergillus* species currently relies on detection of an antigen in urine, however, and no large studies have been performed to determine the utility of urinary antigen testing for *Aspergillus* species.

A. Background

1. Diseases Caused by *Aspergillus* Species

*Aspergillus* spp. are exogenously acquired into the lungs. The organism grows in a sporulating phase in the environment, in which asexual reproduction yields small, hydrophobic, readily aerosolized, ubiquitous conidia. Disease occurs when conidia that are inhaled into the lungs escape phagocytosis and germinate into angioinvasive hyphae. Clinical manifestations arise both from microbial invasion and from aberrant inflammatory responses, creating a spectrum of allergic, saprophytic, semi-invasive, and invasive manifestations. As the organism might not be circulating in blood at the time of pulmonary disease, especially in non-neutropenic hosts, development of blood-based diagnostics requires a platform that can detect biomarkers without necessitating circulating cells. Fortunately, many fungi, including *Aspergillus* species, secrete polysaccharides or other metabolites during growth, enabling detection of these products prior to actual blood stream invasion. For instance, absorption of the galactoxylomannan (GXM) polysaccharide of *Cryptococcus* neoformans capsules occurs well before the organism is blood-borne; hence, the diagnostic test that relies on detection of this antigen is sensitive and provides 'early' diagnostic results.

2. Epidemiology and Approach to Fungal Infections

During the 1990's, a marked change occurred in the opportunistic infections that occur in patients with hematologic malignancies and in recipients of HCT, largely because of effective prevention of infection caused by cytomegalovirus (CMV) and *Candida albicans*. Early studies validated the use of ganciclovir administered preemptively in the setting of pp65 antigenemia to prevent CMV disease, Boeckh, M., et al., *Successful modification of a pp65 antigenemia-based early treatment strategy for prevention of cytomegalovirus disease in allogeneic marrow transplant recipients*. Blood, 1999. 93(5): p. 1781-2; Boeckh, M., T. Gooley, and R. Bowden, *Effect of high-dose acyclovir on survival in allogeneic marrow transplant recipients who received ganciclovir at engraftment or for cytomegalovirus pp65 antigenemia*. J Infect Dis, 1998. 1998(178): p. 1153-7; Boeckh, M., et al., *Plasma polymerase chain reaction for cytomegalovirus DNA after allogeneic marrow transplantation: comparison with polymerase chain reaction using peripheral blood leukocytes, pp65 antigenemia, and viral culture*. Transplantation, 1997. 64: p. 108-113; Boeckh, M., et al., *Cytomegalovirus pp65 antigenemia-guided early treatment with ganciclovir versus ganciclovir at engraftment after allogeneic marrow transplantation: a randomized double-blind study*. Blood, 1996. 88(10): p. 4063-4071, and the utility of prophylactic fluconazole for preventing candidiasis. Slavin, M. A., et al., *Efficacy and safety of fluconazole prophylaxis for fungal infections after marrow transplantation—a prospective, randomized, double-blind study*. Journal Of Infectious Diseases., 1995. 171(6): p. 1545-52. Subsequent independent analyses of transplant outcomes showed that two variables associated with survival after HCT for chronic myelogenous leukemia were receipt of ganciclovir and fluconazole. Hansen, J. A., et al., *Bone marrow transplants from unrelated donors for patients with chronic myeloid leukemia*. The New England Journal of Medicine, 1998. 338: p. 962-8. These studies demonstrate that prevention of infection is a critical component in improving the overall outcomes of transplant and cancer chemotherapy. Hence, attempts to improve outcomes should be focused not only on establishing methods for early diagnosis, but also on developing methods to enable targeted prevention.

Unfortunately, successful prevention of infection has been limited by the emergence of pathogenic moulds, particularly *Aspergillus* species. A review of aspergillosis at the Fred Hutchinson Cancer Research Center (FHCRC) between 1987 and 1993 showed that the incidence of infection increased during the first six months of 1993. More recent studies showed that the overall incidence of infection tripled over the last decade, such that this infection now accounts for 10-20% of deaths in allogeneic HCT recipients. Marr, K., et al., *Epidemiology and outcome of mould infections in hematopoietic stem cell transplant recipients*. Clin Infect Dis, 2002. 34: p. 909-917; Wald, A., et al., *Epidemiology of Aspergillus infections in a large cohort of patients undergoing bone marrow transplantation*. The Journal of Infectious Diseases, 1997. 175: p. 1459-66.

Reported incidences vary, however, largely due to diagnostic biases and differences in aggressiveness in establishing infection vs. treating presumptively. For example, a recent multicenter study shows that the incidence of aspergillosis in both autologous and allogeneic HCT recipients varies per center, with some centers reporting a very high number of cases, and other centers reporting few to no recognized infections (FIG. 1) (prior art). Neofytos, D., et al., *Epidemiology and outcome of invasive fungal infection in adult hematopoietic stem cell transplant recipients: analysis of Multicenter Prospective Antifungal Therapy (PATH) Alliance registry*. Clin Infect Dis, 2009. 48(3): p. 265-73. The majority of cases of aspergillosis occur late after transplant during the non-neutropenic period in association with severe GVHD and corticosteroid use, with a median of approximately 82 days in recipients of allogeneic HCT. Surprisingly, even recipients of autologous grafts now develop IA late after HCT, at a median of 51 days after HCT (FIG. 2). The range of days at IA diagnosis is extremely broad; in this most recent multicenter study, IA diagnoses ranged from day 0 to day 6,542 after receipt of stem cells.

Invasive fungal infections caused by other moulds occur yet later after allogeneic and autologous HCT (FIG. 2). Timing of infection relative to HCT and the increased duration of risk well beyond that of neutropenia complicates development of preventative strategies, as any effective regimen would require either long-term administration of a drug or frequent monitoring in the outpatient setting (or both). The trend to late development of IA also applies to patients at risk for infection by virtue of receipt of solid organ transplantation (SOT). In the same multicenter cohort evaluated for epidemiology and outcomes of IA cited above, which summarized invasive fungal infections in 429 SOT recipients in 17 U.S. centers (PATH alliance), it was documented that IA occurs well beyond discharge after transplantation in liver, lung, and heart transplant recipients, at a median of 100 days (range 10, 146), 504 days (range 3, 417) and 382 days (range 31, 309) after transplantation. Neofytos et al, *Epidemiology and outcome of invasive fungal infections in solid organ transplant recipients*. Transpl Infect Dis, 2010. 12(3): p. 220-9. Hence, results of recent single-center and multi-center epidemiology studies demonstrate that fungal infections, especially those caused by *Aspergillus* species, typically occur late after immunosuppressive procedures, such as transplant, and with unpredictable timing. Accordingly, establishing methods to prevent advanced disease and to diagnose IA early will require more than optimization of assay performance parameters, but also will require a strategy, such as POC testing, that can be employed effectively in an outpatient setting.

3. Diagnosis of Pathogenic Fungal Infections: An Overview

Invasive fungal infections are notoriously difficult to diagnose, in part because the organisms are difficult to cultivate in the laboratory. This difficulty is secondary to multiple factors, including growth of the organism in morphologies that do not replicate by simple binary fission, and requirements for alternative growth conditions in the laboratory. Also, it can be difficult to obtain adequate tissue samples from the most frequently involved site, i.e., the lungs, without inducing excessive morbidity. Adjunctive diagnostic tests have been developed and are in common use, however, for multiple fungal infections, including cryptococcosis and infections caused by multiple endemic fungi (e.g., histoplasmosis and coccidiomycosis), which are frequently diagnosed by using immunoassays that detect fungal polysaccharide antigens in blood, urine, or other fluids, such as cerebral spinal fluid. For example, new tests that detect *Histoplasma*, *Blastomyces*, and *Coccidioides* galactomannans in urine have been developed and appear to have utility in early diagnosis of disease. Durkin, M., et al., *Diagnosis of coccidioidomycosis with use of the Coccidioides antigen enzyme immunoassay*. Clin Infect Dis, 2008. 47(8): p. e69-73; Spector, D., et al., *Antigen and antibody testing for the diagnosis of blastomycosis in dogs*. J Vet Intern Med, 2008. 22(4): p. 839-43.

It is not a coincidence that the most successful adjunctive assays in use today detect fungal polysaccharides, as these organisms characteristically have large, complex polysaccharide-rich cell walls that serve both to present antigens and to complicate detection of intracellular components. In some organisms, such as *Cryptococcus* species, polysaccharides associated with the cellular capsule (e.g., glucuronoxylomannan) are released and absorbed in vivo, facilitating detection in peripheral compartments.

Development of successful diagnostic tests that detect nucleic acids, which has been more successfully employed for viral infections, has been more elusive for fungi despite worldwide efforts. In part, this difficulty is due to the complexities of harvesting nucleic acids from fungal cells, presence of multiple genomes within multicellular filamentous organisms, and unreliable 'release' of nucleic acids from local compartments (lung) into systemic circulation.

4. Current Methods to Diagnose Aspergillosis

Therapeutic advances for aspergillosis have been limited, in part because diagnoses of aspergillosis often are not established until development of radiographic abnormalities, which usually occurs late in the development of an infection given the nonspecific nature of clinical symptoms. Prevention of aspergillosis now constitutes one of the largest critical needs for supportive care. Establishment of successful prevention and therapeutic strategies is contingent on developing better methods to guide therapy.

Multiple platforms exist to detect circulating fungal elements, with most platforms relying on detection of polysaccharide antigens or nucleic acids. Performance of the GM EIA and GL tests is good, but variable, and each test has its own strength and limitation when applied to both serum and bronchoalveolar lavage (BAL). Studies have focused on optimizing assay performance as an aid to diagnosis. No studies, however, have attempted to develop these technologies into platforms more amenable to point-of-care testing. Given the increased incidence of IA occurring outside of the hospital, point-of-care testing is essential to detect early disease.

Current methods for diagnosing IA rely on radiographic detection of "suggestive" abnormalities. Early in the course of IA, the most frequent abnormal findings are nodular lesions, which may, or may not, be surrounded by a hypodense "halo" corresponding to local hemorrhage inflicted by angioinvasive hyphae. Kim, Y., et al., *Halo sign on high resolution CT: findings in spectrum of pulmonary diseases with pathologic correlation*. J Comput Assist Tomogr, 1999. 23(4): p. 622-6. As the lesion progresses in a host that has some degree of coordinated immune response, the lesion will cavitate, creating the "air-crescent" sign. Unfortunately, these radiographic abnormalities occur relatively late in the development of disease. Although one study documented that screening with CT scans might allow for earlier diagnoses, Caillot, D., et al., *Improved management of invasive aspergillosis in neutropenic patients using early thoracic computed tomographic scan and surgery*. Journal of Clinical Oncology, 1997. 15(1): p. 139-147, routine CT's are costly and not a feasible option for the entire period of time during which patients are at risk, for example after they are discharged from a health care facility and are at home.

Other problems with current diagnostic methods are the insensitivity of tissue culture for filamentous fungi and adverse events inflicted by invasive procedures. The microbiologic yield of bronchoalveolar lavage (BAL) approximates only 60% and depends on the nature of the radiographic lesion and the expertise of the microbiology laboratory. Levy, H., et al., *The value of bronchoalveolar lavage and bronchial washings in the diagnosis of invasive pulmonary aspergillosis*. Respir Med, 1992. 86(3): p. 243-8. A review of 214 patients who developed IA after receiving HCT in one center found that only 77% of cases were recognized pre-mortem. Wald, A., et al., *Epidemiology of Aspergillus infections in a large cohort of patients undergoing bone marrow transplantation*. The Journal of Infectious Diseases, 1997. 175: p. 1459-66. The histopathologic and microbiologic yield of biopsies achieved with an open procedure or percutaneously is variable and also results in frequent bleeding complications, especially in children. Hoffer, F. A., et al., *Accuracy of percutaneous lung biopsy for invasive pulmonary aspergillosis*. Pediatr Radiol, 2001. 31(3): p. 144-52.

In summary, new methods are required to meet two clinical needs: (1) to develop sensitive tests that can be used for screening to detect infection early, thereby allowing for effective preventative algorithms; and (2) to increase the sensitivity of detection of fungi when used in adjunct with standard histopathologic and microbiologic techniques (as an aid to diagnosis). The two primary methods that have been explored for these indications rely on detection of fungal antigen(s) or nucleic acids using immunoassays or polymerase chain reaction (PCR), respectively.

i. Antigen Detection

Galactomannan: Galactomannan (GM), a complex of polysaccharide cell wall components that are secreted from growing *Aspergillus* hyphae, is the basis for multiple diagnostic tests. de Sevaux, R. G., et al., *Microgranulomatous aspergillosis in a patient with chronic granulomatous disease: cure with voriconazole*. Clin Infect Dis, 1998. 26(4): p. 996-7, (FIG. 3). Development of a diagnostic test that relies on detection of GM was pioneered in European laboratories and assay systems evolved over multiple decades from relatively insensitive latex agglutination tests to more sensitive enzyme immunoassays (EIAs). de Sevaux, R. G., et al., *Micrograulomatous aspergillosis in a patient with chronic granulomatous disease: cure with voriconazole*. Clin Infect Dis, 1998. 26(4): p. 996-7. An *Aspergillus* EIA (Bio-Rad Platelia, referred to herein as the GM EIA) was the first fungal diagnostic assay approved for commercial use in the United States. Laboratory and clinical studies were performed that led to clearance and in optimizing clinical performance of this serum-based test. Marr, K. A., et al., *Detection of galactomannan antigenemia by enzyme immunoassay for the diagnosis of invasive aspergillosis: variables that affect performance*. J Infect Dis, 2004. 190(3): p. 641-9; Upton, A., et al., *Reproducibility of low galactomannan enzyme immunoassay index values in multiple laboratories*. J Clin Microbiol, 2005. 43(9); p. 4796-4800; Marr, K. A., *Aspergillus galactomannan index: a surrogate end point to assess outcome of therapy?* Clin Infect Dis, 2008. 46(9): p. 1423-5; Sheppard, D. C., et al., *Comparison of three methodologies for the determination of pulmonary fungal burden in experimental marine aspergillosis*. Clin Microbiol Infect. 2006. 12(4): p. 376-80; Upton, A., W. Leisenring, and K. A. Marr, (1→3) *beta-D-glucan assay in the diagnosis of invasive fungal infections*. Clin Infect Dis, 2006. 42(7): p. 1054-6; author reply 1056; Marr, K. A. and W. Leisenring, *Design issues in studies evaluating diagnostic tests for aspergillosis*. Clin Infect Dis, 2005. 41 Suppl 6: p. S381-6; Marr, K. A., et al., *Antifungal therapy decreases sensitivity of the Aspergillus galactomannan enzyme immunoassay*. Clin Infect Dis, 2005. 40(12): p. 1762-9; Mosher, B., et al., *Aspergillus galactomannan enzyme immunoassay and quantitative PCR for diagnosis of invasive aspergillosis with bronchoalveolar lavage fluid*. J Clin Microbiol, 2004. 42(12): p. 5517-22. Data generated in an initial study were presented to the FDA for test clearance. Marr, K. A., et al., *Detection of galactomannan antigenemia by enzyme immunoassay for the diagnosis of invasive aspergillosis: variables that affect performance*. J Infect Dis, 2004. 190(3): p. 641-9. Multiple other studies have since been performed that have increased knowledge concerning diagnosis. In part, these studies established that the GM molecule, or an antigen presenting an epitope recognized by the EBA2 antibody, is concentrated in urine.

The GM EIA is a one-stage immunoenzymatic sandwich microplate assay that incorporates the β-1-5 galactofuranose-specific EBA2 monoclonal antibody as both acceptor and detector for GM. Stynen, D., et al., *Rat monoclonal antibodies against Aspergillus galactomannan*. Infect Immun, 1992. 60: p. 2237-2245. This double sandwich EIA, which has improved sensitivity compared to prior assays (1.0 ng GM per mL of serum), was available in European centers for multiple years before availability in the U.S. Reported sensitivity and specificity have been variable, ranging from 57 to 100% and 66 to 100%, respectively. Boeckh, M., et al., *Cytomegalovirus pp65 antigenemia-guided early treatment with ganciclovir versus ganciclovir at engraftment after allogeneic marrow transplantation: a randomized double-blind study*. Blood, 1996. 88(10): p. 4063-4071; Slavin, M. A., et al., *Efficacy and safety of fluconazole prophylaxis for fungal infections after marrow transplantation—a prospective, randomized, double-blind study*. Journal Of Infectious Diseases., 1995. 171(6): p. 1545-52; Marr, K. A. and W. Leisenring, *Design issues in studies evaluating diagnostic tests for aspergillosis*. Clin Infect Dis, 2005. 41 Suppl 6: p. S381-6; Klont, R. R., M. A. Mennink-Kersten, and P. E. Verweij, *Utility of Aspergillus antigen detection in specimens other than serum specimens*. Clin Infect Dis, 2004. 39(10): p. 1467-74; Ansorg, R., E. Heintschel von Heinegg, and P. M. Rath, *Aspergillus antigenuria compared to antigenemia in bone marrow transplant recipients*. Eur J Clin Microbiol Infect Dis, 1994. 13(7): p. 582-9; Dupont, B., et al., *Galactomannan antigenemia and antigenuria in aspergillosis: studies in patients and experimentally infected rabbits*. J Infect Dis, 1987. 155(1): p. 1-11; Ellis, M., et al., *Assessment of the clinical utility of serial beta-D-glucan concentrations in patients with persistent neutropenic fever*. J Med Microbial, 2008. 57(Pt 3): p. 287-95; Koide, M., et al., *Comparative evaluation of Duopath Legionella lateral flow assay against the conventional culture method using Legionella pneumophila and Legionella anisa strains*. Jpn J Infect Dis, 2007. 60(4): p. 214-6; Kappe, R. and A. Schulze-Berge, *New cause for false-positive results with the Pastorex Aspergillus antigen latex agglutination test*. J Clin Microbiol, 1993. 31(9): p. 2489-90; Stynen, D., et al., *Rat monoclonal antibodies against Aspergillus galactomannan*. Infect Immun, 1992. 60(6): p. 2237-45.

Multiple explanations have been posed for this variability, including limitations in retrospective study designs, small sample sizes, variable criteria to establish diagnoses, and variable numbers of sera sampled in patients. Perhaps most importantly, these studies were performed in centers that allowed concomitant clinical application of the test, as administration of antifungals impacts ability to define performance parameters because of the lack of true controls. In several studies, it was found that mould-active antifungal drugs function to suppress sensitivity of the GM EIA, perhaps by decreasing the amount of circulating antigen or fungus itself. Marr, K. A., et al., *Detection of galactomannan antigenemia by enzyme immunoassay for the diagnosis of invasive aspergillosis: variables that affect performance*. J Infect Dis, 2004. 190(3): p. 641-9: Marr, K. A., et al., *Antifungal therapy decreases sensitivity of the Aspergillus galactomannan enzyme immunoassay*. Clin Infect Dis, 2005. 40(12): p. 1762-9; Musher, B., et al., *Aspergillus galactomannan enzyme immunoassay and quantitative PCR for diagnosis of invasive aspergillosis with bronchoalveolar lavage fluid*. J Clin Microbiol, 2004. 42(12): p. 5517-22.

a. GM EIA Index for Positivity

The result of the EIA is reported relative to a threshold control that contains 1 ng/mL of GM (supplied by the manufacturer), such that a GM EIA index equals the OD of the sample divided by the mean ODs of two threshold controls. The French manufacturer of the GM EIA (BioRad France) recommended using the GM index cut-off of 1.5 to define "positivity" and 1.0 to define "intermediate" for the diagnosis of aspergillosis. One study in allogeneic HCT and neutropenic patients noted that the overall sensitivity could be improved by 24% if the cut-off for positivity was decreased from 1.5 to 0.7, resulting in only a minimal (5.5%) decrease in specificity. Denning, D. W., et al., *Efficacy and safety of voriconazole in the treatment of acute invasive aspergillosis*. Clin Infect Dis, 2002. 34(5): p. 563-71. Other studies also supported this conclusion, suggesting that the cut-off can be lowered further to 0.5 to optimize sensitivity. Marr, K. A., et al., *Detection of galactomannan antigenemia by enzyme immunoassay for the diagnosis of invasive aspergillosis: variables that affect performance*. J Infect Dis, 2004. 190(3): p. 641-9. Subsequently, European centers have verified that performance is optimized at this low cut-off. Maertens, J. A., et al., *Optimization of the cutoff value for the Aspergillus double-sandwich enzyme immunoassay*. Clin Infect Dis, 2007. 44(10): p. 1329-36.

b. Use in Different Patient Populations

Early studies on the GM EIA focused on adult patients with hematologic malignancies. The few studies performed in children noted that false positivity may be more common in children compared to in adults, occurring in up to 75% of children with hematologic malignancies, with reported specificities for the assay as low as 37%. Hines, D. W., et al., *Pseudomembranous tracheobronchitis caused by Aspergillus*. Am Rev Respir Dis, 1991. 143(6): p. 1408-11; Marr, K. A. and W. Leisenring, *Design issues in studies evaluating diagnostic tests for aspergillosis*. Clin Infect Dis, 2005. 41 Suppl 6: p. S381-6; Mokkapati, V. K., et al., *Evaluation of UPlink-RSV: prototype rapid antigen test for detection of respiratory syncytial virus infection*. Ann N Y Acad Sci, 2007. 1098: p. 476-85.

Measurement of GM in various foods led some investigators to hypothesize that false-positivity occurs because children may have more gastrointestinal translocation of GM during periods of severe neutropenia and mucositis. Denning, D. W., et al., *Efficacy and safety of voriconazole in the treatment of acute invasive aspergillosis*. Clin Infect Dis, 2002. 34(5): p. 563-71; Rath, P. M. and R. Ansorg, *Value of environmental sampling and molecular typing of aspergilli to assess nosocomial sources of aspergillosis*. J Hosp Infect, 1997. 37(1): p. 47-53. A multicenter study was recently completed to evaluate this issue in children with hematologic malignancies, with the results suggesting that false positivity of the serum-based assay does occur with a compromise in specificity (albeit not as high as previously reported). Urine-based assays could have utility in this population, allowing for frequent, non-invasive testing to maximize detection of circulating antigens.

c. Appropriate Samples for Diagnostic Testing

Several laboratories have attempted to increase the predictive values of diagnostic assays by applying them to bronchoalveolar lavage (BAL) fluid. For example, in a study of 19 patients with hematologic malignancies and pulmonary infiltrates, positive GM EIA on BAL fluids accurately indicated IA and values in respiratory fluid corresponded with those in serum. Eskens, F. A., et al., *Septic shock caused by group G beta-haemolytic streptococci as presenting symptom of acute myeloid leukaemia*. Neth J Med, 1995. 46(3): p. 153-5. Frequent false-positive values associated with respiratory tract colonization of 'non-pathogenic' forms of the organism were noted, however, especially in patients who had less invasive clinical manifestations (i.e., airway disease in AIDS patients). Eskens, F. A., et al., *Septic shock caused by group G beta-haemolytic streptococci as presenting symptom of acute myeloid leukaemia*. Neth J Med, 1995. 46(3): p. 153-5; Einsele, H., et al., *Prediction of invasive pulmonary aspergillosis from colonisation of lower respiratory tract before marrow transplantation*. Lancet, 1998. 352(9138): p. 1443; Buchheidt, D., et al., *Detection of Aspergillus species in blood and bronchoalvolar lavage samples from immunocompromised patients by means of 2-step polymerase chain reaction: clinical results*. Clin Infect Dis, 2001. 33: p. 428-35. Results of a case-control study and several other recent efforts suggest that use of the GM EIA in BAL fluid enhances sensitivity of detecting IA by as much as 30%, with few false positive assay results. Musher, B., et al., *Aspergillus galactomannan enzyme immunoassay and quantitative PCR for diagnosis of invasive aspergillosis with bronchoalveolar lavage fluid*. J Clin Microbiol, 2004. 42(12): p. 5517-22; Meersseman, W., et al., *Galactomannan in bronchoalveolar lavage fluid: a tool for diagnosing aspergillosis in intensive care unit patients*. Am J Respir Crit Care Med, 2008. 177(1): p. 27-34; Husain, S., et al., *Performance characteristics of the platelia Aspergillus enzyme immunoassay for detection of Aspergillus galactomannan antigen in bronchoalveolar lavage fluid*. Clin Vaccine Immunol, 2008. 15(12): p. 1760-3; Nguyen, M. H., et al., *Use of bronchoalveolar lavage to detect galactomannan for diagnosis of pulmonary aspergillosis among non-immunocompromised hosts*. J Clin Microbiol, 2007. 45(9): p. 2787-92; Husain, S., et al., *Aspergillus galactomannan antigen in the bronchoalveolar lavage fluid for the diagnosis of invasive aspergillosis in lung transplant recipients*. Transplantation, 2007. 83(10): p. 1330-6; Clancy, C. J., et al., *Bronchoalveolar lavage galactomannan in diagnosis of invasive pulmonary aspergillosis among solid-organ transplant recipients*. J Clin Microbiol, 2007. 45(6): p. 1759-65; Sanguinetti, M., et al., *Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis*. J Clin Microbiol, 2003. 41(8): p. 3922-5; Becker, M. J., et al., *Galactomannan detection in computerized tomography-based broncho-alveolar lavage fluid and serum in haematological patients at risk for invasive pulmonary aspergillosis*. Br J Haematol, 2003. 121(3): p. 448-57.

If one considers that invasive disease is not necessitated by the finding of *Aspergillus* in airways, one can understand the strengths and limitations of applying sensitive tests to BAL fluid. More interpretation is required when finding *Aspergillus* in the airways and prediction of disease is dependent on the host. This scenario is not unlike the use of multiple other diagnostic assays for opportunistic organisms in immunosuppressed hosts, which differ compared to diagnostic tests of non-opportunists. The classic example is the finding of CMV viremia; presence of disease is dependent on multiple other variables. This example is in contradistinction to findings of HIV viremia, which can never be present as a 'normal' finding.

Although testing BAL fluid aids diagnosis upon recognition of radiographic abnormalities, it is not amenable to frequent sampling for early diagnosis. It appears to be possible, however, to increase the sensitivity of the GM EIA by measuring antigen secretion in urine. Studies in experimentally infected animals suggest that GM is concentrated in urine, rapidly after infection. Jensen, H. E., et al., *Detection of galactomannan and the 18 kDa antigen from Aspergillus fumigatus in serum and urine from cattle with systemic aspergillosis*. Zentralbl Veterinarmed [B], 1993. 40(6): p. 397-408; Bennett, J. E., M. M. Friedman, and B. Dupont, *Receptor-mediated clearance of Aspergillus galactomannan*. J Infect Dis, 1987. 155(5): p. 1005-10; Klont, R. R., M. A. Mennink-Kersten, and P. E. Verweij, *Utility of Aspergillus antigen detection in specimens other than serum specimens*. Clin Infect Dis, 2004. 39(10): p. 1467-74. In a rabbit model, 35% of GM was excreted in the urine within 24 hours of intravenous injection. Bennett, J. E., M. M. Friedman, and B. Dupont, *Receptor-mediated clearance of Aspergillus galactomannan*. J Infect Dis, 1987. 155(5): p. 1005-10. Studies evaluating samples from humans have reported favorable results of urine testing, Ansorg, R., E. Heintschel von Heinegg, and P. M. Rath, *Aspergillus antigenuria compared to antigenemia in bone marrow transplant recipients*. Eur J Clin Microbiol Infect Dis, 1994. 13(7): p. 582-9; Dupont, B., et al., *Galactomannan antigenemia and antigenuria in aspergillosis: studies in patients and experimentally infected rabbits*. J Infect Dis, 1987. 155(1): p. 1-11; Rogers, T. R., K. A. Haynes, and R. A. Barnes, *Value of antigen detection in predicting invasive pulmonary aspergillosis*.

Lancet, 1990. 336(8725): p. 1210-3, although the pharmacokinetics of GM clearance, the nature of the excreted antigen, and optimal parameters by which to perform testing have not been characterized.

The GM antigen in serum has an estimated mass >125 kD; the antigen that is detected by different galactofuranose-recognizing antibodies in urine might be variable and depend on the model evaluated. Klont, R. R., M. A. Mennink-Kersten, and P. E. Verweij, *Utility of Aspergillus antigen detection in specimens other than serum specimens.* Clin Infect Dis, 2004. 39(10): p. 1467-74. Other studies have reported that there is a reasonable frequency of false-positivity when testing urine samples for GM, although the GM EIA resulted in fewer false-positive results than did the assay using latex-agglutination. Ansorg, R., E. Heintschel von Heinegg, and P. M. Rath, *Aspergillus antigenuria compared to antigenemia in bone marrow transplant recipients.* Eur J Clin Microbiol Infect Dis, 1994. 13(7): p. 582-9. It has been postulated that this false-positivity may be caused by fungal contamination and overgrowth during specimen collection or processing. Dupont, B., et al., *Galactomannan antigenemia and antigenuria in aspergillosis: studies in patients and experimentally infected rabbits.* J infect Dis, 1987. 155(1): p. 1-11. Despite the potential advantages of screening urine samples instead of blood, no studies have been performed to define appropriate'testing conditions, or cut-offs using different antibodies, or to evaluate its potential for point-of-care testing. Further, many potential draw-backs of testing for GM antigen in urine (e.g., false positivity associated with sample contamination) might be avoided by use of rapid, self-contained testing tools, such as lateral flow devices.

5. Point-of-Care Diagnostics and Lateral Flow Devices: Theory and Current Applications The ability to provide test results rapidly to the patient and/or healthcare provider is very important to impact outcomes of multiple conditions. Rapid tests to aid diagnosis and enable early detection of multiple diseases and physiologic conditions are being developed. Such tests are especially useful when they can be applied with self-testing and require little in the way of laboratory processing. Examples of point-of-care (POC) test devices in common use today include pregnancy and fertility tests, as well as assays to follow blood glucose in diabetics. Development of diagnostic tests for infections that use POC testing are especially important in resource-poor settings; for this reason, POC testing has become a new goal to be achieved for infections such as HIV, malaria, and hepatitis. Similarly, POC testing has the potential of impacting clinical outcomes when applied to infections that occur in the outpatient setting, not only by providing indications of disease, but by enabling development of more robust prevention algorithms.

Commonly used immunoassays in diagnostic and research use include radio-immunoassays and enzyme-linked immunosorbent assays (ELISAs). Many of these elaborately configured immunoassays use monoclonal antibodies (MAbs) that possess the ability to bind specifically to the analyte being tested, thereby enhancing the accuracy of the assay. Various approaches have been described for carrying out enzyme immunoassays. A considerable number of these approaches, starting with the earliest of ELISAs, are solid-phase immunoassays in which the analyte to be detected is bound to a solid matrix directly (Direct ELISA) or indirectly (Sandwich ELISA), in which the analyte is captured on a primary reagent. The choice of the solid matrix depends on procedural considerations. A common matrix is the polystyrene surface of multi-well microtiter plates.

These types of assays also are amenable to developing POC devices, in which systems can be self-contained so that output is readable by the user. This characteristic is especially useful when collection of a sample to be tested does not require medical intervention (e.g., urine, saliva, or sputum). One device that enables this is the lateral-flow device (LFD). These devices use a multi-layered construction containing both absorbent and non-absorbent components to form a solid-phase. The capture and/or recognition reagents (antigen or antibody) are pre-applied to specific areas within the assembled apparatus and the analyte is allowed to flow through the system to come into contact with reagents. Often, for the purpose of self-containment, the reagent components are added in a dried state so that fluid from the sample re-hydrates and activates them. Conventional ELISA techniques can then be used to detect the analyte in the antigen-antibody complex. In some embodiments, the system can be designed to provide a colorimetric reading for visual estimation of a binary response ('yes' or 'no'), or it can be configured to be quantitative.

Lateral flow devices are used to detect analytes in multiple body fluids, including serum and urine. To date, these types of devices have seen the most use for detecting circulating endogenous analytes; perhaps the most common use of this type of device is in the ubiquitous POC pregnancy test. Current efforts are being directed toward detecting microbial analytes, including nucleic acids, in the setting of viral infections (e.g., influenza, respiratory syncytial virus, and the like), Nielsen, K., et al., *Prototype single step lateral flow technology for detection of avian influenza virus and chicken antibody to avian influenza virus.* J immunoassay Immunochem, 2007. 28(4): p. 307-18; Mokkapati, V. K., et al., *Evaluation of UPlink-RSV: prototype rapid antigen test for detection of respiratory syncytial virus infection.* Ann NY Acad Sci, 2007. 1098: p. 476-85; bacterial infections (e.g., *S. pneumoniae*, Legionella, Mycobacteria), Koide, M., et al., *Comparative evaluation of Duopath Legionella lateral flow assay against the conventional culture method using Legionella pneumophila and Legionella anisa strains.* Jpn J Infect Dis, 2007. 60(4): p. 214-6.

One assay that is in use worldwide is the BinaxNOW pneumococcal urinary antigen test; this assay evolved after the serum-based platform was shown to be effective, but cumbersome. The urinary POC device can be particularly useful when employed in high-risk patients as a POC testing device. Roson, B., et al., *Contribution of a urinary antigen assay (Binax NOW) to the early diagnosis of pneumococcal pneumonia.* Clin Infect Dis, 2004. 38(2): p. 222-6; Weatherall, C., R. Paoloni, and T. Gottlieb, *Point-of-care urinary pneumococcal antigen test in the emergency department for community acquired pneumonic.* Emerg Med J, 2008. 25(3): p. 144-8. This issue is particularly relevant in the context of the presently disclosed subject matter, as the polysaccharides in the pneumococcus capsule have some structural similarity to those of *Aspergillus*. Kappe, R. and A. Schulze-Berge, *New cause for false-positive results with the Pastorex Aspergillus antigen latex agglutination test.* J Clin Microbiol, 1993. 31(9): p. 2489-90; Stynen, D., et al., *Rat monoclonal antibodies against Aspergillus galactomannan.* Infect Immun, 1992. 60(6): p. 2237-45; Swanink, C. M., et al., *Specificity of a sandwich enzyme-linked immunosorbent assay for detecting Aspergillus galactomannan.* J Clin Microbiol, 1997. 35(1): p. 257-60.

Another lateral flow device has been developed recently to detect a protein antigen ("JF5") that is expressed on hyphae of *Aspergillus* and found in sera of patients with IA. Thornton, C. R., *Development of an immunochromato-*

*graphic lateral-flow device for rapid serodiagnosis of invasive aspergillosis.* Clin Vaccine Immunol, 2008. 15(7): p. 1095-105. While results of a small study suggest potential utility, applicability of this particular device is still hindered by requirements of serum testing.

II. Lateral Flow Device and Methods of Use Thereof for Diagnosing Microbial Infections As discussed hereinabove and as disclosed in Examples 2 and 3, preliminary studies have demonstrated that polysaccharide antigens of *A. fumigatus* (e.g., GM) are renally concentrated in animal model and are excreted in urine such that the sensitivity and specificity of a urine-based assay may equal or exceed that of serum based testing. Urinary detection of antigens would enable development of an easy-to-use POC testing method that would enable frequent testing in the outpatient setting, thus aiding the ability to diagnose and optimize screening strategies employed to detect infection early in the course of disease. Accordingly, in some embodiments, the presently disclosed subject matter provides a POC test to detect *Aspergillus* antigens (galactomannan) in urine. Monoclonal antibodies that recognize galactofuranose residues of *A. fumigatus* GM have been developed and are used in the presently disclosed GM test.

A standard ELISA format was used as a screen to identify antibodies to use for capture on the immobilized device. The identified antibody can be used as a capture antibody with point of care testing device (strip), which can be optimized for conditions to detect GM (antibody concentration, incubation conditions, and the like). Steps in development are detailed below and shown schematically in FIG. 11.

A. Methods for Diagnosing a Microbial Infection

Generally, the presently disclosed subject matter provides a method for diagnosing a microbial infection in a mammalian subject suspected of having, having, or susceptible to having a microbial infection by detecting the presence of at least one polysaccharide comprising a galactofuranose residue in a biological sample of the mammalian subject, the method comprising: (a) providing a biological sample from the subject; (b) contacting the biological sample with at least one antibody specific for at least one polysaccharide comprising a galactofuranose residue in an effective amount to produce a detectable amount of antibody-polysaccharide complex; and (c) detecting the presence of at least one antibody-polysaccharide complex, wherein the detection of the presence of at least one antibody-polysaccharide complex is diagnostic of a microbial infection in a mammalian subject.

The microbial infection can be selected from the group consisting of a bacterial infection and a fungal infection. In some embodiments, the bacterial infection is caused by an infection of *Streptococcus pneumoniae*. In other embodiments the microbial infection is a fungal infection caused by an infection of an organism selected from the group consisting of *Aspergillus* species, *Fusarium* species, *Coccidomycoses* species, *Cryptococcus* species, and *Histoplasmosis* species.

In particular embodiments, the at least one antibody specific for at least one polysaccharide comprising a galactofuranose residue is selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10.

One of ordinary skill in the art upon review of the presently disclosed subject matter would appreciate that any biological fluid in which at least one polysaccharide comprising a galactofuranose residue is secreted is suitable for use with the presently disclosed methods. In particular embodiments, the biological sample is selected from the group consisting of urine, bronchoalveolar lavage (BAL) fluid, serum, blood, and cerebrospinal fluid (CSF).

In some embodiments, the presently disclosed methods further comprise pre-treating the biological sample before contacting the biological sample with at least one antibody specific for at least one polysaccharide comprising a galactofuranose residue. The pre-treating step can include a step selected from the group consisting of filtering, diluting, and concentrating the biological sample, and combinations thereof. In particular embodiments, the pre-treating includes filtering the biological sample to remove an inhibitor that interferes with the detection of the at least one polysaccharide comprising a galactofuranose residue in the biological sample.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In particular embodiments, the subject is a human adult suspected of having, having, or susceptible of having a microbial infection. In other embodiments, the subject is a human child, e.g., a human less than about 19 years of age, suspected of having, having, or susceptible of having a microbial infection.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed. The term "monitoring," such as in "monitoring the course of a disease or condition," refers to the ongoing diagnosis of samples obtained from a subject having or suspected of having a disease or condition. The term "marker" refers to a molecule, including an antigen, such as a polysaccharide, that when detected in a sample is characteristic of or indicates the presence of a disease or condition.

Accordingly, in some embodiments, the presently disclosed subject matter provides a method for diagnosing of a microbial infection in a mammalian subject suspected of having, having, or susceptible to having a microbial infection, wherein the method comprises monitoring a treatment regimen of a microbial infection to determine the efficacy of the treatment regimen.

B. Lateral Flow Devices for Diagnosing a Microbial Infection

Referring generally to FIG. 4, the presently disclosed lateral flow device comprises an immunochromographic strip test that relies on a direct (double antibody sandwich) reaction. Without wishing to be bound to any one particular theory, this direct reaction scheme is best used when sampling for larger analytes that may have multiple antigenic sites. Different antibody combinations can be used, for example different antibodies can be included on the capture (detection) line, the control line, and included in the mobile phase of the assay, for example, as conjugated to gold particles, e.g., gold microparticles or gold nanoparticles.

A variety of physical characteristics can influence performance of the device including, but not limited to, selection of the appropriate sample pad, conjugate pad, detection conjugate, lateral flow membrane, absorbent pad, plastic-adhesive backing card, laminate cover taping, and the like. Other parameters include consideration of duration and method of sample exposure.

As used herein the term "lateral flow" refers to liquid flow along the plane of a substrate or carrier, e.g., a lateral flow membrane. In general, lateral flow devices comprise a strip (or a plurality of strips in fluid communication) of material capable of transporting a solution by capillary action, i.e., a wicking or chromatographic action, wherein different areas or zones in the strip(s) contain assay reagents, which are either diffusively or non-diffusively bound to the substrate, that produce a detectable signal as the solution is transported to or migrates through such zones. Typically, such assays comprise an application zone adapted to receive a liquid sample, a reagent zone spaced laterally from and in fluid communication with the application zone, and a detection zone spaced laterally from and in fluid communication with the reagent zone. The reagent zone can comprise a compound that is mobile in the liquid and capable of interacting with an analyte in the sample, e.g., to form an analyte-reagent complex, and/or with a molecule bound in the detection zone. The detection zone may comprise a binding molecule that is immobilized on the strip and is capable of interacting with the analyte and/or the reagent and/or an analyte-reagent complex to produce a detectable signal. Such assays can be used to detect an analyte in a sample through direct (sandwich assay) or competitive binding. Examples of lateral flow devices are provided in U.S. Pat. No. 6,194,220 to Malick et al.; U.S. Pat. No. 5,998,221 to Malick et al.; U.S. Pat. No. 5,798,273 to Shuler et al.; and RE38,430 to Rosenstein.

As provided hereinabove, in some embodiments, the presently disclosed assay comprises a sandwich lateral flow assay. In a sandwich lateral flow assay, a liquid sample that may or may not contain an analyte of interest is applied to the application zone and allowed to pass into the reagent zone by capillary action. The term "analyte" as used herein refers to a polysaccharide comprising a galactofuranose residue. In certain embodiments the presence or absence of an analyte in a sample is determined qualitatively. In other embodiments, a quantitative determination of the amount or concentration of analyte in the sample is determined.

The analyte, if present, interacts with a labeled reagent in the reagent zone to form an analyte-reagent complex and the analyte-reagent complex moves by capillary action to the detection zone. The analyte-reagent complex becomes trapped in the detection zone by interacting with a binding molecule specific for the analyte and/or reagent. Unbound sample can pass through the detection zone by capillary action to a control zone or an absorbent pad laterally juxtaposed and in fluid communication with the detection zone. The labeled reagent may then be detected in the detection zone by appropriate means.

More particularly, referring now to FIG. 5, lateral flow device 500 according to the presently disclosed subject matter is provided. One of ordinary skill in the art would recognize that other embodiments of lateral flow devices are suitable for use with the presently disclosed methods. Accordingly, lateral flow device 500 is provided as an illustrative, non-limiting example of the presently disclosed subject matter.

Lateral flow device 500 comprises sample pad 510. Sample pad 510 comprises a membrane surface 515, also referred to herein as a "sample application zone," adapted to receive a liquid sample. A standard cellulose sample pad has been shown to facilitate absorption and flow of biological samples, including, but not limited to, urine. Referring once again to FIG. 5, sample pad 510 comprises a portion of lateral flow device 500 that is in direct contact with the liquid sample, that is, it receives the sample to be tested for the analyte of interest. Sample pad 510 can be part of, or separate from, a lateral flow membrane. Accordingly, the liquid sample can migrate, through lateral or capillary flow, from sample pad 510 toward a portion of the lateral flow membrane comprising a detection zone. Sample pad 510 is in fluid communication with the lateral flow membrane comprising an analyte detection zone. This fluid communication can arise through either be an overlap, top-to-bottom, or an end-to-end fluid connection between sample pad 510 and a lateral flow membrane. In certain embodiments, sample pad 510 comprises a porous material, for example and not limited to, paper.

The term "sample" as used herein refers to any biological sample suspected of containing an analyte for detection or a control sample expected to be substantially free of the analyte of interest. In particular embodiments, the sample comprises a biological fluid of a subject suspected of having, having, or susceptible of having a microbial infection. In some embodiments, the biological sample is in liquid form, while in other embodiments it can be changed into a liquid form, e.g., by reconstitution in a suitable solvent, e.g., an aqueous solution. The presently disclosed lateral flow devices are suitable for use with a variety of biological samples including, but not limited to, urine, bronchoalveolar lavage (BAL) fluid, serum, blood, and cerebrospinal fluid (CSF).

Sample pad 510 is positioned adjacent to and in fluid communication with conjugate pad 520. Conjugate pad 520 comprises a labeled reagent having specificity for one or more analytes of interest. In some embodiments, conjugate pad 520 comprises a non-absorbent, synthetic material (e.g., polyester) to ensure release of its contents. A detection conjugate is dried into place on conjugate pad 520 and only released when the liquid sample is applied to sample pad 510. Detection conjugate can be added to the pad by immersion or spraying.

In particular embodiments, the detection conjugate comprises an antibody having specificity for a polysaccharide comprising a galactofuranose residue. In representative embodiments, the antibody is selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10. The antibody, e.g., a monoclonal antibody (MAb), can be conjugated to a gold particle, e.g., colloidal gold, including gold microspheres or gold nanoparticles, such as gold nanoparticles of about 40 nm. For example, it is possible to biotinylate the conjugated MAb to take advantage of the strong affinity that biotin has for streptavidin, using Streptavidin-coated microspheres. Alternatives include protein A-coated microspheres that bind to Fe region of IgGs. Conditions to define optimal optimization to colloidal gold can be determined, for example, in microtiter wells. For example, 100 μL of colloidal gold at 1 OD530 can be added to each well, followed by 10 μL of 22 mM buffers (MES, HEPES) at variable pH (5.5 to 10, in 0.5 increments). Antibodies can be added at concentrations ranging from about 1.25 μg/1 OD colloid to about 10 μg/1 OD colloid, incubated for 15 minutes, and then 25 μL of 1.5 NaCl can be added. Conjugated particles will be stable and pink; the optimal condition that requires the lowest concentration of antibodies can be determined.

Referring once again to FIG. 5, conjugate pad 520 is adjacent to and in fluid communication with lateral flow membrane 530. Capillary action draws a fluid mixture up sample pad 510, through conjugate pad 520 where an antibody-polysaccharide complex is formed, and into the lateral flow membrane 530. Lateral flow is a function of the properties of lateral flow membrane 530. Lateral flow membrane 530 typically is extremely thin and is hydrophilic enough to be wetted, thereby permitting unimpeded lateral flow and mixture of reactants and analytes at essentially the same rates.

Lateral flow membrane 530 can comprise any substrate capable of providing liquid flow including, but not limited to, substrates, such as nitrocellulose, nitrocellulose blends with polyester or cellulose, untreated paper, porous paper, rayon, glass fiber, acrylonitrile copolymer, plastic, glass, or nylon. Lateral flow membrane 530 can be porous. Typically, the pores of lateral flow membrane 530 are of sufficient size such that particles, e.g., microparticles comprising a reagent capable of forming a complex with an analyte, flow through the entirety of the membrane. Lateral flow membrane 530, in general, can have a pore size ranging from about 3 μm to about 100 μm, and, in some embodiments, have a pore size ranging from about 10 μm to about 50 μm. Pore size affects capillary flow rate and the overall performance of the device.

There are multiple benefits to using nitrocellulose for the primary membrane: low cost, capillary flow high affinity for protein biding, and ease of handling. Nitrocellulose has high protein binding. Another alternative is cellulose acetate, which has low protein binding. Size dictating surface area dictates membrane capacity (the volume of sample that can pass through the membrane per unit time=length×width×thickness×porosity. Because these variables control the rate at which lateral flow occurs, they can impact sensitivity and specificity of the assay. The flow rate also varies with sample viscosity. Several different sizes and polymers are available for use as microspheres, which migrate down the membrane with introduction of the fluidic sample. The optimal flow rate generally is achieved using spheres that are 1/10 the pore size of the membrane or smaller.

One skilled in the art will be aware of other materials that allow liquid flow. Lateral flow membrane 530, in some embodiments, can comprise one or more substrates in fluid communication. For example, conjugate pad 520 can be present on the same substrate or may be present on separate substrates (i.e., pads) within or in fluid communication with lateral flow membrane 530. In some embodiments, the nitrocellulose membrane can comprise a very thin Mylar sheet coated with a nitrocellulose layer.

Lateral flow membrane 530 can further comprise at least one indicator zone or detection zone 540. The terms "indicator zone" and "detection zone" are used interchangeably herein and mean the portion of the carrier or porous membrane comprising an immobilized binding reagent. As used herein, the term "binding reagent" means any molecule or a molecule bound to a particle, wherein the molecule recognizes or binds the analyte in question. The binding reagent is capable of forming a binding complex with the analyte-labeled reagent complex. The binding reagent is immobilized in the detection zone and is not affected by the lateral flow of the liquid sample due to the immobilization on the membrane. Once the binding reagent binds the analyte-labeled reagent complex it prevents the analyte-labeled reagent complex from continuing with the flow of the liquid sample. In some embodiments, the binding reagent is an antibody having specificity for a polysaccharide having at least one galactofuranose residue. In particular embodiments, the binding reagent comprises an antibody selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10.

Accordingly, during the actual reaction between the analyte and the reagent, the first member binds in the indicator zone to the second member and the resulting bound complex is detected with specific antibodies. Detection may use any of a variety of labels and/or markers, e.g., enzymes (alkaline phosphatase or horseradish peroxidase with appropriate substrates), radioisotopes, liposomes or latex beads impregnated with fluorescent tags, polymer dyes or colored particles, and the like. Thus, the result can be interpreted by any direct or indirect reaction. Colloidal gold particles, which impart a purple or red coloration, are most commonly used currently.

The capture and immobilization of the assay reagent (complementary member of the binding pair) at indicator zone 540 can be accomplished by covalent bonding or, more commonly, by adsorption, such as by drying. Such capture also can be indirect, for example, by binding of latex beads coated with the reagent. Depending on the nature of the material comprising the lateral flow membrane 530, covalent bonding may be enabled, for example with use of glutaraldehyde or a carbodiimide. In immunoassays, most common binding pairs are antigen-antibody pairs; however, multiple other binding pairs can be performed, such as enzyme-substrate and receptor-ligand.

In some embodiments, indicator zone 540 further comprises test line 550 and control line 560. Test line 550 can comprise an immobilized binding reagent. When antibodies are used to develop a test line in the LFD that employs a sandwich type of assay, they are applied at a ratio of about 1-3 µg/cm across the width of a strip 1 mm wide; hence, antibody concentration is about 10-30 $\mu g/cm^2$, which is about 25-100 fold that used in an ELISA. Brown, M. C., *Antibodies: key to a robust lateral flow immunoassay*, in *Lateral Flow Immunoassay*, H. Y. T. R. C. Wong, Editor. 2009, Humana Press: New York, N.Y. p. 59-74.

Further, in some embodiments, the presently disclosed lateral flow assays can be used to detect multiple analytes in a sample. For example, in a lateral flow assay, the reagent zone can comprise multiple labeled reagents, each capable of binding to a different analyte in a liquid sample or a single labeled reagent capable of binding to multiple analytes. If multiple labeled reagents are used in a lateral flow assay, the reagents may be differentially labeled to distinguish different types of analytes in a liquid sample.

It also is possible to place multiple lines of capture antibodies on the membrane to detect different analytes. Combinations of antibodies that detect different epitopes of galactomannoproteins may optimize specificity if it is found that one antibody performs at a low quantitative limit of detection, yet exhibits some degree of nonspecific binding (or binding to urine components in control animals). One possibility is that the device may be adapted to detect GM and another fungal component to increase the potential spectrum of pathogens detected and to increase specificity of the reaction. *Aspergillus* species are thought to secrete GM and other fungal components, while galactomannoproteins from other 'contaminants' should not contain other fungal components.

For quality control, lateral flow membrane 530 can include a control zone comprising control line 560. The term "control zone" refers to a portion of the test device comprising a binding molecule configured to capture the labeled reagent. In a lateral flow assay, the control zone may be in liquid flow contact with the detection zone of the carrier, such that the labeled reagent is captured on the control line as the liquid sample is transported out of the detection zone by capillary action. Detection of the labeled reagent on the control line confirms that the assay is functioning for its intended purpose. Placement of control line 560 can be accomplished using a microprocessor controlled TLC spotter, in which a dispenser pump releases a constant volume of reagent across the membrane.

Lateral flow device 500 also comprises absorbent pad 570. Absorbent pad 570 comprises an "absorbent material," which as used herein, refers to a porous material having an absorbing capacity sufficient to absorb substantially all the liquids of the assay reagents and any wash solutions and, optionally, to initiate capillary action and draw the assay liquids through the test device. Suitable absorbent materials include, for example, nitrocellulose, nitrocellulose blends with polyester or cellulose, untreated paper, porous paper, rayon, glass fiber, acrylonitrile copolymer, plastic, glass, or nylon.

In some embodiments, lateral flow membrane 530 is bound to one or more substantially fluid-impervious sheets, one on either side, e.g., bottom sheet 580 and a complimentary top sheet (not shown) with one or more windows (not shown) defining application zone 515 and indicator zone 540.

Lateral flow device 500 also can include a housing (not shown). The term "housing" refers to any suitable enclosure for the presently disclosed lateral flow devices. Exemplary housings will be known to those skilled in the art. The housing can have, for example, a base portion and a lid portion. The lid portion can include a top wall and a substantially vertical side wall. A rim may project upwardly from the top wall and may further define a recess adapted to collect a sample from a subject. Suitable housings include those provided in U.S. Pat. No. 7,052,831 to Fletcher et al and those used in the BD Directigen™ EZ RSV lateral flow assay device.

Accordingly, in some embodiments, the presently disclosed subject matter provides a lateral flow device for diagnosing a microbial infection in a biological sample of a mammalian subject suspected of having, having, or susceptible to having a microbial infection, the devise comprising: (a) a solid layer having a first end, a second end, and a surface on which at least one antibody specific for at least one polysaccharide comprising a galactofuranose residue is deposited in a defined area on the surface of the solid layer; (b) an agent capable of reacting with the at least one antibody specific for at least one polysaccharide comprising a galactofuranose residue to form a detectable complex; (c) a flow channel in the solid layer that allows passage of sample liquid from the first end of the solid layer to the second end of the solid layer; and (d) a second agent capable of reacting with the detectable complex, wherein a detection of the detectable complex diagnoses a microbial infection in the biological sample.

In some embodiments, the lateral flow device further comprises a case enclosing the solid layer. The case can further comprise a window in the case enclosing the solid layer to allow sample fluid to contact the solid layer and/or a window in the case allowing viewing of the detection of the detectable complex.

As with the general method described immediately hereinabove, the microbial infection can be selected from the group consisting of a bacterial infection and a fungal infection. In some embodiments, the bacterial infection is caused by an infection of *Streptococcus pneumoniae*. In particular embodiments, the microbial infection is a fungal infection caused by an infection of an organism selected from the group consisting of *Aspergillus* species, *Fusarium* species, *Coccidomycoses* species, *Cryptococcus* species, and *Histoplasmosis* species.

As described in more detail immediately herein below, the presently disclosed lateral flow device comprises, in some embodiments, at least one antibody specific for at least one polysaccharide comprising a galactofuranose residue is selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10.

The presently disclosed lateral flow devices are suitable for use with a variety of biological samples including, but not limited to, urine, bronchoalveolar lavage (BAL) fluid, serum, blood, and cerebrospinal fluid (CSF).

In some embodiments, a polysaccharide having a galactofuranose residue can be measured in whole, unconcentrated, or otherwise unprocessed, biological samples using the presently disclosed methods and devices. In other embodiments, the biological sample can be processed, e.g., concentrated, diluted, filtered, and the like, prior to performing the test. The pre-treatment of the urine sample can include diluting the urine sample in an aqueous solution, concentrating the urine sample, filtering the urine sample, or a combination thereof.

One of ordinary skill in the art upon review of the presently disclosed subject matter would appreciate that the pre-treatment steps can be performed in any particular order, e.g., in some embodiments, the sample can be diluted or concentrated and then filtered, whereas in other embodiments, the sample can be filtered and then diluted or concentrated. In particular embodiments, the presently disclosed methods include filtering the urine sample, for example, through a desalting column, to remove an inhibitor that interferes with the detection of antigen in the urine sample. This step can be performed with or without any further dilution or concentration of the sample.

Thus, in some embodiments, the lateral flow device further comprises an apparatus adapted to pre-treat the biological sample before contacting the biological sample with at least one antibody specific for at least one polysaccharide comprising a galactofuranose residue. In particular embodiments, the apparatus is adapted to filter, dilute, or concentrate the biological sample, or combinations thereof. More particularly, the apparatus can be adapted to remove an inhibitor that interferes with the detection of the at least one polysaccharide comprising a galactofuranose residue in the biological sample, in particular, a urine sample.

In other embodiments, different parameters of the test, e.g., incubation time, can be manipulated to increase sensitivity and/or specificity of the test to eliminate the need for processing the biological sample.

Antibody choice is very important to consider in the presently disclosed lateral flow assays. In previous studies using ELISA, the relative binding efficacy of GM in different animal samples was determined. The presently disclosed MAbs are well characterized and are particularly well suited for LFD. The urine antigen(s) that is/are recognized by the MAbs is/are not well characterized and these antigens might exhibit antigen polymorphism that can impact test performance. This characteristic potentially could be most important when considering performance for diagnosing infection caused by different *Aspergillus* species. If antigenic polymorphism does indeed exist, it might be useful to develop polyclonal Abs that recognize *Aspergillus* GMs to increase the target repertoire.

Accordingly, in some embodiments, the presently disclosed subject matter provides an antibody specific for at least epitope of a polysaccharide secreted by a microbial organism. In particular embodiments, the polysaccharide comprises a galactofuranose residue. In more particular embodiments, the antibody is specific for at least one epitope of a polysaccharide secreted by a microbial organism selected from the group consisting of *Aspergillus* species, *Fusarium* species, *Coccidomycoses* species, *Cryptococcus* species, *Histoplasmosis* species, and *Streptococcus* pneumoniae species.

In some embodiments, the antibody is selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10.

C. Kits

In some embodiments, the presently disclosed subject matter provides a kit comprising an antibody selected from the group consisting of monoclonal antibody 205 (MAb 205) comprising a variable heavy ($V_H$) domain of SEQ ID NO:1 and a variable light ($V_L$) domain of SEQ ID NO:2; monoclonal antibody 24 (MAb 24) comprising a $V_H$ domain of SEQ ID NO:3 and a $V_L$ domain of SEQ ID NO:4; monoclonal antibody 686 (MAb 686) comprising a $V_H$ domain of SEQ ID NO:5 and a $V_L$ domain of SEQ ID NO:6; monoclonal antibody 838 (MAb 838) comprising a $V_H$ domain of SEQ ID NO:7 and a $V_L$ domain of SEQ ID NO:8; and monoclonal antibody 476 (MAb 476) comprising a $V_H$ domain of SEQ ID NO:9 and a $V_L$ domain of SEQ ID NO:10. The kit can further comprise a lateral flow device, either fully assembled, or unassembled components of the lateral flow devices disclosed herein. The kit can comprise an apparatus adapted for pre-treating the sample prior to depositing the sample in the lateral flow device. In other embodiments, the kit further comprises instructions for use for diagnosing a microbial infection in a biological sample of a mammalian subject suspected of having, having, or susceptible to having a microbial infection, In summary, there is great potential in optimizing an assay towards a POC platform for screening of IA, as these infections develop outside of hospitals, and early detection is the primary goal. Urinary polysaccharide allows for development of a POC testing platform using lateral flow methodologies. The presently disclosed subject matter applies innovative point-of-care technologies to develop new devices and to optimize current testing systems (using new non-standard body fluids); meeting these milestones has the potential significance of defining a new, powerful strategy to self-test for early diagnosis of invasive fungal infections in multiple hospital and outpatient settings.

III. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Detection of GM Using Novel Monoclonal Antibodies (MAb) in Animal Models

Production of GM-Binding MAbs.

MAbs to the conidial surface were prepared as part of a strategy to identify germination-inhibitory MAbs. Mice were immunized intraperitoneally with heat-killed conidia of *A. fumigatus* strain 293. The first immunization was administered with complete Freund's adjuvant. Conidia surface-binding Ab titers were measured by ELISA. After five immunizations, mice had geometric mean conidial surface binding 1 g titers, including both IgM and IgG, of 1:12,800, as compared to <1:200 prior to immunization. Following a sixth immunization, one mouse had an IgM and IgG titer of 1:52,600. Eleven IgMκ-producing hybridomas were made by fusion of the spleen of this mouse to a standard fusion partner. Hybridomas were cloned twice by plating on soft agar. The nucleotide sequences encoding these MAbs are presented in Table 1.

TABLE 1

Nucleotide Sequences of Presently Disclosed MAbs

| MAb | Nucleotide Sequence |
| --- | --- |
| 205 VH (15A)<br>SEQ ID NO: 1 | gaggtgcagctggaggagtctctgagactctcctgtgcaacttctgggttcaccttcagtg<br>atttctacatggagtgggtccgccagcctccagggaagagactggagtggattgctgca<br>agtagaaacaaagctaatgattatacaacagagtacagtgcatctgtgaagggtcggttc<br>atcgtctccagagacacttcccaaagcatcctctaccttcagatgaatgccctgagagctg<br>aggacactgccatttattactgtgcaagagattactacggtagtagctactggtacttcgat<br>gtctggggcgcagggaccacggtcaccgtctcctca |
| 205 VL (P1A)<br>SEQ ID NO: 2 | gacattctgatgacccagtctccaactttccttgctgtgacagcaagtaagaaggtcaccat<br>tagttgcacggccagtgagagcctttattcaagcaaacacaaggtgcactacttggcttgg<br>taccagaagaaaccagagcaatctcctaaactgctgatatacggggcatccaaccgata<br>cattgggtccctgatcgcttcacaggcagtggatctgggacagatttcactctgaccatc<br>agcagtgtacaggttgaagacctcacacattattactgtgcacagttttacagctatcctctc<br>acgttcggctcggggacaaagttggaaataaaacg |

TABLE 1-continued

Nucleotide Sequences of Presently Disclosed MAbs

| MAb | Nucleotide Sequence |
|---|---|
| 24 VH (PA7) SEQ ID NO: 3 | gaggtgcagctggaggantctgggggagacttagtgaagcctggagggtccctgaaac tctcctgtgcagcctctggattcactttcagtagctatggcatgtcttgggttcgccagactc cagacaagaggctggagtgggtcgcaaccattagtagtggtggtagttacacctactatc cagacagtgtgaaggggcgattccaccatctccagagacaatgccaagaacaccctgtac ctgcaaatgagcagtctgaagtctgaggacacagccatgtattactgtgcaagacttacta cggtagtagctatgctatggactactggggtcaaggaacctcagtcaccgtctcctca |
| 24 VL (B6A) SEQ ID NO: 4 | gacattctgatgacccagtctccaactttccttgctgtgacagcaagtaagaaggtcaccat tagttgcacggccagtgagagcctttattcaagcaaacacaaggtgcactacttggcttgg taccagaagaaaccagagcaatctcctaaactgctgatatacggggcatccaaccgata cattggggtccctgatcgcttcacaggcagtggatctgggacagatttcactctgaccatc agcagtgtacaggttgaagacctcacacattattactgtgcacagttttacagctatcctctc acgttcggtgctgggaccaagctggagctgaaacg |
| 686 VH (C5A) SEQ ID NO: 5 | gaggtgcagctggaggagtctggaggaggcttggtacagcctggggggttctctgagact ctcctgtgcaacttctgggttcaccttcagtgatttctacatggagtgggtccgccagcctc cagggaagagactggagtggattgctgcaagtagaaacaaagctaatgattatacaaca gagtacagtgcatctgtgaagggtcggttcatcgtctccagagacacttcccaaagcatc ctctaccttcagatgaatgccctgagagctgaggacactgccatttattactgtgcaagag attactacggtagtagctactggtacttcgatgtctggggcgcagggaccacggtcaccg tctcctca |
| 686 VL (P2A) SEQ ID NO: 6 | gacattctgatgacccagtctccaactttccttgctgtgacagcaagtaagaaggtcaccat tagttgcacggccagtgagagcctttattcaagcaaacacaaggtgcactacttggcttgg taccagaagaaaccagagcaatctcctaaactgctgatatacggggcatccaaccgata cattggggtccctgatcgcttcacaggcagtggatctgggacagatttcactctgaccatc agcagtgtacaggttgaagacctcacacattattactgtgcacagttttacagctatccgct cacgttcggtgctgggaccaagctggagctgaaacg |
| 838 VH (B4B) SEQ ID NO: 7 | gaggtgcagctggaggagtctctgagactctcctgtgcaacttctgggttcaccttcagtg atttctacatggagtgggtccgccagcctccagggaagagactggagtggattgctgca agtagaaacaaagctaatgattatacaacagagtacagtgcatctgtgaagggtcggttct tcgtctccagagacacttcccaaagcatcctctaccttcagatgaatgccctgagagctga ggacactgccatttattactgtgcaagagatgttatgattacgacggggactggtacttc gatgtctggggcgcagggaccacggtcaccgtctcctca |
| 838 VL (p6) SEQ ID NO: 8 | gacattctgatgacccagtctcaaaaattcatgtccacatcagtaggagacagggtcagc gtcacctgcaaggccagtcagaatgtgggtactaatgtagcctggtatcaacagaaacca gggcaatctcctaaagcactgatttactcggcatcctaccagtacagtggagtccctgatc gcttcacaggcagtggatctgggacagatttcactctcaccatcagcaatgtgcagtctga agacttggcagagtatttctgtcagcaatttaacagctatcacgttcggctcggggacaaa gttggaattaaaacg |
| 476 VH (P10B-TA) SEQ ID NO: 9 | gaggtgcagctggaggagtctggaggaggcttggtacagcctggggggttctctgagact ctcctgtgcaacttctgggttcaccttcagtgatttctacatggagtgggtccgccagactc caggggagagactggagtggattgctgcaagtagaaacaaagctaatgattatacagca gaatacagtgcgtctgtgaagggtcgattcaccgtctttagagacacttcccaaaacatcc tctaccttcagatgaatgccctgagagctgaagacactgccgcctattactgtgcaagaga tgcggactacggtaaaaccttttcctggtacttcgatgtctggggcgcagggaccacggt caccgtctcatca |
| 476 VL (F6A*-TA) SEQ ID NO: 10 | gatattgtaatgacccaagatgaactctccaatcctgtcacttctggagaatcagttcacatc tcctgcaggtctagtaagagtctcctatataaggatgggaagacatacttgaattggtttct gcagagaccaggacaatctcctcagctcctgatctatttgatgtccacccgtgcatcagga gtctcagaccggtttagtggcagtgggtcaggaacagatttcaccctggaaatcagtaga gtgaaggctgaggatgtgggtgtgtattattgtcaacaacttgtagaatatccgctcacgtt cggtgctgggaccaagctggagctgaaacg |

GM is secreted during growth in vitro and forms a major component of the ethanol precipitable fraction of the culture filtrate. Knutsen, A., et al., *Asp f*1 *CD4+ Th2-like T cell lines in allergic bronchopulmonary aspergillosis*. J Allergy Clin Immunol, 1994. 94: p. 215-221. To identify MAbs that bound to secreted antigens, *A. fumigatus* was grown in Sabouraud's dextrose broth at 37° C. for five days. Binding of the MAbs to the secreted material was determined by ELISA. Culture filtrate was added to 96 well EIA plates and serially diluted to yield concentrations ranging from 10 to 0.01 μg/mL of polysaccharide. Control wells contained no polysaccharide. Five of 11 MAbs binded to culture filtrate. These antibodies were tested for binding of purified GM. ELISA plates were coated with GM at a starting concentration of 10 μg/mL that was serially diluted 1:2 across the plate and incubated at 37° C. After washing and blocking, MAbs were added to the wells at a concentration of 10 μg/mL. All but one of the five MAb that bound to culture filtrate bound to purified galactomannan (FIG. 7). In particular; MAb 476 exhibited a high affinity to *Aspergillus* polysaccharide antigens (FIG. 7). None of the MAbs that did not bind to culture filtrate antigens bound to galactomannan (not shown). MAbs that bound to GM were assayed for binding to GM treated with 0.01 N HCl, which removes galactofuranose residues; none of these MAbs bound to acid-treated GM (FIG. 7), suggesting that they all, at least in part, recognize and bind to the galactofuranose portion of the molecule or that galactofuranose is important in generating the epitope recognized.

Capture ELISA. One of these MAbs, MAb 476, was purified from ascites made in SCID mice by ammonium sulfate precipitation, followed by anion exchange chromatography using a CHT II cartridge (Biorad). Following dialysis against 50 mM sodium phosphate buffer, MAb purification was verified by SDS-PAGE on a non-reducing gel. MAb 476 was conjugated to sulfosuccinimidyl-6-(biotin-amido)-hexanoate according to the manufacturer's instructions (Pierce; Rockford, Ill.). For capture ELISA, microliter plates were coated with a 10 mg/mL solution of purified MAb 476, then blocked with PBS with 2% BSA. This concentration was selected for capture as preliminary experiments found that it allowed for the lowest background. Culture filtrate or purified GM was then added to the wells at starting concentrations of 10 µg/mL or 1 µg/mL of polysaccharide, respectively, and serially diluted across the plate. After washing, a 0.5 µg/mL solution of biotin-conjugated MAb 476 was added to the wells. Wells were incubated in alkaline phosphatase-conjugated streptavidin, then p-nitrophenol phosphate was added as the substrate and the absorbance at 405 nm measured. Control wells did not contain culture filtrate. All incubations were performed at 37° C. for one hour or at 4° C. overnight. The purified GM concentration that resulted in an O.D. twice that of background was approximately 50 ng/mL (not shown).

Capture ELISA detects GM made in vivo after experimental pulmonary infection. Neutropenia was induced in C57BL/6 mice by co-administration of cyclophosphamide and triamcinolone. Mice were infected intratracheally with $5 \times 10^6$ conidia of *A. fumigatus* strain 90906. Two days after infection, mice were bled from the orbital sinus and then killed by cervical dislocation. Uninfected neutropenic mice were used as controls. Bronchoalveolar lavage (BAL) was performed using 0.8 mL of sterile PBS, after which lungs were homogenized in 5 mL of PBS with 0.05% Tween 20. Homogenates then were centrifuged to remove particulate matter. Serum, BAL fluid and lung homogenates were boiled with 4% EDTA to remove proteins and disassociate any antigen-Ab complexes. Kirsten, D., et al., *Invasive aspergillosis in cavitary lung sarcoidosis*. Pneumologie, 1992. 46: p. 239-242. Capture ELISA was performed as above and a positive result was defined at an O.D. greater than the mean+3 S.D.s of the control samples, the O.D.s of which did not differ from control wells without samples.

GM was detected in BAL fluid, lung homogenates and serum from all infected mice. More particularly, the antibody was tested using materials collected from Af293-infected mice and compared to controls. Capture ELISA with MAb476 detected GM in BAL and lung homogenate after infection (FIG. 8, top panel). Relative absorbance of serum was higher in animals infected with Af293 compared to uninfected controls (FIG. 8, bottom panel).

GM-Binding Characterization.

Capture ELISA was performed to determine relative cross-reactivity of the GM-binding MAbs to other fungal antigens and organisms of interest using microbial culture filtrate precipitated with ethanol. Each MAbs bound to ethanol-precipitated culture filtrates, i.e., each antibody recognized antigen, of three strains of *A. fumigatus* tested, as well as to *A. flavus*, *A. niger*, *Penicillium* spp., *Fusarium* spp., *Trichophyton rubrum* and *Streptococcus pneumoniae* serotype 34, each of which is bound by MAb EBA2. (While the non-specific nature of antigen binding might be considered a potential limitation of antigen detection, current diagnostic assays that are increasingly used to detect pulmonary pathogens, such as *S. pneumoniae*, similarly detect polysaccharide antigens that are excreted in urine and maximally detected in concentrated specimens, providing ample evidence that urine-based polysaccharide detection is a good prospect for screening, in which POC, self contained testing and sensitivity (not specificity) should be emphasized.) Similarly, these MAbs did not bind to similar preparations from *A. terreus*, *Candida albicans*, *Clyptococcus neoformans*, or *Wangiella dermatilidis*, none of which were originally reported to be bound by MAb EBA2, though binding to cryptococcal GXM has been described. Dalle, F., et al., *Cryptococcus neoformans Galactoxylomannan contains an epitope(s) that is cross-reactive with Aspergillus Galactomannan*. J Clin Microbiol, 2005. 43(6): p. 2929-31. The presently disclosed MAbs, however, did not bind to culture filtrates from *A. terreus*, *Enterococcus faecalis* or *Staphylococcus epidermidis*, each of which has been reported to be bound by MAb EBA2.

The relative affinities of the GM-binding MAbs were determined by competition ELISA. Two of the MAbs, 476 and 838, had an affinity for GM that was approximately 10-fold higher than the other three MAbs. The % of maximal binding is shown in (FIG. 9). These results were used to calculate the dissociation constant ($K_d$) for each MAb, which was $10^{-6}$ for MAbs 24, 205 and 686, but $10^{-7}$ for MAbs 476 and 838. These values are similar to those reported for other polysaccharide-binding MAbs.

Sequencing of the variable regions of the heavy and light chains of the MAbs demonstrated that each hybridoma produced a unique MAb (data not shown). Competition ELISAs were done using each combination of the MAb pairs to confirm that the MAbs were binding to the same epitope and their relative avidities for GM. Biotinylation of the second MAb allowed the use of alkaline phosphatase-conjugated streptavidin for detection and was done by linkage of anion exchange-purified MAbs to sulfo-NHS-LC biotin. Competition among each of the MAb pairs was observed, supporting binding to similar epitopes or the presence of steric hindrance. Further, the concentrations of MAbs 476 and 838 required for competition were approximately 10-fold lower than those for the other MAbs, again suggesting that these MAbs bind more strongly than the others. The MAb 838-producing hybridoma manufactures relatively low concentrations of MAb, making use of this cell line difficult. On the basis of these results, the performance of MAbs 476 and 676 were tested in different combinations in the capture ELISA using ethanol-precipitated culture filtrates. MAb 476, when used both as the captor and detector, produced the most favorable results, with the lowest background and highest sensitivity (data not shown).

Radiolabeled MAb 476 Localizes to the Bladder in Mice with Invasive Aspergillosis.

To determine whether GM detection could form the basis for developing a nuclear medicine assay to diagnose invasive aspergillosis, MAb 476 was coupled to $Tc^{99m}$. The distribution of MAb476-Tc99 was measured in mice after Af293 infection and after sham-infection (FIG. 10). In two independent experiments, neutropenic mice were injected either intraperitoneally or intravenously with labeled MAb two days after aerosol infection with *A. fumigatus* strain 90906 and then imaged three hours later with a gamma camera. $^{99m}Tc$ was purchased from Cardinal Health, Bronx, N.Y. The MAb was labeled with $^{99m}Tc$ "directly" through binding of reduced $^{99m}Tc$ to the generated —SH groups on the antibody as described in Dadachova E. and Mirzadeh S.

Nucl Med Biol. 1997 August; 24(6):605-8. Scintigraphic imaging of infected mice with $^{99m}$Tc-MAb was performed after mice were injected IP or IV with 1.0 mCi (50 μg) $^{99m}$Tc-MAb. Three hour and 24-hr post-injection, the animals were anesthesized with isoflurane and imaged for 5 min on a gamma-camera (Siemens) equipped with ICON image processing software (FIG. 10). In sham-infected mice, the radioisotope was localized reticuloendothelial system (RES) with intense uptake in the liver and spleen (panel A). The infected animals had low amounts of antibody in the RES, but surprisingly, the label was highly localized to the bladder (panel B) in infected mice and the lung appeared cold (FIG. 10). These data suggest that an antigen recognized by MAb476 is preferentially and rapidly excreted into the bladder. Absence of marker in the bladder in the sham-infected mice suggests that this is not secondary to Tc99 metabolism, or antibody localization alone. These findings suggest that GM is excreted in the urine and supports the view that urine detection may be more sensitive than serum testing.

Example 2

Case Study: Galactomannan Enzyme Immunoassay for Diagnosing Invasive Aspergillosis Reported performance of the Galactomannan Enzyme Immunoassay (GM EIA) for diagnosis of invasive aspergillosis (IA) has been variable. Without wishing to be bound to any one particular theory, it is thought that differences exist in circulating antigen levels within and between days, possibly due to urinary GM excretion. The variability of the GM EIA in serum and urine was assessed in 40 patients with IA. Of the 40 patients enrolled, three with proven IA and 34 with probable IA contributed to analyses. Urine and sera were collected three times daily for three days. Urine samples were processed for both GM and DNA under different conditions.

In a clinical study, GM EIA was measured in sera and urine of infected patients multiple times daily to examine the kinetics of assay results within and between days and to determine whether urinary clearance of the GM antigen resulted in variability of levels. Without wishing to be bound to any one particular theory, it was thought that urinary excretion of GM results in variable kinetics of the serum assay, which may be dependent on renal function. Secondary aims were to determine comparative sensitivity of the serum and urine assays, using the BioRad GM EIA and a Taqman based PCR assay (described in depth in Musher, B., et al., *Aspergillus galactomannan enzyme immunoassay and quantitative PCR for diagnosis of invasive aspergillosis with bronchoalveolar lavage fluid.* J Clin Microbiol, 2004. 42(12): p. 5517-22).

This study was performed in a single center (FHCRC), and enrolled patients over two years (2003-2005). Patients were followed by surveillance to identify cases of proven, probable, or possible IA, as defined by consensus criteria. Ascioglu, A., et al., *Defining opportunistic invasive fungal infections in immunocompromised patients with cancer and hematopoietic stein cell transplants: an international consensus.* Clin Infect Dis, 2002. 34: p. 7-14. Inclusion criteria included receipt of allogeneic HCT or cytotoxic therapy for malignancy, and age >12 years. Patients were excluded if they could not provide non-catheterized urine (due to anuria or dependence on an indwelling catheter), did not have indwelling venous access, with dependence on ≥1 unit packed red blood cells daily, or if they weighed <30 kg.

Patients who consented to participation in the protocol had serum and urine obtained at 8-hour intervals (timed approximately 2:00, 10:00 and 18:00), for three consecutive days after diagnosis. Clinical data, including demographic, treatment and infection variables, were collected. One month after diagnosis, outcomes, including 'final' staging of IA diagnosis (possible, probable, proven), were recorded.

Forty patients were enrolled to provide an estimated 20 patients with positive serum GM EIA for descriptive analyses. It was calculated that 40 evaluable cases would provide approximately 80% power to detect an increase in sensitivity from 55% with the blood-based assay to 85% with a urine-based assay. To evaluate the impact of clinical variables on the sensitivity of serum and urine GM EIAs, logistic regression was used with generalized estimating equations (GEE) and robust variance estimates to account for repeated observations on a single individual. With this approach, the impact of serum vs. urine, time of day, and selected clinical variables that changed over time (e.g., renal function, antifungal therapy) could be assessed.

Sera and urines were tested using the GM EIA according to the manufacturer's directions (Bio-Rad, Hercules, Calif.). Urine samples were tested without processing and after concentration using Amicon Ultra-4 10K centrifugal filter units (Millipore, Billerica, Mass.). Urine (1 mL) was concentrated in the filter column by centrifugation for 10 minutes at 3500 rpm. 50 mL of concentrated sample was pipetted directly onto the microplate. The result of the EIA was reported relative to a threshold control (supplied by the manufacturer), such that a GM EIA index equals the optical density (OD) of the sample divided by the mean OD of 2 threshold controls. An index of 0.5 was used as a cut-off for positivity and all positives were re-tested for confirmation unless otherwise indicated.

Whole blood samples, urines, and concentrated urines were tested for *A. fumigatus* nucleic acids using a Taq-Man based PCR assay previously described, Musher, B., et al., *Aspergillus galactomannan enzyme immunoassay and quantitative PCR for diagnosis of invasive aspergillosis with bronchoalveolar lavage fluid.* J Clin Microbiol, 2004. 42(12): p. 5517-22, by an investigator masked to corresponding GM EIA values. Briefly, cells were lysed, centrifuged, and the pellet was treated with chaotropes, heat, potassium acetate, and isopropanol to purify fungal DNA. DNA was amplified using primers that bind to conserved sites in the fungal 18S rRNA gene, with a fluorescent probe that is specific for *Aspergillus*. All reactions were performed in triplicate to calculate mean values with standard deviations of means. This assay has been described in depth in multiple publications. Sheppard, D. C., et al., *Comparison of three methodologies for the determination of pulmonary fungal burden in experimental murine aspergillosis.* Clin Microbiol Infect, 2006. 12(4): p. 376-80; Musher, B., et al., *Aspergillus galactomannan enzyme immunoassay and quantitative PCR for diagnosis of invasive aspergillosis with bronchoalveolar lavage fluid.* J Clin Microbiol, 2004. 42(12): p. 5517-22; Khot, P. D., et al., *Development and optimization of quantitative PCR for the diagnosis of invasive aspergillosis with bronchoalveolar lavage fluid.* BMC Infect Dis, 2008. 8: p. 73; Fredricks, D. N., C. Smith, and A. Meier, *Comparison of six DNA extraction methods for recovery of fungal DNA as assessed by quantitative PCR.* J Clin Microbiol, 2005. 43(10): p. 5122-8.

Of 40 patients enrolled, three had possible IA, 34 had probable IA, and three had proven IA. 24 (70%) had received an allogeneic HCT, with the bulk receiving peripheral blood as stem cell source (24, 70%) and myeloablative conditioning (25, 74%). 33 patients (83%) had a complete set of 9 sera available for analysis, 26 (65%) had 9 urine samples analyzed. Calculated per patient, sensitivity of serum GM was 83.8% (95% CI 72.7-96.5), and the sensitivity of the urine testing (aller concentrated sample) was 78.4% (95% CI 66.2-92.8). The urine PCR sensitivity was lower at 51.4% (95% CI 37.5-70.3). The sensitivity of the urine and serum test more closely approximated each other when calculated from among patients in which an equivalent number of samples (at least 7) were available throughout testing (79% vs. 82%, respectively). Plots that demonstrate sensitivity according to cut-off to define test positivity are shown in FIG. 6. These data show that the urine assay is as sensitive compared to serum testing. Of interest, the sensitivity of detecting possible IA was higher with urine samples compared to serum, suggesting that this test might be more useful for screening for earlier diagnoses.

In summary, the sensitivity of the serum GM EIA per-sample and per-patient was 68.6% (95% CI 56.2, 83.7) and 83.8% (95% CI 72.7%, 96.5%), respectively. All tests from patients with proven IA remained positive. Variability assay positivity, however, occurred in patients with probable IA. Of 24 patients with probable IA and at least one positive sample, eight (33%) had variability over time: Sensitivity of the urine EIA increased after sample concentration, with per-sample and per-patient sensitivities estimating 57.9% (95% CI 46.0, 72.8) and 78.6% (95% Cl 64.8, 95.3), respectively. *Aspergillus* DNA was found in urine, with per-sample and per-patient sensitivity estimating 16.4% and 57.1%, respectively. No clinical variables analyzed significantly impacted assay variability, although a trend toward higher levels in samples collected later in the day was observed. This study indicates that serum and urine testing for GM can assist diagnosis, but with variable positivity between and within days.

Example 3

Case Study: Galactomannan Enzyme Immunoassay for Diagnosing Invasive Aspergillosis—Children'S Study Another multicenter study was performed to determine the specificity of the assay in children who received cytotoxic therapy and/or blood or marrow transplant. This study was specifically focused on defining the specificity of the blood-based GM EIA in children, as this specificity had been historically reported as being low due to frequent false positivity. As part of this study, urine samples also were collected and tested with the GM EIA. These samples were not pre-processed prior to sampling.

Previous studies evaluating the performance of the GM assay have noted an increased incidence of false-positive tests in children. Although this observation was never studied in depth, it was thought that this increased incidence of false-positive tests was associated with a high degree of gastrointestinal tract mucositis leading to translocation of circulating GM (or cross-reactive antigens). Children also might have variable metabolism of fungal components by virtue of differences in organ function (e.g., renal metabolism) and they may receive different cytotoxic regimens leading to variable organ toxicities. Performance of diagnostic tests can be so different in children that the FDA may require separate studies for test clearance. For these reasons, a multicenter study was conducted and a repository of blood samples was developed for the specific purpose of testing diagnostics in children. The primary goal of the study was to define parameters for use of the serum assay (GM EIA) in children; one secondary goal was to assess clinical utility of urinary assays.

Patients <19 years of age were eligible if they had one of the following conditions: leukemia with therapy predicting neutropenia solid tumor receiving intensive chemotherapy, or receipt of HCT. Patients who were dependent on daily blood product supplementation or who were of weight considered to be unsafe for blood collection were not eligible. The protocol only enrolled patients who had no evidence of IA within the prior three months. After consent, samples (blood and urines) were collected weekly for up to 8 weeks after therapy.

From May 2004 through July 2007, 215 children at risk for IA at multiple sites (Johns Hopkins, Seattle Children's Hospital, Dana Farber Cancer Center, and the University of Cincinnati) with anticipated prolonged neutropenia from chemotherapy for leukemia or solid tumor or with anticipated prolonged neutropenia from conditioning for HSCT were approached for study enrollment. From these 215 patients, 213 were enrolled in the study with 198 contributing at least one urine or serum specimen. The median age of patients was 7.8 years, males accounted for 61% of participants and patients were most commonly white (81%). Conditioning chemotherapy for HSCT (85%) was the most common etiology for neutropenia as compared to chemotherapy for malignancy (data not shown).

In total, 1,865 serum specimens for GM testing were collected from 198 patients, 886 urine specimens were collected from 183 patients, and 7 BAL specimens were collected from 4 patients. The initial GM EIA assay was positive on 146 serum specimens, but only repeatedly positive on 54 of these specimens, meeting criteria for true positive results. These 54 positive specimens were isolated from 10 patients. Likewise, the initial GM EIA assay was positive on 139 urine specimens, but only repeatedly positive on 84 of these specimens, meeting criteria for true positive results. These 84 positive specimens were taken from 39 patients. During the follow-up period, no patient was assigned the diagnosis of proven IA, one patient was identified as a probable IA and 24 patients were labeled as possible IA.

Table 2 displays the operating characteristics of the serum GM EIA for detecting probable IA only and probable or possible IA together using OD index threshold cutoffs of 0.5 and 1.0. The serum testing did not correctly identify the single case of probable IA and thus had 0% sensitivity, but maintained a high negative predictive value for both threshold cutoffs.

TABLE 2

Operating characteristics of the serum EIA GM test for detecting patients with IA

| | Sensitivity | Specificity | PPV | NPV |
| --- | --- | --- | --- | --- |
| GM index threshold of 0.5 | | | | |
| Probable IA | 0% | 95% | 0% | 99% |
| Possible and Probable IA | 13% | 96% | 30% | 89% |
| GM index threshold of 1.0 | | | | |
| Probable IA | 0% | 96% | 0% | 99% |
| Possible and Probable IA | 13% | 98% | 43% | 89% |

Similarly, Table 3 displays the operating characteristics of the urine GM EIA for detecting probable IA only and probable or possible IA using cutoffs of 0.5 and 1.0. The urine testing successfully identified the single probable IA case, resulting in 100% sensitivity and thus maintained a 100% negative predictive value. Neither serum nor urine testing had high positive predictive value results, as would be expected in the setting of low prevalence of disease. The operating characteristics when using 1.5 as the cutoff are not shown as they were equivalent to those for a cutoff of 1.0 for both serum and urine testing.

TABLE 3

Operating characteristics of the urine EIA GM test for detecting patients with IA

| | Sensitivity | Specificity | PPV | NPV |
|---|---|---|---|---|
| GM index threshold of 0.5 | | | | |
| Probable IA | 100% | 80% | 2.7% | 100% |
| Possible and Probable IA | 19% | 79% | 11% | 88% |
| GM index threshold of 1.0 | | | | |
| Probable IA | 100% | 83% | 3.2% | 100% |
| Possible and Probable IA | 14% | 82% | 9.6% | 88% |

The operating characteristics are less impressive when probable and possible cases are considered as "true disease" (data not shown). When comparing all the urine and serum GM EIA results from patients with possible disease to those with no evidence of infection the results are consistently low across all tests for all patients, as shown in FIG. 12.

The objective of this particular study was to evaluate the specificity of the serum based assay, so it was not anticipated that many patients with diagnosed IA would be enrolled. Only one patient, however, was identified as a probable IA. The probable IA diagnosis was in a 1-year, 11-month old male who had received an autologous transplant for a solid tumor. The designation of probable IA was based on the presence of bilateral pulmonary nodules identified on a chest CT scan, in conjunction with a positive GM EIA from a BAL specimen. FIG. 13 illustrates the clinical, radiographic, and laboratory highlights for this patient from the time of enrollment until the time of probable IA declaration. As shown in FIG. 13, the urine assay was repeatedly positive and it occurred before the diagnosis of IA using conventional means.

This study was performed with the primary intent of calculating specificity of the serum based assay; results demonstrate minimal loss of specificity. Possible diagnoses are not accurate, however; when considering the assumption that these patients did not have IA, the problem of false positivity would be quite substantial. The urinary based assay, although not optimized as part of these studies, performed as well, if not better than the serum based assay. Importantly, there was no excessive false positivity and the assay accurately predicted the one case of probable IA.

Further, recognition of different galactofuranose antigens in serum vs. urine may allow for enhanced specificity of the GM EIA, as 'contaminating' antigens, such as those introduced with GI translocation or administration of β-lactam antibiotics, might not be recognized in urine. Urine-based testing has potential utility in this population, in which non-invasive monitoring would be very useful.

These studies (Examples 2 and 3) demonstrate that galactomannan, or an antigen that displays a similar epitope recognized by the EbA2 antibody, is excreted in urine, verifying the potential of non-invasive diagnostic testing for both screening and diagnosis. These data provide proof of concept that an *Aspergillus* antigen is excreted in urine, although the performance of the current test (antibody and/or testing method does not provide optimal results.

Example 4

Preparation of Lateral Flow Devices

Lateral flow device cassettes were purchased from Millenia Diagnostics (San Diego, Calif.) and assembled as per the manufacturer using membranes from Millipore (Hi-Flow Plus Membranes and SureWick Pad Materials, Billerica, Mass.). Galactomannan (GM) was isolated from a 7-day liquid culture of the clinical strain, *A. fumigatus* Af293 by ethanol precipitation and further purified. Authenticity of the purified GM was verified by GM EIA (data not shown). MAb 476 was conjugated to colloidal gold as per the manufacturer's protocol (Millenia Diagnostics), and goat anti mouse IgM antibody (Southern Biotech) was used as the control.

The following general procedure can be used for preparing the reagent strip:
1. Cut a rectangular sheet of 3-10 μm pore size nitrocellulose into 15 cm×8 cm;
2. Form a reaction zone by applying a line of capture antibody across long dimension of the strip approximately 3 cm from the top of strip;
3. The width of antibody stripe will be approximately 2 mm, controlled with microprocessor;
4. Dry for 1 hour at room temperature;
5. Soak membrane in aqueous solution of inert compound to block excess binding sites on membrane (e.g., polyvinyl alcohol, 1%, w/v in 20 mM Tris, pH 7.4), 30 minutes, room temperature;
6. Rinse membranes with $dH_2O$, dry for 30 minutes at 30° C.;
7. Prepare solution of 30% sucrose in $dH_2O$, apply to membrane where conjugate reagent is located (I cm from bottom, width 3-5 mm);
8. Bake at 1 hour, 40° C.;
9. Apply Ab-microsphere (gold, see below) to membrane across sucrose glaze; and
10. Place bottom of membrane between absorbent pads, saturate with urine (containing purified GM) and observe flow characteristics and color formation at capture zone.

Example 5

Urinary Lateral Flow Device: In Vitro and In Vivo Data

Several parameters can be varied to optimize performance of a lateral flow device including, but not limited to, the type of membrane utilized (flow parameters and pore size), method of spotting antibody, appropriate buffers, gold-conjugation parameters, and fixed and flowing antibody quantities.

A device that reproducibly identified a minimal amount of 10 μg/mL GM (in 0.9% NaCl) was developed (FIG. 14, and data not shown). When the same conditions were tested using purified GM spiked into healthy human urine, however, the sensitivity of detecting the antigen appeared reduced with only faint spots visible at 100 µg/mL of antigen in urine (FIG. 15).

Device performance was improved using a high-flow membrane (240), however, the presence of urine again impaired sensitivity (FIG. 16).

Given these results using the LFD, the sensitivity of MAb476 for detecting GM in urine and PBS was tested using capture ELISA. In these studies, it was apparent that the sensitivity of detecting GM was much lower when the antigen was spiked into urine as compared to PBS (FIG. 16). When urine was sequentially diluted in PBS, however, retaining the same concentration of antigen, a small increase in sensitivity of the assay was observed (blue line). This observation provided an initial indication that an inhibitor was present in urine, which potentially could be diluted.

To test this hypothesis further, capture ELISA was performed using a constant antibody-antigen concentration in urine diluted with PBS-BSA. As shown in FIG. 17, a 1/10 dilution of urine resulted in a 2-fold increase in absorbance, even in the presence of the same MAb concentration (55 µg/mL).

Preliminary studies were performed to determine if altering the basic properties of urine could increase sensitivity of the reaction in capture ELISA. No parameter tested effectively increased absorbance (FIG. 18). Pre-treating urine by filtration through a desalting column, however, resulted in a dramatic improvement of sensitivity of urine, such that the sensitivity of the test in urine was approximately equivalent to that of PBS (FIG. 19).

These data suggest that urine contains an inhibitor that interferes with the MAb476 detection of antigen and that its molecular weight is <7 KDa, which allows elimination of the inhibitor by filtration through a desalting column. Potential inhibitors include small molecules, such as salts, urea, and other chaotropic components, not yet identified. Prior results, which showed that the detection of GM is better after urine "concentration," effectively demonstrated the same effect, but an important step appears to be elimination of an inhibitor in urine, not necessarily concentration of antigen.

Performance of urinary testing using the MAb476-LFD has been compared to the GM EIA using materials obtained from infected animals. Guinea pigs were infected with Af293 (Patterson Laboratory, University of Texas Health Sciences Center, San Antonio, Tex.) after animals were immunosuppressed using cyclophosphamide, as outlined in prior publications. At specified times (1 hr, day 3, day 5, and day 7 after infection), animals were sacrificed, bronchoalveolar lavage (BAL) was performed, blood was harvested to serum, and bladder puncture was performed to collect urine. GM EIA and β-glucan (Fungitell, Associates of Cape Cod. Inc., East Falmouth, Mass.) assays were performed on BAL and serums, and the results were compared to urine LFD results. FIG. 20A shows the GM and β-glucan index values and concentrations, respectively, of BAL and serum from infected animals over time. BAL samples showed higher sensitivity over serum as the former samples tested positive at earlier time points vs. serum, and this was true for both fungal antigens. Neat guinea pig urines were tested for GM positivity by LFD. Correlation between infection (defined as positive BAL and/or serum GM EIA), and LFD results are shown in FIG. 20B. The LFD positivity results correlated more closely with serum GM index values than with BAL values (FIG. 20B, lower graph). Unexpectedly, positive GM was measured in BAL, serum and urines by both GM EIA and LFD in some of the animals that were not infected (data not shown). Further investigation determined that prolonged immunosuppression and incomplete isolation of the guinea pigs was conducive to infection of control animals. In light of these findings, definitive conclusions could not be drawn regarding guinea pig urine GM positivity by LFD as appropriate negative control samples were not available. The infection model has been addressed and modified to avert future unintentional infections. A second set of guinea pig BAL, serum and urine samples and accompanying EIA GM and β-glucan assay results have been received to repeat the LFD studies. Thus, the current data using an animal infection model are preliminary, but the model shows promise as an alternative to patient samples to detect GM in urine originating from infected individuals.

In summary, these studies demonstrate the detection of GM, or an antigen that is cross-reactive to the Eb-A2 antibody, in urine in animal and human samples. In some cases, sensitivity for detecting GM in urine appears to be higher than that in serum. A novel antibody has been produced using a novel microbial antigen and is defined by its binding characteristics. The antibody has some degree of cross-reactivity to antigens that are known to be identified by the other available antibody (Eb-A2) and some novel reactivity, as well.

Further, the presently disclosed subject matter demonstrates in animal models that the GM antigen is preferentially localized to the bladder early after infection, which again supports the conceptual development of a urinary diagnostic device. The presently disclosed subject matter also demonstrates that, in some embodiments, the performance of the device can be improved by processing or treating the urine sample prior to testing, although this step is not necessary in all embodiments. Other urine-based diagnostics frequently require some step in specimen processing to provide optimal results as part of "kit" testing in laboratories. This step, however, does not preclude the use of the presently disclosed device for point-of-care testing.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Knutsen, A., et al., *Asp f1 CD4+ Th2-like T cell lines in allergic bronchopulmonary aspergillosis.* J Allergy Clin Immunol, 1994. 94: p. 215-221.

Kawamura, S., et al., *Clinical evaluation of 61 patients with pulmonary aspergilloma.* Intern Med, 2000. 39(3): p. 209-12.

Israel, H., G. Lenchner, and G. Atkinson, *Sarcoidosis and aspergilloma.* Chest, 1982. 82: p. 430-32.

Kirsten, D., et al., *Invasive aspergillosis in cavitary lung sarcoidosis.* Pneumologie, 1992. 46: p. 239-242.

Wollschlager, C. and F. Kan, *Aspergilloma complicating sarcoidosis. A prospective study of 100 patients.* Chest, 1984. 86: p. 585-88.

Staples, C. A., et al., *Invasive pulmonary aspergillosis in AIDS: radiographic, CT, and pathologic findings.* Radiology, 1995. 196(2): p. 409-14.

Hines, D. W., et al., *Pseudomembranous tracheobronchitis caused by Aspergillus.* Am Rev Respir Dis, 1991. 143(6): p. 1408-11.

Khoo, S. H. and D. W. Denning, *Invasive aspergillosis in patients with AIDS.* Clin Infect Dis, 1994. 19 Suppl 1(2): p. S41-8.

Duong, M., et al., *Kinetic study of host defense and inflammatory response to Aspergillus fumigatus in steroid-induced immunosuppressed mice.* J Infect Dis, 1998. 178: p. 1472-82.

Berenguer, J., et al., *Pathogenesis of pulmonary aspergillosis. Granulocytopenia versus cyclosporine and methylprednisolone-induced immunosuppression.* Am J Respir Crit Care Med, 1995. 152(3): p. 1079-86.

Marr, K., et al., *Aspergillosis in HSCT recipients: evidence for two distinct pathophysiologic conditions associated with engraftment status.* Blood, 2000. 96(11):

Boeckh, M., et al., *Successful modification of a pp65 antigenemia-based early treatment strategy for prevention of cytomegalovirus disease in allogeneic marrow transplant recipients.* Blood, 1999. 93(5): p. 1781-2.

Boeckh, M., T. Gooley, and R. Bowden, *Effect of high-dose acyclovir on survival in allogeneic marrow transplant recipients who received ganciclovir at engraftment or for cytomegalovirus pp65 antigenemia.* J Infect Dis, 1998. 1998(178): p. 1153-7.

Boeckh, M., et al., *Plasma polymerase chain reaction for cytomegalovirus DNA after allogeneic marrow transplantation: comparison with polymerase chain reaction using peripheral blood leukocytes, pp65 antigenemia, and viral culture.* Transplantation, 1997. 64: p. 108-113.

Boeckh, M., et al., *Cytomegalovirus pp65 antigenemia-guided early treatment with ganciclovir versus ganciclovir at engraftment after allogeneic marrow transplantation: a randomized double-blind study.* Blood, 1996. 88(10): p. 4063-4071.

Slavin, M. A., et al., *Efficacy and safety of fluconazole prophylaxis for fungal infections after marrow transplantation—a prospective, randomized, double-blind study.* Journal Of Infectious Diseases., 1995. 171(6): p. 1545-52.

Hansen, J. A., et al., *Bone marrow transplants from unrelated donors for patients with chronic myeloid leukemia.* The New England Journal of Medicine, 1998. 338: p. 962-8.

Marr, K., et al., *Epidemiology and outcome of mould infections in hematopoietic stem cell transplant recipients.* Clin Infect Dis, 2002. 34: p. 909-917.

Wald, A., et al., *Epidemiology of Aspergillus infections in a large cohort of patients undergoing bone marrow transplantation.* The Journal of Infectious Diseases, 1997. 175: p. 1459-66.

Neofytos, D., et al., *Epidemiology and outcome of invasive fungal infection in adult hematopoietic stem cell transplant recipients: analysis of Multicenter Prospective Antifungal Therapy (PATH) Alliance registry.* Clin Infect Dis, 2009. 48(3): p. 265-73.

Durkin, M., et al., *Diagnosis of coccidioidomycosis with use of the Coccidioides antigen enzyme immunoassay.* Clin Infect Dis, 2008. 47(8): p. e69-73.

Spector, D., et al., *Antigen and antibody testing for the diagnosis of blastomycosis in dogs.* J Vet Intern Med, 2008. 22(4): p. 839-43.

Kim, Y., et al., *Halo sign on high resolution CT: findings in spectrum of pulmonary diseases with pathologic correlation.* J Comput Assist Tomogr, 1999. 23(4): p. 622-6.

Caillot, D., et al., *Improved management of invasive aspergillosis in neutropenic patients using early thoracic computed tomographic scan and surgery.* Journal of Clinical Oncology, 1997. 15(1): p. 139-147.

Levy, H., et al., *The value of bronchoalveolar lavage and bronchial washings in the diagnosis of invasive pulmonary aspergillosis.* Respir Med, 1992. 86(3): p. 243-8.

Hoffer, E. A., et al., *Accuracy of percutaneous lung biopsy for invasive pulmonary aspergillosis.* Pediatr Radiol, 2001. 31(3): p. 144-52.

de Sevaux, R. G., et al., *Microgranulomatous aspergillosis in a patient with chronic granulomatous disease: cure with voriconazole.* Clin Infect Dis, 1998. 26(4): p. 996-7.

Marr, K. A., et al., *Detection of galactomannan antigenemia by enzyme immunoassay for the diagnosis of invasive aspergillosis: variables that affect performance.* J Infect Dis, 2004. 190(3): p. 641-9.

Upton, A., et al., *Reproducibility of low galactomannan enzyme immunoassay index values in multiple laboratories.* in preparation, 2005.

Marr, K. A., *Aspergillus galactomannan index: a surrogate end point to assess outcome of therapy?* Clin Infect Dis, 2008. 46(9): p. 1423-5.

Sheppard, D. C., et al., *Comparison of three methodologies for the determination of pulmonary fungal burden in experimental murine aspergillosis.* Clin Microbiol Infect 2006. 12(4): p. 376-80.

Upton, A., W. Leisenring, and K. A. Marr, *(1→3) beta-D-glucan assay in the diagnosis of invasive fungal infections.* Clin Infect Dis, 2006. 42(7): p. 1054-6; author reply 1056.

Marr, K. A. and W. Leisenring, *Design issues in studies evaluating diagnostic tests for aspergillosis.* Clin Infect Dis, 2005.41 Suppl 6: p. S381-6.

Marr, K. A., et al., *Antifungal therapy decreases sensitivity of the Aspergillus galactomannan enzyme immunoassay.* Clin Infect Dis, 2005. 40(12): p. 1762-9.

Musher, B., et al., *Aspergillus galactomannan enzyme immunoassay and quantitative PCR for diagnosis of invasive aspergillosis with bronchoalveolar lavage fluid.* J Clin Microbiol, 2004. 42(12): p. 5517-22.

Stynen, D., et al., *Rat monoclonal antibodies against Aspergillus galactomannan.* Infect Immun, 1992. 60: p. 2237-2245.

Denning, D. W., et al., *Efficacy and safety of voriconazole in the treatment of acute invasive aspergillosis.* Clin Infect Dis, 2002. 34(5): p. 563-71.

Maertens, J. A., et al., *Optimization of the cutoff value for the Aspergillus double-sandwich enzyme immunoassay.* Clin Infect Dis, 2007. 44(10): p. 1329-36.

Rath, P. M. and R. Ansorg, *Value of environmental sampling and molecular typing of aspergilli to assess nosocomial sources of aspergillosis.* J Hosp Infect, 1997. 37(1): p. 47-53.

Eskens, F. A., et al., *Septic shock caused by group G beta-haemolytic streptococci as presenting symptom of acute myeloid leukaemia.* Neth J Med, 1995. 46(3): p. 153-5.

Einsele, H., et al., *Prediction of invasive pulmonary aspergillosis from colonisation of lower respiratory tract before marrow transplantation.* Lancet, 1998. 352(9138): p. 1443.

Buchheidt, D., et al., *Detection of Aspergillus species in blood and bronchoalvolar lavage samples from immuno-* compromised patients by means of 2-step polymerase chain reaction: clinical results. Clin Infect Dis, 2001. 33: p. 428-35.

Meersseman, W., et al., *Galactomannan in bronchoalveolar lavage fluid: a tool for diagnosing aspergillosis in intensive care unit patients*. Am J Respir Crit Care Med, 2008. 177(1): p. 27-34.

Husain, S., et al., *Performance characteristics of the platelia Aspergillus enzyme immunoassay for detection of Aspergillus galactomannan antigen in bronchoalveolar lavage fluid*. Clin Vaccine Immunol, 2008. 15(12): p. 1760-3.

Nguyen, M. H., et al., *Use of bronchoalveolar lavage to detect galactomannan for diagnosis of pulmonary aspergillosis among nonimmunocompromised hosts*. J Clin Microbiol, 2007. 45(9): p. 2787-92.

Husain, S., et al., *Aspergillus galactomannan antigen in the bronchoalveolar lavage fluid for the diagnosis of invasive aspergillosis in lung transplant recipients*. Transplantation, 2007. 83(10): p. 1330-6.

Clancy, C. J., et al., *Bronchoalveolar lavage galactomannan in diagnosis of invasive pulmonary aspergillosis among solid-organ transplant recipients*. J Clin Microbiol, 2007. 45(6): p. 1759-65.

Sanguinetti, M., et al., *Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis*. J Clin Microbiol, 2003. 41(8): p. 3922-5.

Becker, M. J., et al., *Galactomannan detection in computerized tomography-based broncho-alveolar lavage fluid and serum in haematological patients at risk for invasive pulmonary aspergillosis*. Br J Haematol, 2003. 121(3): p. 448-57.

Jensen, H. E., et al., *Detection of galactomannan and the 18 kDa antigen from Aspergillus fumigatus in serum and urine from cattle with systemic aspergillosis*. Zentralbl Veterinarmed [B], 1993. 40(6): p. 397-408.

Bennett, J. E., M. M. Friedman, and B. Dupont, *Receptor-mediated clearance of Aspergillus galactomannan*. J Infect Dis, 1987. 155(5): p. 1005-10.

Klont, R. R., M. A. Mennink-Kersten, and P. E. Verweij, *Utility of Aspergillus antigen detection in specimens other than serum specimens*. Clin Infect Dis, 2004. 39(10): p. 1467-74.

Ansorg, R., E. Heintschel von Heinegg, and P. M. Rath, *Aspergillus antigenuria compared to antigenemia in bone marrow transplant recipients*. Eur J Clin Microbiol Infect Dis, 1994. 13(7): p. 582-9.

Dupont, B., et al., *Galactomannan antigenemia and antigenuria in aspergillosis: studies in patients and experimentally infected rabbits*. J Infect Dis, 1987. 155(1): p. 1-11.

Rogers, T. R., K. A. Haynes, and R. A. Barnes, *Value of antigen detection in predicting invasive pulmonary aspergillosis*. Lancet, 1990. 336(8725): p. 1210-3.

Tsoni, S. V. and G. D. Brown, *beta-Glucans and dectin-1*. Ann N Y Acad Sci, 2008. 1143: p. 45-60.

Obayashi, T., et al., *Plasma (1->3)-beta-D-glucan measurement in diagnosis of invasive deep mycosis and fungal febrile episodes*. Lancet, 1995. 345(8941): p. 17-20.

Gersuk, G. M., et al., *Dectin-1 and TLRs permit macrophages to distinguish between different Aspergillus fumigatus cellular states*. J Immunol, 2006. 176(6): p. 3717-24.

Hohl, T. M., et al., *Aspergillus fumigatus triggers inflammatory responses by stage-specific beta-glucan display*. PLoS Pathog, 2005. 1(3): p. e30.

Steele, C., et al., *The beta-glucan receptor dectin-1 recognizes specific morphologies of Aspergillus fumigatus*. PLoS Pathog, 2005. 1(4): p. e42.

Hachem, R. Y., et al., *Utility of galactomannan enzyme immunoassay and (1.3) beta-D-glucan in diagnosis of invasive fungal infections: low sensitivity for Aspergillus fumigatus infection in hematologic malignancy patients*. J Clin Microbiol, 2009. 47(1): p. 129-33.

Senn, L., et al., *1,3-Beta-D-glucan antigenemia for early diagnosis of invasive fungal infections in neutropenic patients with acute leukemia*. Clin Infect Dis, 2008. 46(6): p. 878-85.

Persat, F., et al., *Contribution of the (1→3)-beta-D-glucan assay for diagnosis of invasive fungal infections*. J Clin Microbiol, 2008. 46(3): p. 1009-13.

Pickering, J. W., et al., *Evaluation of a (1→3)-beta-D-glucan assay for diagnosis of invasive fungal infections*. J Clin Microbiol, 2005. 43(12): p. 5957-62.

Ellis, M., et al., *Assessment of the clinical utility of serial beta-D-glucan concentrations in patients with persistent neutropenic fever*. J Med Microbiol, 2008. 57(Pt 3): p. 287-95.

Boulware, D. R., et al., *Rapid diagnosis of pneumococcal pneumonia among HIV-infected adults with urine antigen detection*. J Infect, 2007. 55(4): p. 300-9.

Sutherland, M. D., et al., *In vivo fate and distribution of poly-gamma-D-glutamic acid, the capsular antigen from Bacillus anthracis*. Infect Immun, 2008. 76(3): p. 899-906.

Clarke, S. C., *Urinary antigen diagnosis of meningococcal disease*. Br J Biomed Sci, 2000. 57(2): p. 153-5.

van Burik, J., et al., *Panfungal PCR assay for detection of fungal infection in human blood samples*. J Clin Microbiol, 1998. 36(5): p. 1169-1175.

Hebart, H., et al., *Early detection of aspergillus infection after allogeneic stem cell transplantation polymerase chain reaction screening*. J Infect Dis, 2000. 181(5): p. 1713-9.

Kami, M., et al., *Use of real-time PCR on blood samples for diagnosis of invasive aspergillosis*. Clin Infect Dis, 2001. 33(9): p. 1504-12.

Costa, C., et al., *Real-Time PCR Coupled with Automated DNA Extraction and Detection of Galactomannan Antigen in Serum by Enzyme-Linked Immunosorbent Assay for Diagnosis of Invasive Aspergillosis*. J Clin Microbiol, 2002. 40(6): p. 2224-2227.

Costa, C., et al., *Development of two real-time quantitative TaqMan PCR assays to detect circulating Aspergillus fumigatus DNA in serum*, J Microbiol Methods, 2001. 44(3): p. 263-9.

Cuenca-Estrella, M., et al., *Value of serial quantification of fungal DNA by a real-time PCR-based technique for early diagnosis of invasive Aspergillosis in patients with febrile neutropenia*. J Clin Microbiol, 2009. 47(2): p. 379-84.

Suarez, F., et al., *Detection of circulating Aspergillus fumigatus DNA by real-time PCR assay of large serum volumes improves early diagnosis of invasive aspergillosis in high-risk adult patients under hematologic surveillance*. J Clin Microbial, 2008. 46(11): p. 3772-7.

Nielsen, K., et al., *Prototype single step lateral flow technology for detection of avian influenza virus and chicken antibody to avian influenza virus*. J Immunoassay Immunochem, 2007. 28(4): p. 307-18.

Mokkapati, V. K., et al., *Evaluation of UPlink-RSV: prototype rapid antigen test for detection of respiratory syncytial virus injection.* Ann NY Acad Sci, 2007. 1098: p. 476-85.

Koide, M., et al., *Comparative evaluation of Duopath Legionella lateral flow assay against the conventional culture method using Legionella pneumophila and Legionella anisa strains.* Jpn J Infect Dis, 2007. 60(4): p. 214-6.

Roson, B., et al., *Contribution of a urinary antigen assay (Binax NOW) to the early diagnosis of pneumococcal pneumonia.* Clin Infect Dis, 2004. 38(2): p. 222-6.

Weatherall, C., R. Paoloni, and T. Gottlieb, *Point-of-care urinary pneumococcal antigen less in the emergency department for community acquired pneumonia.* Emerg Med J, 2008. 25(3): p. 144-8.

Kappe, R. and A. Schulze-Berge, *New cause for false-positive results with the Pastorex Aspergillus antigen latex agglutination test.* J Clin Microbial, 1993. 31(9): p. 2489-90.

Stynen, D., et al., *Rat monoclonal antibodies against Aspergillus galactomannan.* Infect Immun, 1992. 60(6): p. 2237-45.

Swanink, C. M., et al., *Specificity of a sandwich enzyme-linked immunosorbent assay for detecting Aspergillus galactomannan.* J Clin Microbial, 1997. 35(1): p. 257-60.

Thornton, C. R., *Development of an immunochromatographic lateral-flow device for rapid serodiagnosis of invasive aspergillosis.* Clin Vaccine Immunol, 2008. 15(7): p. 1095-105.

Ascioglu, A., et al., *Defining opportunistic invasive fungal infections in immunocompromised patients with cancer and hematopoietic stem cell transplants: an international consensus.* Clin. Infect Dis, 2002. 34: p. 7-14.

Khot, P. D., et al., *Development and optimization of quantitative PCR for the diagnosis of invasive aspergillosis with bronchoalveolar lavage fluid.* BMC Infect Dis, 2008. 8: p. 73.

Fredricks, D. N., C. Smith, and A. Meier, *Comparison of six DNA extraction methods for recovery of fungal DNA as assessed by quantitative PCR.* J Clin Microbial, 2005. 43(10): p. 5122-8.

Dalle, F., et al., *Cryptococcus neoformans Galactoxylomannan contains an epitope(s) that is cross-reactive with Aspergillus Galactomannan.* J Clin Microbial, 2005. 43(6): p. 2929-31.

Brown, M. C., *Antibodies: key to a robust lateral flow immunoassay, in Lateral Flow Immunoassay,* H. Y. T. R. C. Wong, Editor. 2009, Humana Press: New York, N.Y. p. 59-74.

Mennink-Kersten, M. A., et al., *Bifidobacterium lipoteichoic acid and false ELISA reactivity in aspergillus antigen detection.* Lancet, 2004. 363(9405): p. 325-7.

Walsh, T. J., et al., *Experimental pulmonary aspergillosis due to Aspergillus terreus: pathogenesis and treatment of an emerging fungal pathogen resistant to amphotericin B.* J Infect Dis, 2003. 188(2): p. 305-19.

Marr, K., et al., *Antifungal therapy decreases sensitivity of the Platelia Aspergillus galactomannan enzyme immunoassay.* submitted, 2005:

Leisenring, W., M. Pepe, and G. Longton, *A marginal regression modelling framework for evaluating medical diagnostic tests.* Statistics in Medicine, 1997. 16(11): p. 1263-1281.

Sheppard, D. C., et al., *Novel inhalational murine model of invasive pulmonary aspergillosis.* Antimicrob Agents Chemother, 2004. 48(5): p. 1908-11.

Sheppard, D. C., et al., *Standardization of an experimental murine model of invasive pulmonary aspergillosis.* Antimicrob Agents Chemother, 2006. 50(10): p. 3501-3.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A kit comprising:

a. an antibody which recognizes at least one epitope of a galactofuranose residue of a polysaccharide secreted by *Aspergillus fumigatus*, which is attached to a first agent which renders the antibody detectable on a solid surface, wherein the antibody which recognizes at least one epitope of the galactofuranose residue of the polysaccharide is selected from the group consisting of monoclonal antibody 205 (MAb 205) comprising a variable heavy ($V_H$) domain encoded by SEQ ID NO:1 and a variable light ($V_L$) domain encoded by SEQ ID NO:2; monoclonal antibody 24 (MAb 24) comprising a $V_H$ domain encoded by SEQ ID NO:3 and a $V_L$ domain encoded by SEQ ID NO:4; monoclonal antibody 686 (MAb686) comprising a $V_H$ domain encoded by SEQ ID NO:5 and a $V_L$ domain encoded by SEQ ID NO:6; monoclonal antibody 838 (MAb 838) comprising a $V_H$ domain encoded by SEQ ID NO:7 and a $V_L$ domain encoded by SEQ ID NO:8; and monoclonal antibody 476 (MAb 476) comprising a $V_H$ domain encoded by SEQ ID NO:9 and a $V_L$ domain encoded by SEQ ID NO:10;

b. a lateral flow device on which is immobilized a second agent capable of capturing the antibody specific for at least one epitope of the galactofuranose residue of the polysaccharide when it has reacted with said epitope; and c. instructions on using the kit to detect a fungal infection by testing a urine sample of a human subject suspected of having, having, or susceptible to having a fungal infection, wherein the antibody and the first and second agents are present in appropriate concentrations to detect the fungal antigen in the urine specimen.

2. The kit of claim 1 wherein the antibody which recognizes at least one epitope of the galactofuranose residue of the polysaccharide is monoclonal antibody 476 (MAb 476) comprising a $V_H$ domain encoded by SEQ ID NO:9 and a $V_L$ domain encoded by SEQ ID NO:10.

3. The kit of claim 1 wherein the first agent is an optically detectable label.

4. The kit of claim 3 wherein the optically detectable label is a latex bead impregnated with a fluorescent tag.

5. The kit of claim 1 wherein the lateral flow device comprises a solid surface along which the antibody specific for at least one epitope of the galactofuranose residue of the polysaccharide attached to the first agent can migrate by capillary action.

6. The kit of claim 1 wherein the second agent comprises an antibody specific for at least one epitope of the galactofuranose residue of the polysaccharide.

7. The kit of claim 1 wherein also immobilized on the lateral flow device is a third agent capable of capturing the antibody specific for at least one epitope of the galactofuranose residue of the polysaccharide when it has not reacted with said epitope.

8. The kit of claim 7 wherein the lateral flow device comprises a solid surface along which the antibody specific for at least one epitope of the galactofuranose residue of the polysaccharide attached to the first agent can migrate by capillary action which has in order along the capillary flow path a sample application zone, an immobilized second agent and an immobilized third agent.

9. The kit of claim 1 also containing a desalting column for removing an inhibitor found in urine samples which interferes with the binding of the antibody specific for at least one epitope of the galactofuranose residue of the polysaccharide to such epitopes.

10. The kit of claim 1 wherein the instructions relate to the use of the kit to screen the human subject for a fungal infection.

11. An antibody which recognizes at least one epitope of a galactofuranose residue of a polysaccharide secreted by *Aspergillus fumigatus* wherein it is selected from the group consisting of monoclonal antibody 205 (MAb 205) comprising a variable heavy ($V_H$) domain encoded by SEQ ID NO:1 and a variable light ($V_L$) domain encoded by SEQ ID NO:2; monoclonal antibody 24 (MAb 24) comprising a $V_H$ domain encoded by SEQ ID NO:3 and a $V_L$ domain encoded by SEQ ID NO:4; monoclonal antibody 686 (MAb686) comprising a $V_H$ domain encoded by SEQ ID NO:5 and a $V_L$ domain encoded by SEQ ID NO:6; monoclonal antibody 838 (MAb 838) comprising a $V_H$ domain encoded by SEQ ID NO:7 and a $V_L$ domain encoded by SEQ ID NO:8; and monoclonal antibody 476 (MAb 476) comprising a $V_H$ domain encoded by SEQ ID NO:9 and a $V_L$ domain encoded by SEQ ID NO:10.

12. The antibody of claim 11 wherein it is attached to a first agent that renders it detectable.

13. The antibody of claim 12 wherein the first agent is an optically detectable label.

14. The antibody of claim 13 wherein the optically detectable label is a latex bead impregnated with a fluorescent tag.

15. The antibody of claim 11 wherein it is monoclonal antibody 476 (MAb 476) comprising a $V_H$ domain of SEQ ID NO:9 and a $V_L$ domain of SEQ ID NO:10.

16. The antibody of claim 11 wherein it is attached to a second agent by which it can be immobilized on a lateral flow device.

17. A method for diagnosing a microbial infection in a human subject suspected of having, having, or susceptible to having a fungal infection by detecting the presence of at least one polysaccharide comprising a galactofuranose residue in a urine sample of the human subject comprising:

a. contacting the urine sample with an antibody which recognizes at least one epitope of a galactofuranose residue of a polysaccharide secreted by *Aspergillus fumigatus*, which is attached to a first agent which renders the antibody detectable on a solid surface, wherein the antibody specific for at least one epitope of the galactofuranose residue of the polysaccharide is selected from the group consisting of monoclonal antibody 205 (MAb 205) comprising a variable heavy ($V_H$) domain encoded by SEQ ID NO:1 and a variable light ($V_L$) domain encoded by SEQ ID NO:2; monoclonal antibody 24 (MAb 24) comprising a $V_H$ domain encoded by SEQ ID NO:3 and a $V_L$ domain encoded by SEQ ID NO:4; monoclonal antibody 686 (MAb686) comprising a $V_H$ domain encoded by SEQ ID NO:5 and a $V_L$ domain encoded by SEQ ID NO:6; monoclonal antibody 838 (MAb 838) comprising a $V_H$ domain encoded by SEQ ID NO:7 and a $V_L$ domain encoded by SEQ ID NO:8; and monoclonal antibody 476 (MAb 476) comprising a $V_H$ domain encoded by SEQ ID NO:9 and a $V_L$ domain encoded by SEQ ID NO:10;

b. contacting the urine sample with a lateral flow device on which is immobilized a second agent capable of capturing the antibody specific for at least one epitope of the galactofuranose residue of the polysaccharide when it has reacted with said epitope; and c. detecting a fungal infection in accordance with instructions provided with a kit also containing the antibody and the lateral flow device.

18. The method of claim 17 wherein the antibody specific for at least one epitope of the galactofuranose residue of the polysaccharide is monoclonal antibody 476 (MAb 476) comprising a $V_H$ domain encoded by SEQ ID NO:9 and a $V_L$ domain encoded by SEQ ID NO:10.

19. The method of claim 17 wherein the first agent is an optically detectable label.

20. The method of claim 19 wherein the optically detectable label is a latex bead impregnated with a fluorescent tag.

21. The method of claim 17 wherein the lateral flow device comprises a solid surface along which the antibody specific for at least one epitope of the galactofuranose residue of the polysaccharide attached to the first agent can migrate by capillary action.

22. The method of claim 21 wherein also immobilized on the lateral flow device is a third agent capable of capturing the antibody specific for at least one epitope of the galactofuranose residue of the polysaccharide when it has not reacted with said epitope.

23. The method of claim 17 wherein a mechanism for removing an inhibitor found in urine samples which interferes with the binding of the antibody specific for at least one epitope of the galactofuranose residue of the polysaccharide to such epitopes is utilized.

24. The method of claim 17 wherein the diagnosis involves screening the human subject for the presence of a fungal infection.

25. The kit of claim 1 wherein the instructions are on using the kit to detect Invasive Aspergillosis by testing the urine sample of an immunocompromised human subject and the fungal infection is Invasive Aspergillosis.

26. The method of claim 17 wherein the human subject is immunocompromised and the fungal infection is Invasive Aspergillosis.

\* \* \* \* \*